US008920333B2

(12) United States Patent
Younes

(10) Patent No.: US 8,920,333 B2
(45) Date of Patent: Dec. 30, 2014

(54) METHOD AND DEVICE FOR GENERATING OF A SIGNAL THAT REFLECTS RESPIRATORY EFFORTS IN PATIENTS ON VENTILATORY SUPPORT

(75) Inventor: Magdy Younes, Toronto (CA)

(73) Assignee: YRT Limited, Winnipeg, Manitoba (CA)

( * ) Notice: Subject to any disclaimer, the term of this patent is extended or adjusted under 35 U.S.C. 154(b) by 1608 days.

(21) Appl. No.: 12/226,982

(22) PCT Filed: May 12, 2006

(86) PCT No.: PCT/CA2006/000756
§ 371 (c)(1),
(2), (4) Date: Apr. 30, 2009

(87) PCT Pub. No.: WO2007/131314
PCT Pub. Date: Nov. 22, 2007

(65) Prior Publication Data
US 2009/0221926 A1    Sep. 3, 2009

(51) Int. Cl.
*A61B 5/08* (2006.01)
*A61B 5/085* (2006.01)
*A61B 5/00* (2006.01)
*A61M 16/00* (2006.01)

(52) U.S. Cl.
CPC ........ *A61B 5/085* (2013.01); *A61M 2016/0042* (2013.01); *A61B 5/7239* (2013.01); *A61M 2016/0027* (2013.01); *A61M 2016/0039* (2013.01); *A61M 16/0051* (2013.01)
USPC ....................................... 600/529

(58) Field of Classification Search
USPC ........... 600/529; 128/204.18, 204.21, 204.22, 128/204.23
See application file for complete search history.

(56) References Cited

U.S. PATENT DOCUMENTS

| 4,036,222 A | 7/1977 | Gillard et al. |
| 5,316,009 A | 5/1994 | Yamada |

(Continued)

FOREIGN PATENT DOCUMENTS

| WO | WO2004/002561 | * | 1/2004 |
| WO | WO2004/080516 | * | 9/2004 |

OTHER PUBLICATIONS

Leung, P., Jubran, A., Tobin, M.J. Comparison of assisted ventilator modes on triggering, patient effort, and dyspnea. Am. J Respir Crit Care Med 155: p. 1940-48 (1997).

(Continued)

*Primary Examiner* — Jacqueline Cheng
*Assistant Examiner* — Michael Catina
(74) *Attorney, Agent, or Firm* — Michael I. Stewart; Sim & McBurney

(57) ABSTRACT

A method and device for generating a signal that mirrors changes in the level of effort exerted by respiratory muscles of patients on mechanical ventilatory support comprising: monitoring and storing airway pressure ($P_{aw}$), rate of gas flow (F), and volume of gas flow (V), and generating a composite pressure signal using resistive pressure units ($K_F$) determined from elapsed data and selected to minimize step changes in the calculated signal and elastic pressure units ($K_v$) determined from elapsed data by steps comprising: —scanning stored F or $P_{aw}$ during exhalation and identifying where their trajectory transiently reverses direction to detect transients; —selecting points within the exhalation that are at preselected distances away from the transients; —calculating the value of $K_v$ required to force the values of the calculated signal at said selected points in elapsed breaths to be substantially equal when the selected value of $K_F$ is used as the flow coefficient.

34 Claims, 26 Drawing Sheets

(56) References Cited

U.S. PATENT DOCUMENTS

| | | | |
|---|---|---|---|
| 5,844,622 A | 12/1998 | Hulvey | |
| 5,884,622 A * | 3/1999 | Younes | 128/204.21 |
| 6,158,432 A | 12/2000 | Biondi et al. | |
| 6,257,234 B1 | 7/2001 | Sun | |
| 6,305,374 B1 | 10/2001 | Zdrojkowski et al. | |
| 6,435,182 B1 | 8/2002 | Lutchen et al. | |
| 6,796,305 B1 | 9/2004 | Banner et al. | |
| 6,837,242 B2 * | 1/2005 | Younes | 128/204.22 |
| 7,210,478 B2 | 5/2007 | Banner et al. | |
| 2003/0001339 A1 | 1/2003 | Inoue | |
| 2004/0050387 A1 * | 3/2004 | Younes | 128/204.18 |

OTHER PUBLICATIONS

Yamada Y., Du, H.L. "Analysis of the mechanisms of expiratory asynchrony in pressure support ventilation: a mathematical approach". J. Appl Physiol 88: 2143-2150 (2000).

Younes M. "Patient-ventilator interaction with pressure-assisted modalities of ventilatory support." Seminars in Respiratory Medicine 14: 299-322 (1993).

Younes et al. "A method for noninvasive determination of inspiratory resistance during proportional assist ventilation." Am J. Respir, Crit Care Med 163: 829-39 (2001).

* cited by examiner

METHOD AND DEVICE FOR GENERATING OF A SIGNAL THAT REFLECTS RESPIRATORY EFFORTS IN PATIENTS ON VENTILATORY SUPPORT

REFERENCE TO RELATION APPLICATIONS

This application is a U.S. National Phase filing under 35 USC 371 of PCT/CA2006/000756 filed May 12, 2006.

FIELD OF INVENTION

This invention relates to assisted mechanical ventilation.

BACKGROUND TO THE INVENTION

Ventilatory assist devices are machines used in the treatment of respiratory failure and sleep disorders in hospital or home settings. With assisted ventilation (e.g. assist volume cycled ventilation, pressure support ventilation, bi-level assist in the case of non-invasive devices and proportional assist ventilation) ventilator cycles are triggered by the patient and are intended to coincide with patient's inspiratory effort, beginning the support when inspiratory effort starts and ending the support at the end of patient's inspiratory effort. In practice, however, the ventilator cycle never begins at the onset of patient's inspiratory effort (trigger delay) and the end of the ventilator's inflation phase only rarely coincides with the end of inspiratory effort (cycling-off errors). FIG. 1 provides an example. The bottom channel is transdiaphragmatic pressure (measured by esophageal and gastric catheters) and reflects true patient inspiratory effort. As may be seen, ventilator cycle was triggered several hundred milliseconds after onset of effort (interval between vertical lines) and the inflation cycle continued well beyond the effort. In fact, the ventilator was cycling almost completely out-of-phase with the patient. Trigger delay is often so marked that some efforts completely fail to trigger the ventilator (ineffective efforts, e.g. third effort, FIG. 1). A more advanced form of non-synchrony is shown in FIG. 2. In this case, the inflation cycle of the ventilator extends over two patient cycles. There are, accordingly, two inspiratory efforts within a single inflation phase and there is an additional ineffective effort during the ventilator's expiratory phase. The arrows in FIG. 2 indicate the location of the extra patient efforts that did not trigger corresponding ventilator cycles.

Non-synchrony between patient and ventilator is extremely common. Leung et al found that, on average, 28% of patient's efforts are ineffective (Leung P, Jubran A, Tobin M J (1997). Comparison of assisted ventilator modes on triggering, patient effort, and dyspnea. Am J Respir Crit Care Med 155:1940-1948). Considering that ineffective efforts are the extreme manifestation of non-synchrony, less severe, yet substantial (e.g. first two breaths, FIG. 1), delays must occur even more frequently. Non-synchrony is believed to cause distress, leading to excessive sedation and sleep disruption, as well as errors in clinical assessment of patients since the respiratory rate of the ventilator can be quite different from that of the patient. Monitoring respiratory rate is a fundamental tool for monitoring critically ill patients on ventilators. Non-synchrony is not only prevalent in intensive care units but is also frequently present in the home setting during sleep when patients are receiving bi-level support for the treatment of sleep apnea or respiratory failure (personal observations). The present invention concerns a novel method and apparatus to, non-invasively, automatically and in real-time, generate a signal that reflects changes in inspiratory effort. Such a signal can then be used, among other things, to determine the true onset ($T_{onset}$) and end ($T_{end}$) of patient's inspiratory efforts. Such method/device can be used simply as a monitor, informing the user of the presence, manifestations and magnitude of non-synchrony. The user can then take appropriate action to reduce the non-synchrony. Alternatively, the method/device can be coupled with the ventilator's cycling mechanisms, whereby onset and end of ventilator cycles are automatically linked to onset and end of patient's efforts, thereby insuring synchrony without intervention by the user.

In current ventilatory assist devices, triggering usually occurs when flow becomes inspiratory (i.e. >0) and exceeds a specified amount, or when airway pressure decreases below the set PEEP (positive end-expiratory pressure) level by a specified amount. Trigger delay has two components. One component is related to ventilator trigger response and sensitivity. Thus, if the response of the ventilator is poor, triggering may not occur immediately when the triggering criteria are reached. Alternatively, the threshold for triggering may be set too high by the user. The component of trigger delay attributable to ventilator response and sensitivity is given by the interval between zero flow crossing (arrow, FIG. 1) and triggering (second vertical line). The response of modern ventilators has improved substantially over the past several years such that it is difficult to effect further improvements in this respect, and this invention does not contemplate any such improvements. This component of trigger delay can, however, still be excessive if the user sets an unnecessarily high threshold. This setting may be because of lack of sufficient expertise, or because there was excessive baseline noise at some point, which necessitated a high threshold to avoid auto-triggering. The threshold then remains high even after disappearance of the noise.

The second component of trigger delay is the time required, beyond the onset of inspiratory effort ($T_{onset}$), for expiratory flow to be reduced to zero (interval between first vertical line and the arrow, FIG. 1). This delay is related to the fact that expiratory resistance is usually high in ventilated patients and expiratory time is frequently too short to allow lung volume to return to FRC (functional residual capacity) before the next effort begins. At $T_{onset}$, therefore, elastic recoil pressure is not zero (DH, dynamic hyperinflation). Inspiratory effort must first increase enough to offset the elastic recoil pressure associated with DH before flow can become inspiratory, and/or before $P_{aw}$ (airway pressure) decreases below PEEP, in order to trigger the ventilator. By identifying the true $T_{onset}$, a capacity that is permitted by current invention, this component of trigger delay (usually the largest component, seen, for example, FIG. 1) can be essentially eliminated.

Cycling-off errors result from the fact that, except with Proportional Assist Ventilation, current ventilator modes do not include any provision that links the end of ventilator cycle to end of the inspiratory effort of the patient. In the most common form of assisted ventilation, Volume Cycled Ventilation, the user sets the duration of the inflation cycle without knowledge of the duration of patient's inspiratory effort. Thus, any agreement between the ends of ventilator and patient inspiratory phases is coincidental. With the second most common form, Pressure Support Ventilation, the inflation phase ends when inspiratory flow decreases below a specified value. Although the time at which this threshold is reached is, to some extent, related to patient effort, it is to the largest extent related to the values of passive resistance and elastance of the patient. In patients in whom the product [resistance/elastance], otherwise known as respiratory time constant, is high, the ventilator cycle may extend well beyond patient effort, while in those with a low time constant the cycle may end before the end of patient's effort (Younes M (1993) Patient-ventilator interaction with pressure-assisted modalities of ventilatory support. Seminars in Respiratory Medicine 14:299-322; Yamada Y, Du H L (2000) Analysis of the mechanisms of expiratory asynchrony in pressure support ventilation: a mathematical approach. J Appl Physiol 88:2143-2150). By providing a signal that reflects changes in inspiratory effort, the current invention makes it possible to determine when effort begins declining, thereby making it possible to synchronize the end of ventilator cycle with end of patient's effort.

In U.S. Pat. No. 6,305,374 B1, an approach is described to identify the onset and end of patient's inspiratory effort during non-invasive bi-level positive pressure ventilation (Bi-PAP). This approach relies exclusively on the pattern of flow waveform to make these identifications. Thus, current values of flow are compared with an estimated value based on projections from preceding flow pattern. If the difference exceeds a preset amount, a phase switch is declared. There is no attempt whatsoever in this method to generate a signal that continuously reflects the pattern of inspiratory effort in real-time throughout the breath. Furthermore, while this method may yield reasonably accurate results in the intended application (treatment of obstructive sleep apnea patients with non-invasive BiPAP), a number of considerations suggest that its use in critically ill, intubated, ventilated patients may not provide accurate results:

1) Implicit to the use of flow as a marker of respiratory muscle pressure output is the assumption that flow pattern reflects changes in alveolar pressure inside patient's lung. This is where respiratory muscle pressure is exerted. This assumption, however, is true only if airway pressure is constant. Since airway pressure is one of the two pressure values that determine flow (flow=(airway pressure-alveolar pressure)/resistance), it is clear that changes in airway pressure can alter flow even if there is no change in respiratory muscle or alveolar pressure. In non-invasive bi-level support, airway pressure, one of the two pressure values that determine flow, is reasonably constant during both inspiration and expiration, even though the absolute level is different in the two phases. If one of the two pressure values is constant during a given phase, it is reasonable to assume that changes in flow during that phase reflect changes in the other pressure, namely alveolar pressure. This condition does not apply in intubated, mechanically ventilated patients. In most modern intensive care ventilators, airway pressure is actively controlled during expiration through adjustments of the PEEP/exhalation valve mechanism. The pattern of such active changes in airway pressure during expiration varies from one ventilator brand to another and in the same ventilator from time to time depending on the state of the PEEP/exhalation valve mechanism. Under these conditions, changes in flow trajectory during expiration cannot be assumed to reflect changes in alveolar pressure trajectory. Likewise, during inspiration airway pressure is far from being constant, regardless of the mode used. Thus, changes in inspiratory flow profile cannot be used to reflect similar changes in alveolar pressure. The use of flow to infer end of effort during the inflation phase is accordingly not plausible.

2) When passive elastance (E) and resistance (R) are constant over the entire tidal volume range, the product R/E, or respiratory time constant, is also constant over the entire period of expiration. Because the time constant governs the pattern of lung emptying, a constant R/E produces a predictable exponential flow pattern in the passive system. With a predictable pattern it is possible to make forward extrapolations, or predictions, for the sake of identifying a deviation from the expected passive behaviour. Such deviation may then be used, with reasonable confidence, to infer the development of an additional active force, such as the onset of inspiratory muscle effort. When E and R are not constant throughout the breath, R/E may change from time to time causing changes in flow trajectory ($\Delta$flow/$\Delta$t) that are not related to muscle pressure. Under these conditions, deviation in $\Delta$flow/$\Delta$t from previous values cannot reliably signify a change in pressure generated by respiratory muscles. Patients with obstructive sleep apnea, the intended population of U.S. Pat. No. 6,305,374 B1, have generally normal lungs; R and E are expected to be constant over the tidal volume range, particularly when expiratory airway pressure is higher than atmospheric (i.e. the usual case when BiPAP is applied). In critically ill, intubated ventilated patients, this is not the case. Resistance is not constant, primarily because these patients are intubated and the resistance of the endotracheal tube is flow-dependent (the higher the flow, the higher the resistance). The relation between resistance and flow varies from one tube to the other. Furthermore, tidal volume in these patients often extends into the volume range where elastance is not constant. Thus, as the lung is emptying, either or both elastance and resistance may be changing, causing changes in respiratory time constant during the same expiration. Under these conditions, changes in flow trajectory need not reflect changes in respiratory muscle pressure. This considerably decreases the sensitivity and specificity of flow pattern as a marker of inspiratory effort.

3) Changes in respiratory muscle pressure ($P_{mus}$) are not exclusively used to change flow. According to the equation of motion, specifically applied to intubated patients:

$$P_{mus} = \text{Volume}*E + \text{Flow}*K_1 + (\text{Flow}*\text{absolute flow}*K_2) - P_{aw} \quad \text{Equation 1}$$

Where, E is passive respiratory system elastance, $K_1$ is the laminar component of passive respiratory system resistance, $K_2$ is the resistance component related to turbulence (mostly in the endotracheal tube or nasal passages), and $P_{aw}$ is airway pressure which is determined by the pressure at the exhalation/PEEP valve ($P_{valve}$), flow and $R_{ex}$, that is resistance of the exhalation tubing ($P_{aw} = P_{valve} - \text{flow}*R_{ex}$). In this equation expiratory flow is negative. When $P_{mus}$ changes, as at $T_{onset}$, the flow trajectory should change. However, a change in flow trajectory also results in changes in volume and $P_{aw}$ trajectories. According to Equation 1, these changes will oppose the change in flow. For example, if expiratory flow decreases at a faster rate, volume decreases at a slower rate than in the absence of $P_{mus}$. At any instant after $T_{onset}$, elastic recoil pressure, which is related to volume, is higher, and this promotes a greater expiratory flow. The same can be said for the effect of changes in flow trajectory on $P_{aw}$ trajectory; a lower expiratory flow decreases $P_{aw}$, which promotes more expiratory flow. How much of the change in $P_{mus}$ is used to change the flow trajectory depends on the magnitude of the opposing forces. In particular, a higher passive elastance and/or a higher $R_{ex}$ tends to reduce the fraction of the change in $P_{mus}$ used to change flow trajectory. Furthermore, for a given $P_{mus}$ expended to change the flow trajectory, the actual change in trajectory is determined by resistance (i.e. $K_1$ and $K_2$). When E, $R_{ex}$, $K_1$ and $K_2$ are all low, a modest change in $dP_{mus}/dt$ results in a sharp change in flow trajectory. As these characteristics become more abnormal, the change in flow trajectory, for a given $dP_{mus}/dt$, progressively is attenuated. FIG. 3 illustrates this in a computer simulation.

In the example of FIG. 3, respiratory muscles were inactive in the first second of expiration (as they usually are). This is represented by $P_{mus}$ of zero (lower panel). At 1.0 sec an inspiratory effort begins. $P_{mus}$ rises at a rate of 10 cmH$_2$O/sec, representative of a normal respiratory drive. The three flow waveforms represent, from below upwards, progressively increasing values of K$_1$, K$_2$, E and R$_{ex}$. The values used in the lowest waveform are those of a patient with normal passive elastance and resistance, intubated with a large endotracheal tube (#9 tube, K$_2$=3), and exhalation tubing with a low resistance (R$_{ex}$=2). The onset of effort results in a sharp change in the flow trajectory that can be readily detected within a very short time after $T_{onset}$.

The middle waveform (FIG. 3) was generated with values representing the average intensive care patient on mechanical ventilation. Both passive K$_1$ and passive E are higher than normal, K$_2$ is that of a #8 endotracheal tube, the most common size used, and the exhalation tubing has a moderate (average) resistance. Note that the change in flow trajectory is considerably less pronounced. An experienced eye, with the benefit of hindsight (i.e. observing the flow waveform for a substantial period after $P_{mus}$ started), may be able to tell that a change in trajectory occurred at 1.0 sec. However, it is not possible to prospectively identify that a trajectory change took place in a timely manner, for the sake of triggering the ventilator. Prospective identification of a trajectory change requires comparison between current and previous $\Delta$flow/$\Delta$t values, or between current flow values and values expected based on forward extrapolation of the preceding flow pattern (e.g. dashed lines, FIG. 3). There is always uncertainty with extrapolation, particularly with non-linear functions where the exact function is not known and, even more so, when the signal is noisy, as the flow signal commonly is (due to cardiac artefacts or secretions). Comparison of current and previous $\Delta$flow/$\Delta$t is also fraught with uncertainties when the rate may change for reasons other than respiratory muscle action (see #1 and #2, above). Thus, a wide difference (trigger threshold) must be specified, between current and projected flow, or between current and previous $\Delta$flow/$\Delta$t, before a trajectory change can be identified with confidence. Otherwise, false triggering will occur frequently. When the change in flow trajectory is small, a longer interval must elapse before the threshold separation is achieved. It can be seen from the middle flow waveform that a conservative flow separation (between actual and projected flow) of 0.2 l/sec would not be reached until after flow became inspiratory. Thus, in the average mechanically ventilated patient the use of flow trajectory to identify $T_{onset}$ is not likely to result in a significant improvement over the current approach of waiting for flow to become inspiratory.

With more severe mechanical abnormalities (top waveform, FIG. 3), the change in flow trajectory is even more subtle. Even an experienced eye, with the benefit of hindsight, cannot distinguish between a true trajectory change and some flow artefact. Clearly, with a much stronger effort a flow trajectory change may be identifiable before flow becomes inspiratory. However, when patients have vigorous inspiratory efforts, there is no significant trigger delay even with current triggering techniques.

In summary, the use of flow to identify respiratory phase transitions is entirely unsuitable for identification of inspiratory to expiratory transitions during mechanical ventilation in critically ill patients (because of the highly variable $P_{aw}$ during inflation), and has poor sensitivity and specificity for identifying expiratory to inspiratory transitions in these patients because of the frequent use of active exhalation valves, the presence of variable time constant during expiration and the often marked abnormalities in elastance and resistance.

An alternative approach has recently been proposed by Younes (U.S. patent application Ser. No. 10/517,384 filed Dec. 10, 2004, the disclosure of which is incorporated herein by reference and corresponding EP application 03 739906 filed Jun. 27, 2003 (WO 2003/002561); Method and Device for monitoring and Improving Patient-Ventilator Interaction). The approach consists of generating a $P_{MUS}$ waveform using improvised values of elastance and resistance. Here, the above equation 1 is used to generate $P_{MUS}$ but, instead of using real resistance (K1) and elastance (E) values, which are difficult to obtain in spontaneously breathing patients, improvised values are used which simply result in the generated $P_{MUS}$ waveform having the shape characteristics of normally occurring $P_{MUS}$ waveforms, namely an approximately flat baseline during expiration and a ramp-like rising phase in the inspiratory phase. The surrogate values for elastance and resistance are assigned herein, the terms $K_V$ and $K_F$ to distinguish them from the real values. Once such an improvised $P_{MUS}$ signal is generated, it is possible to easily identify the onsets and ends of inspiratory efforts for the sake of triggering and cycling-off ventilators. Because the $P_{MUS}$ generated by these improvised resistance and elastance values is not a real $P_{MUS}$ signal, the value generated by the current approach is referred herein to simply as Signal.

The above invention described by Younes proposes the use of a default value for $K_F$ and adjusting the $K_V$ value to result in a flat baseline during expiration. Alternatively, a default value for $K_V$ is used while the $K_F$ value is adjusted to result in a flat baseline during expiration. The preferred embodiments in this earlier Younes patent application employ a fixed value for one of the two variables while adjusting the value of the other variable manually with visual feedback from a monitor. Although the specification suggests that appropriate values for $K_V$ and $K_F$ may be selected automatically using appropriate software, the specification does not teach any approach for doing that and it is evident that such software would have to be sufficiently sophisticated to replace the complex functions executed by the eye-brain combination in humans.

The present invention proposes new methods and apparatus to supplement the approach proposed by Younes. These improvements relate to methods for automatically (as opposed to manually) determining the values of $K_F$ and $K_V$ required for generating a physiologically appropriate Signal waveform from which information about onsets and ends of inspiratory efforts can be derived. Specifically, these methods employ complex algorithms to distinguish between true baseline and noise values during expiration, a task that can be readily done by the human eye, but is very difficult to translate into computer instructions.

Because these new methods/device are intended to work with, and represent an improvement over, the original Younes approach the latter approach will be described in some detail in the detailed description of the invention, below.

SUMMARY OF INVENTION

In accordance with one aspect of the present invention, there is provided a method for generating a signal that mirrors changes in the level of effort exerted by respiratory muscles of patients on mechanical ventilatory support, comprising monitoring of airway pressure ($P_{aw}$), rate of gas flow (F), and volume of gas flow (V) of the patient; storing $P_{aw}$, F and V data collected in computer memory;

generating a composite pressure signal (Signal) from:

$$\text{Signal} = \text{current } V^* K_V + \text{current } F^* K_F - \text{current } P_{aw},$$

wherein, $K_F$ is a coefficient that converts flow into equivalent resistive pressure units and $K_F$ is calculated from elapsed data and selected to minimize step changes in calculated Signal at the time of ventilator triggering and/or cycling-off, and $K_V$ is a coefficient that converts volume into equivalent elastic pressure units and $K_V$ is determined from elapsed data in a number of steps comprising:

scanning of F or $P_{aw}$ information, and/or the time derivative thereof, during the exhalation phase of elapsed breaths and identifying instances where the trajectory of either variable (i.e. F or $P_{aw}$) transiently reverses direction during said exhalation phase (transients);

selecting two or more points within the exhalation phase that are at specified safe distances away from identified transients, and calculating the value of $K_V$ required to force the values of Signal calculated at said selected points in elapsed breaths to be equal, or nearly equal, when said selected value of $K_F$ is used as the flow coefficient.

The term $F*K_F$ may be replaced by other functions that allow for non-linear relation between flow and the resistive pressure units. In particular, $F*K_F$ may be replaced by $[F*K_{F1}+(F*$ absolute $F*K_{F2})]$ wherein $K_{F2}$ is a constant and $K_{F1}$ is calculated from elapsed data and selected to minimize step changes in calculated Signal at the time of ventilator triggering and/or cycling off. $K_{F2}$ may be assigned a value corresponding to the $K_2$ constant of an endotracheal tube in place in the patient.

The values of $K_V$, $K_F$, $K_{F1}$ and/or $K_{F2}$ may be adjusted to result in a specific slope as Signal during part or all of the expiratory phase.

In addition, default values of $K_F$ or $K_{F1}$, depending on the equation, may be used to determine Signal. Alternatively, the $K_F$ or $K_{F1}$ value, depending on the equation used, is a known or estimated value of patient's respiratory system resistance. The $K_V$ value used may be a known or estimated value of patient's respiratory system elastance.

Alternatively, a default value of $K_V$ may be used while the value of $K_{F1}$ required to obtain the desired baseline Signal trajectory is obtained through the same steps as specified above to estimate the required $K_V$. In addition, the $K_V$ value used may be a known or estimated value of patient's respiratory system elastance.

In the equation for determining Signal, the term $V*K_V$ may be replaced by another term that allows for a non-linear relation between volume and equivalent elastic pressure units. The non-linear function may be of the form $[fV*K_V]$, wherein $f$ is a specified mathematical function to be applied to the volume data, or $[V*$ variable $K_V]$ and the value of $K_V$ is a function of volume $[K_V=fF_V]$, wherein $f$ is a specified mathematical function and the specified function (f) is derived from the $P_{aw}$, F and V data measured at the selected two or more points within the exhalation phase.

The detailed transients may be classified into a number of types by reference to specific criteria of the type. The safe distances of selection of the two or more points may be set according to the transient type.

The $K_F$ required to minimize step changes in Signal may be calculated both at the time of ventilation triggering and time of cycling-off and, if differences exist between the two determinations, one or the other is chosen based on pre-specified criteria. In this embodiment, if differences exist between the two determinations, then a simple or weighted average value is obtained for use in calculating Signal.

The generated Signal may be further processed to identify the onset of the rising phase of Signal ($T_{ONSET}$) and/or onset of the declining phase of Signal ($T_{END}$). In this procedure, the identification of $T_{ONSET}$ may be precluded for a specified period in the exhalation phase of the ventilator ($T_{ONSET}$ Window Delay) and/or the identification of $T_{END}$ is precluded for a specific period in the inflation phase of the ventilator ($T_{END}$ Window Delay). A minimum value for $T_{ONSET}$ Window Delay may be specified, preferably as a function of patient's respiratory rate. Similarly, a minimum value for $T_{END}$ Window Delay may be specified, preferably as a function of patient's respiratory rate. The generated $T_{ONSET}$ and/or $T_{END}$ values preferably was used to effect triggering and/or cycling-off of ventilator cycles.

The generated Signal may be further processed to obtain information about patient-ventilator interaction and the information may be communicated to a user through display on a monitor or by other forms of communication. The information may include, but is not limited to, at least one of display of the Signal itself, $T_{ONSET}$ and $T_{END}$ mirrors, trigger delay, cycling-off delay, patient's respiratory rate and number or rate of ineffective efforts.

The calculated value of $K_F$ and/or $K_V$ also may be communicated to the user through display on a monitor or by other forms of communication. This communicated information may be accompanied by narrative/commentary providing interpretation of the findings and/or suggestions for ventilator adjustment that might improve patient-ventilator interaction.

In accordance with another aspect to the invention, there is provided a device for generating a signal that mirrors changes in the level of effort exerted by respiratory muscles of patients on mechanical ventilatory support (Signal), comprising sensors and associated circuitry for obtaining information regarding airway pressure ($P_{aw}$), rate of gas flow (F), and volume of gas flow (V) of such a patient; computer that executes the following functions:

storing collected $P_{aw}$, F and V data in computer memory;
calculating a composite pressure signal (Signal) from:

$$\text{Signal=current }V*K_V+\text{current }F*K_F-\text{current }P_{aw},$$

wherein, $K_F$ is a coefficient that converts flow into equivalent resistive pressure units and $K_F$ is calculated from elapsed breath data using algorithms that calculate the $K_F$ value required to minimize step changes in calculated Signal at the time of ventilator triggering and/or cycling-off, and $K_V$ is a coefficient that converts volume into equivalent elastic pressure units and $K_V$ is calculated from elapsed breath data in a number of steps comprising the following functions:

scanning of stored flow or $P_{aw}$ information, and/or the time derivative thereof, during the exhalation phase of elapsed breaths and identifying instances where the trajectory of either variable (i.e. F or $P_{aw}$) transiently reverses direction during said exhalation phase (transients);

selection of two or more points within the exhalation phase that are at specified safe distances away from identified transients, and calculation functions to determine the value of $K_V$ required to force the values of Signal calculated at said selected points in elapsed breaths to be equal, or nearly equal, when said selected value of $K_F$ is used as the flow coefficient The subsidiary features of the method described above may have corresponding apparatus features in the device of the invention.

DETAILED DESCRIPTION OF THE INVENTION

Figure 1:
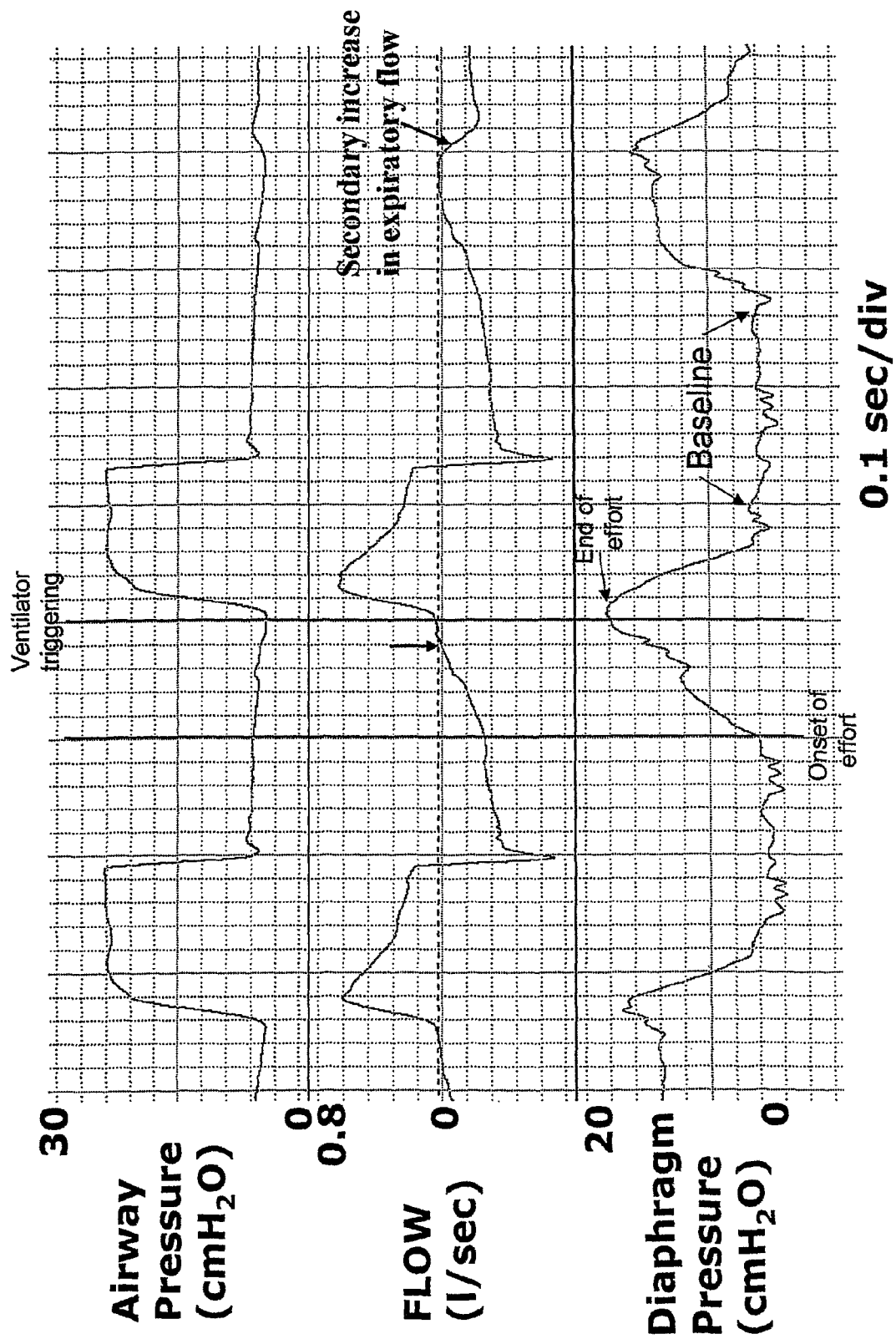
FIG. 1 contains traces of airway pressure, flow and diaphragm pressure for a patient on mechanical ventilation.

The Younes approach contemplates novel methods and devices for specific and timely identification of respiratory phase transitions within the patient for use in monitoring patient-ventilator interaction or to effect switching of ventilator cycles. These methods/devices represent a progression in complexity that address the problems inherent in the prior art ventilation procedures described above.

In the simplest of these methods, a Signal is generated (Signal X) that incorporates changes in both the flow and airway pressure ($P_{aw}$) information. Thus, $$\text{Signal } X = (\text{Flow} * K_f) - P_{aw} \qquad \text{Equation 2,}$$

where, $K_f$ is a constant that converts flow to pressure. $K_f$ may be an estimated or assumed value of patient's resistance (including endotracheal tube). There are two advantages to this approach over the use of flow alone: First, the Signal becomes relatively immune to changes in flow trajectory produced via changes in pressure at the exhalation/PEEP valve mechanism (#1 in Background above). Thus, if pressure at the exhalation/PEEP valve increased near the end of expiration (to maintain PEEP), flow will decrease at a faster rate. Without the $P_{aw}$ component, this effect may appear as an inspiratory effort. With inclusion of $P_{aw}$ in the signal, changes in flow and $P_{aw}$ tend to cancel out. The extent to which this compensation is complete depends on how close $K_f$ is to actual patient resistance. In the absence of a known value, a default value may be used, for example 15 cmH$_2$O/l/sec, representing average resistance (including ET tube) in critically ill, mechanically ventilated patients. With such a default value, correction is not perfect, but the signal is more specific (than flow) in reflecting $T_{onset}$. Second, by including $P_{aw}$ in the signal, the signal incorporates that component of $P_{mus}$ that was dissipated against $R_{ex}$ (see #3 in Background). For example, if $P_{aw}$ decreases at $T_{onset}$ (because of the lower expiratory flow), this decrease is summed with the component related to flow, resulting in a sharper change in Signal trajectory. With this approach, however, Signal baseline prior to inspiratory effort is not flat, but, as in the case of flow, rises in a non-linear fashion. Forward extrapolation continues to be required to identify phase transition. Thus, the uncertainty associated with forward extrapolation is not eliminated but the change in signal trajectory is sharper, resulting in a more timely detection of $T_{onset}$ for the same selected detection threshold (i.e. difference between actual and predicted Signal required for identification). Furthermore, this approach continues to be unsuitable for detection of inspiration to expiration transitions ($T_{end}$).

A further improvement is achieved by incorporating a component related to volume in the Signal (Signal Y). Thus:

$$\text{Signal } Y = \text{Volume} * K_v + \text{Flow} * K_f - P_{aw} \qquad \text{Equation 3,}$$

where, $K_v$ is a factor that converts volume to pressure. With this treatment, the increase in the flow term during expiration (note that flow is negative) is offset by the decrease in the volume term. This tends to linearize, and decrease the slope of (flatten) the Signal in the interval prior to $T_{onset}$, reducing the uncertainty associated with extrapolation, while the change in trajectory at $T_{onset}$ is rendered more acute on account of incorporating representation of all actions resulting from the change in $P_{mus}$ (see #3 in Background). In the best case scenario, where $K_v$ is identical to passive elastance, $K_f$ is identical to passive resistance, and there are no non-linearities in the passive pressure-flow and pressure-volume relations, Signal Y would be identical to the actual $P_{mus}$ waveform, with a flat baseline and a crisp rising phase at $T_{onset}$ (i.e. as in the $P_{mus}$ panel of FIG. 3). Under these conditions, extrapolation is unnecessary, and phase transition is identified when Signal Y exceeds a set threshold above the baseline value, to account for random baseline noise. Unfortunately, however, precise determination of actual passive properties during assisted ventilation is impossible, and there are non-linearities in the pressure-flow and pressure-volume relations. These result in some instability in baseline, necessitating the use of extrapolation. It may be expected, however, that the transition from baseline to active inspiration will be crisper after including a volume component (see below).

A further improvement is achieved by allowing for non-linearity in the pressure-flow relation. In intubated patients, the non-linear element is almost exclusively due to endotracheal tube characteristics. In patients on non-invasive support non-linear behaviour is related to the pressure-flow characteristics of the nose. Thus, in either case, it is desirable to allow for non-linear relation between flow-related (i.e. resistive) pressure losses and flow. Thus, a suitable alternate approach is to partition the flow component in two parts, one related to the endotracheal tube or nasal passages and the other related to a laminar component of resistance ($K_f$). Such Signal is referred to as Signal Z. Thus:

$$\text{Signal } Z = \text{Volume} * K_v + \text{Flow} * K_f + (\text{Flow} * \text{absolute flow} * K_{f2}) - P_{aw} \quad \text{Equation 4,}$$

where $K_{f2}$ may be the commercially available $K_2$ value of the endotracheal tube in place or an estimate of the $K_2$ value of nasal passages. This treatment essentially eliminates any artifactual baseline instability related to non-linear pressure-flow behaviour, further reducing the need for extrapolation and enhancing the crispness of the transition. It should be pointed out that the above approach of replacing [flow*$K_F$] by [flow*$K_{F1}$+(Flow*absolute flow*$K_{F2}$)] is only one of many possible approaches to allow for non-linear behavior between flow and pressure. Other non-linear functions, for example exponential or power function, may be used and provide equally satisfactory solutions in the intended applications. For example, one may choose instead to have $K_{F1}$ increase in a specified way as a function of flow [$K_{F1}$=flow*K] where K is a default value or a value that is determined from analysis of pressure and flow data. Other possible functions, e.g. $K_{F1}$ being an exponential or power function of flow, may be used. Alternatively, $K_{F1}$ may remain as a constant but flow itself is modified according to a specified function. For example, the term [flow*$K_{F1}$] is replaced with [$f$flow*$K_{F1}$] where $K_{F1}$ is a constant and $f$ is an appropriate function of flow. In all these alternative approaches, the appropriate function to be used may be empirically specified or be determined by use of appropriate regression equations to fit the relation between pressure and flow obtained independently in the patient. Thus, although in the preferred embodiment non-linear behavior between flow and pressure is modeled as in equation 4 [resistive pressure=Flow*$K_{F1}$+(Flow*absolute flow*$K_{F2}$)], other functions are possible and their use is within the scope of the present invention.

As indicated earlier, precise estimates of E and $K_1$ are impossible to obtain during assisted ventilation. Passive E and R (including $K_1$) may be available from earlier determinations in which the patient was made passive. These values may be different from the current values, either because the ventilation conditions under which measurements were made were different, or true E and R (i.e. $K_1$) may have changed in the interim. Some techniques can be used to estimate E and R during conventional assisted ventilation, but these are not very reliable. An important issue, therefore, is the impact of differences between the $K_v$ and real E, and between $K_f$ and real resistance, on the baseline of the generated signals and on the sharpness of the transition.

Figure 3:
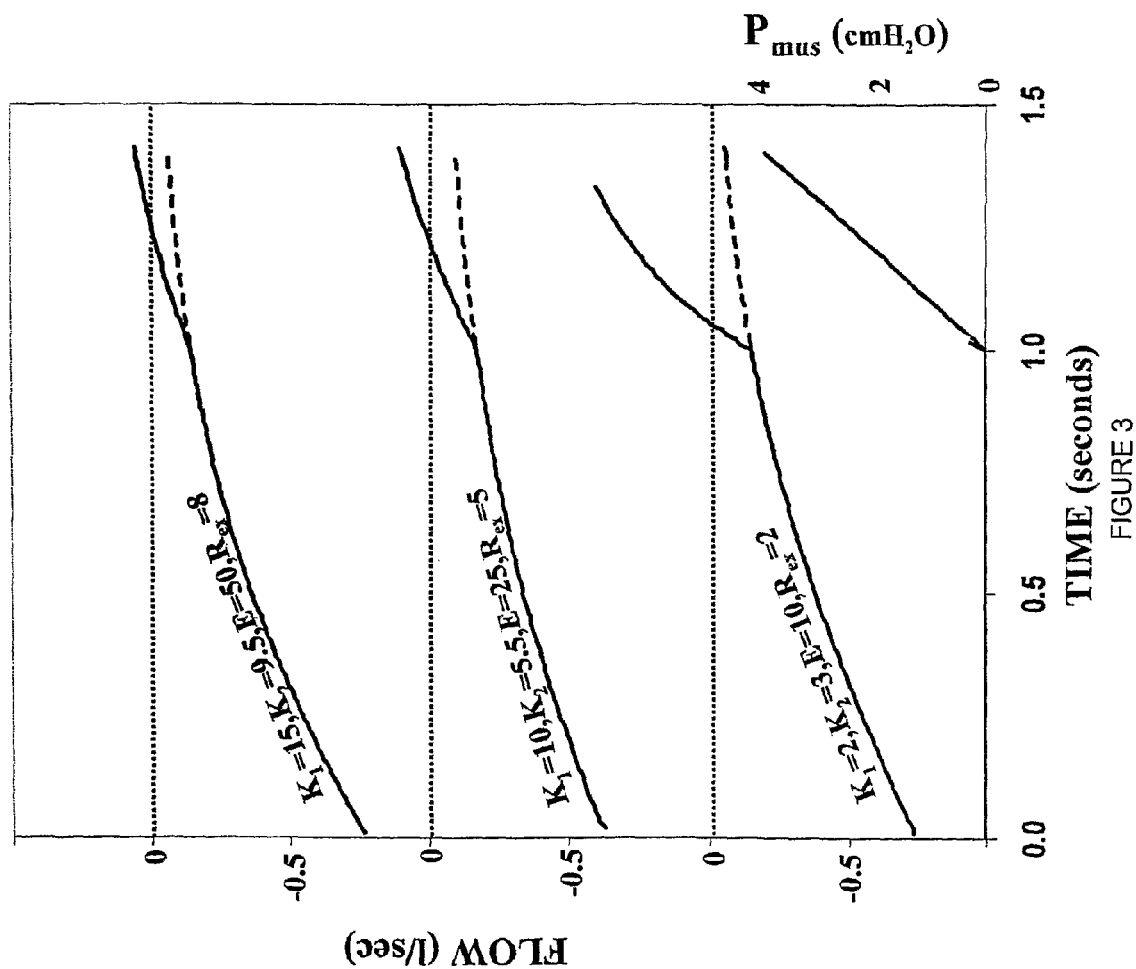
FIG. 3 is a graphical representation of the effect of variation in certain parameters on change in trajectory of flow upon start of inspiration.
Figure 4:
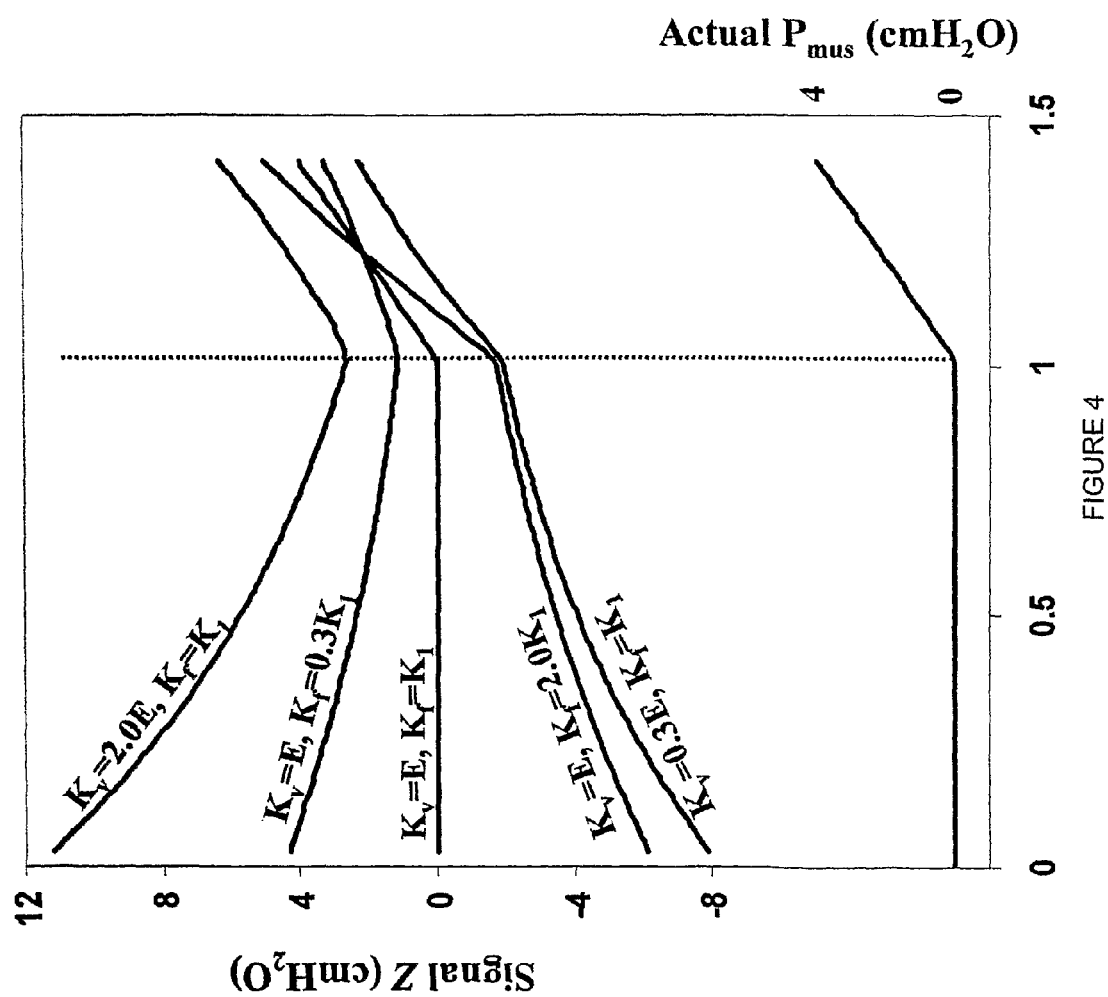
FIG. 4 is a graphical representation of the effect of variation in certain parameters on change in trajectory of composite pressure Signal Z upon start of inspiration.

In FIG. 4, the same $P_{mus}$ waveform shown at the bottom of FIG. 3 was used to generate flow, volume and $P_{aw}$ waveforms using values representative of the average patient ($K_1$=10, $K_2$=5.5, E=25, $R_{ex}$=5, similar to the values used to generate the middle flow panel of FIG. 3). Signal Z was then generated from the resulting flow, volume and $P_{aw}$ waveforms using inaccurate values of $K_v$ and $K_f$ (i.e. $K_v$ different from real E and $K_f$ different from true $K_1$). Simulations were made with errors in either direction (over- or underestimation) of a magnitude that reflects reasonable outside limits of such errors in practice (i.e. E and $K_1$ overestimated by 100% or underestimated by 70%).

As may be expected, when there are no errors (i.e. $K_v$=E and $K_f$=K1, middle line, FIG. 4), Signal Z is identical to the actual $P_{mus}$ waveform. However, when there are differences between assumed values and actual values, the baseline, prior to $T_{onset}$, is neither flat nor linear. When $K_v$ is >E, or $K_f$ is <$K_1$ (upper two lines), baseline is sloping down. Under these conditions, there is a qualitative change in direction of Signal Z at $T_{onset}$ of effort. Such a directional change can be easily detected (e.g. by differentiating Signal Z and looking for the point at which the differentiated signal becomes positive). However, when $K_v$ is <E, or $K_f$ is >$K_1$ (bottom two lines, FIG. 4), baseline is sloping up and $T_{onset}$ is evident as a change in slope; a quantitative, as opposed to the qualitative, difference observed with the opposite errors. To identify inspiratory effort under these conditions, as in the case of flow (FIG. 3), requires forward projection or extrapolation with the attendant increase in uncertainty and the necessity to increase trigger threshold. It should be noted, however, that with this approach (i.e. using Signal Z (or Y) as opposed to flow) the change in trajectory is much sharper than in the case of flow (middle line, FIG. 3), making it possible to identify inspiratory effort sooner. It should also be noted that the upward slope of the signal, once effort begins, is related to the $K_f$ value, being higher when $K_f$ is higher than $K_1$, and vice versa.

It follows that the use of known values of E and $K_1$, obtained from previous direct measurement, offers advantages over the use of flow. However, under some conditions (i.e. baseline sloping upward) extrapolation techniques (or comparisons between current and previous rates of Signal change) are required, and this may delay detection of phase transition.

A further novel aspect of the Younes invention is to completely ignore patient values of E and $K_1$ and to simply select empiric values of $K_v$ and $K_f$ that result in a flat or slightly downward sloping baseline in the latter part of expiration. It is clear from FIG. 4 that, with respect to baseline pattern (i.e. pattern prior to inspiratory effort), errors can be made to cancel out. Thus, overestimation of E and overestimation of $K_1$ produce opposite errors. If empiric values of $K_v$ and $K_f$, that may have no bearing on actual values, are used, the baseline may be sloping up or down depending on the nature and magnitude of errors. Even though one cannot tell which value is in error, or by how much, it is always possible to obtain a flat baseline by adjusting either $K_f$ or $K_v$. For example, if using the empiric values results in an upward sloping baseline, the baseline can be made flat by increasing the empiric $K_v$ or decreasing the empiric $K_f$. If such adjustments result in a flat baseline but some systematic non-linearities persist, these can be offset by adjustments of the non-linear $K_{f2}$ term, if Signal Z is used, resulting in a flat, and linear baseline. Under such conditions, identification of $T_{onset}$ presents little difficulty. A particularly suitable approach for generating Signal Z is to use a default $K_f$ value of 10 cmH$_2$O/l/sec (15 if Signal Y is used) and adjust $K_v$ to obtain a flat Signal baseline. Alternatively, a default $K_v$ value (e.g. 25 cmH$_2$O/l, representing average elastance in ICU patients) is used and $K_f$ is adjusted to obtain a flat Signal baseline. The former approach was found preferable by the inventor as it guarantees a fairly brisk rate of signal rise at $T_{onset}$. Adjustments of $K_v$ at a set $K_f$, or vice versa, can be implemented by the user employing external inputs for $K_v$ and/or $K_f$ with feedback from a graphic display of the generated Signal (Signal Y or Z). Alternatively, selection of the optimum $K_v$ and $K_f$ values may be done automatically using appropriate software, as in the present invention.

The above approach does not address the possibility of non-linear relation between volume and elastic pressure losses, i.e. $K_v$ is not a constant. When this is present, and it is common in mechanically ventilated patients, the respiratory system is stiffer in the higher part of the tidal range. When $K_v$, which is a constant, is adjusted to produce a flat or slightly decreasing Signal in the latter part of expiration the Signal is not flat in the early part of expiration. In the presence of non-constant elastance (higher elastance at higher volumes) the Signal shows a rising phase in the early part of expiration that continues until volume reaches the range of constant elastance. This artifactual rising phase may cause false identification of a new inspiratory effort. This problem may be averted by "blinding" the $T_{onset}$ detection circuitry to the Signal during the early part of expiration. This can be done, for example, by gating the Signal to the $T_{onset}$ detection circuitry only after a certain delay from onset of expiratory flow ($T_{onset}$ window delay). Alternatively, the $T_{onset}$ detection circuitry may continue to detect $T_{onset}$ during this period but the resulting identification is gated out during this period. Detection of these false triggers can be easily recognized visually by their consistent relation to end of ventilator cycle. The magnitude of the delay (blinding or blanking period) can then be adjusted accordingly. Alternatively, software algorithms can be developed to detect triggering Signals with a consistent relation to end of ventilator cycle and automatically adjusting the width of the window.

Figure 5:
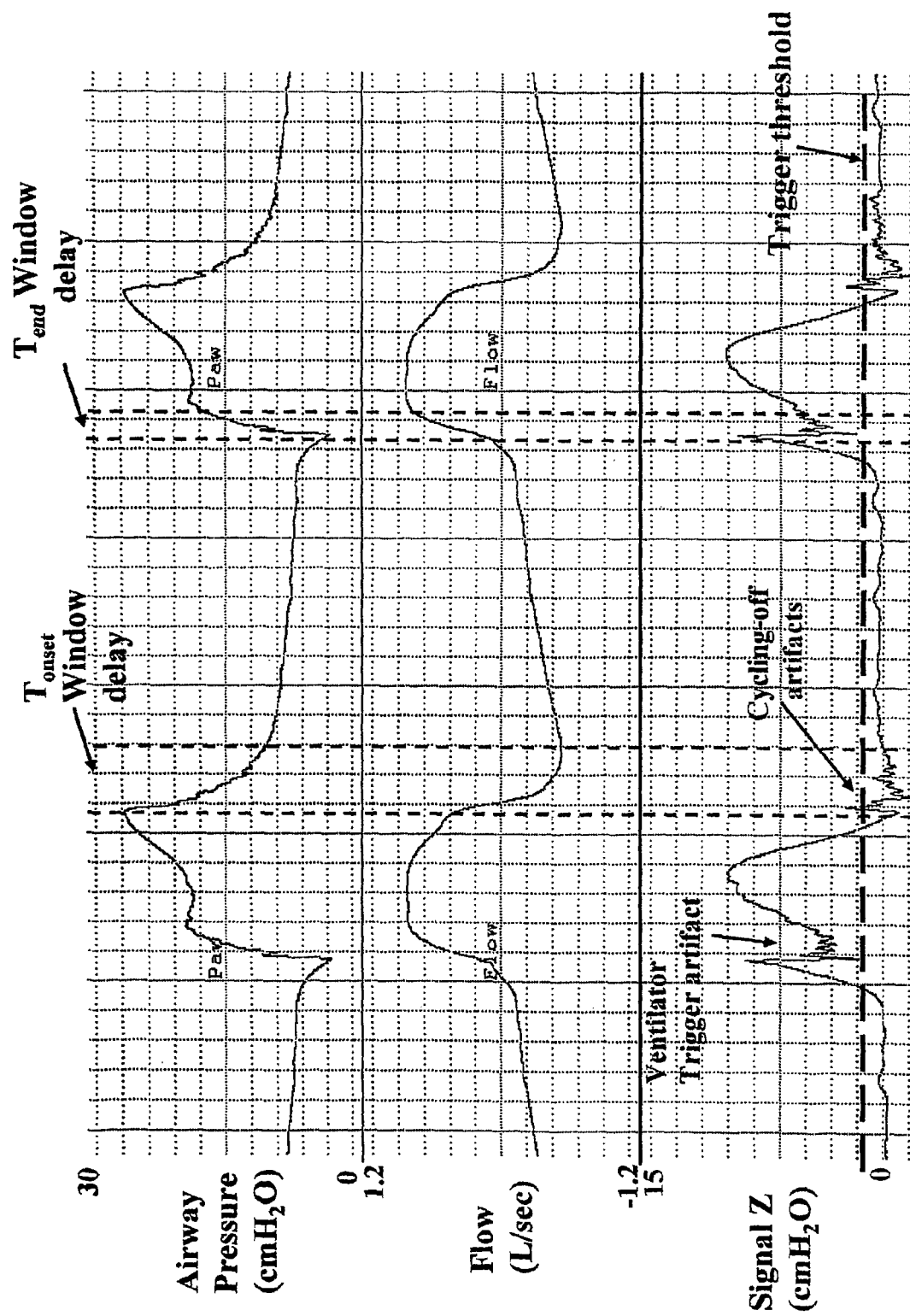
FIG. 5 contains traces of airway pressure, flow and composite pressure Signal Z calculated in accordance with the invention.

The approach of blinding the $T_{onset}$ detection circuitry to the signal over a time zone close to ventilator cycling-off, where flow is changing rapidly, also helps weed out false triggers related to other artifacts that commonly occur in the Signal at this time (see Cycling-off Artifacts, FIG. 5). These are related to acceleration pressure losses, which are difficult to compensate for, or to phase delays between pressure and flow signals, which are common in this setting, among other factors.

An alternative (or complimentary) solution to the issue of non-linear relation between volume and elastic pressure is to use a non-constant value for $K_V$. For example, $K_V$ may itself be a function of volume. A variety of functions may be used. For example, $K_V$ may rise linearly with volume ($K_V$=V*constant). Alternatively, $K_V$ may be constant up to a certain volume and then increase linearly with volume above this level. $K_V$ may also be made to rise exponentially or as a power function of volume above a specified volume. Alternatively, the term $V*K_V$ may be replaced with [$fV*K_V$] where $K_V$ is a constant and f is an appropriate function of volume. The appropriate function may be empirically specified or be determined by use of appropriate regression equations to fit the relation between pressure and volume (see below).

It should be pointed out that the selected values of $K_v$ and $K_f$ may have little to do with actual patient elastance and resistance. These values are simply used to facilitate detection of phase transitions.

Figure 6:
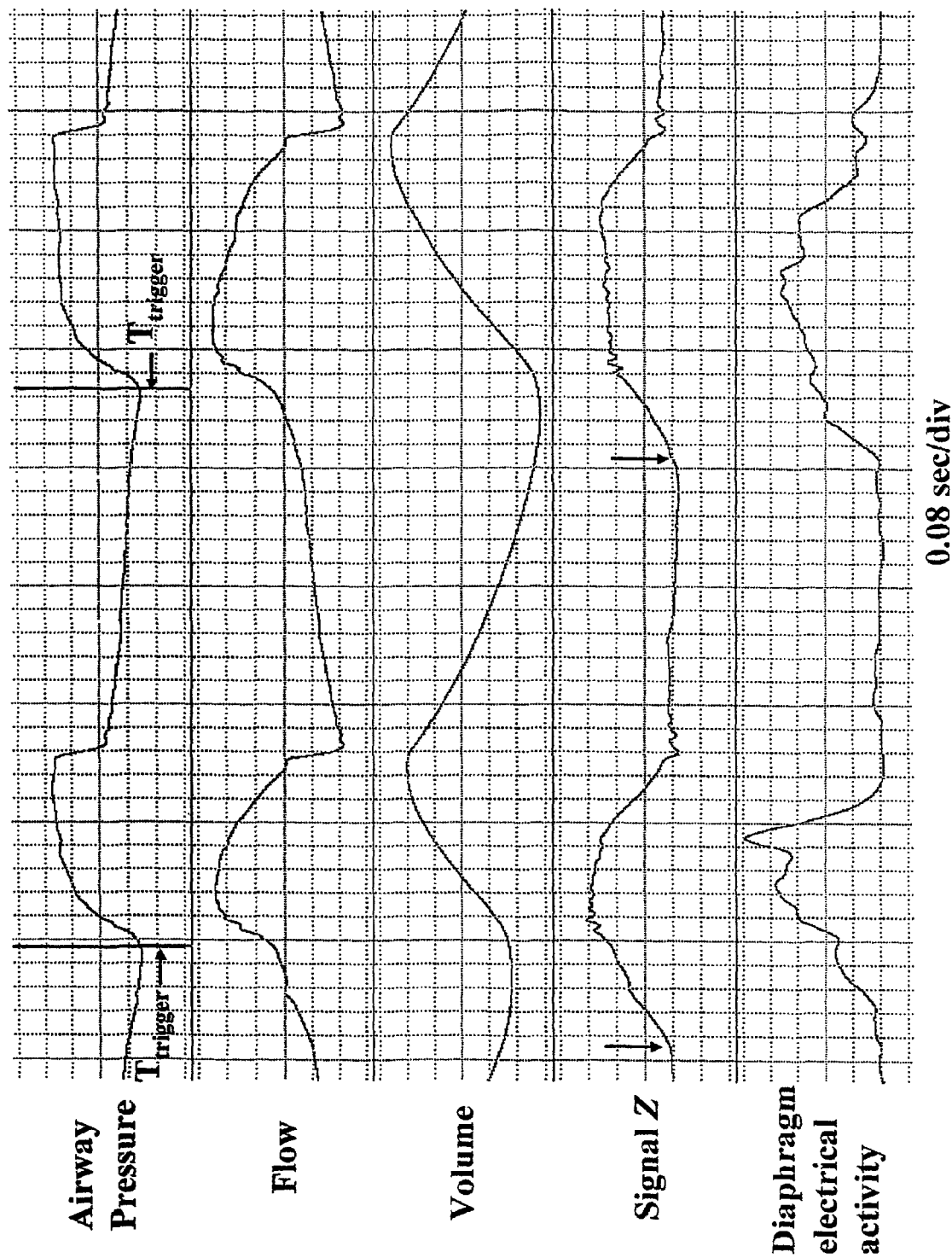
FIG. 6 contains traces of airway pressure, flow, composite pressure Signal Z and diaphragm electrical activity, with the Signal Z tracing being generated from pressure, flow and volume tracings.

FIG. 6 shows an example of Signal Z generated from pressure, flow and volume tracings. The Signal was generated using a default $K_f$ of 10, $K_{f2}$ of 5.5 (ET tube #8) and a $K_v$ of 30.5 selected because it produced a flat baseline in the latter part of expiration. Note the flat baseline of Signal Z in the latter part of expiration. In this patient, diaphragmatic electrical activity was also monitored (lowest tracing), and this reflects the activity of the main inspiratory muscle. Note the excellent agreement between the onset of effort identified from the Signal Z (arrows) and the onset of diaphragm electrical activity. Note also that $T_{onset}$ (arrows) was identified much earlier than the time at which the ventilator triggered with a conventional triggering algorithm ($T_{trigger}$, top channel, FIG. 6).

A number of approaches can be used to identify a change in Signal trajectory indicative of E→I transition ($T_{onset}$). Some of these include:

a) Differentiating the Signal (ΔSignal/Δt) and comparing current values with values obtained earlier. $T_{onset}$ is identified when the difference exceeds a specified amount.

b) Comparing current values of Signal with predicted values obtained from forward projection of previous Signal trajectory. $T_{onset}$ is identified when the difference exceeds a specified amount.

c) Comparing current values of Signal with values obtained earlier. $T_{onset}$ is identified when the difference exceeds a specified amount.

d) Preferred approach: Differentiating the Signal (ΔSignal/Δt) and identifying points where ΔSignal/Δt crosses zero in a positive direction ($t_0(+)$). The change in Signal amplitude, relative to amplitude at the immediately preceding $t_0(+)$, is continuously calculated. $T_{onset}$ is identified when the difference between current value and value at the preceding $t_0(+)$ exceeds a specified amount (threshold). If the difference does not reach threshold by the time ΔSignal/Δt crosses zero in a negative direction ($t_0(-)$), the difference is reset to zero, until the next $t_0(+)$. This approach has the advantage of filtering out slow, random undulations in baseline Signal without altering the relation between Signal and inspiratory effort (which would occur if a simple high pass filter were used). Such slow, random undulations in baseline Signal may be produced, for example, by changes in thoracic blood volume, imperfect compensation for mechanical non-linearities, or random changes in respiratory muscle tone unrelated to phase transitions. The same approach can also be used to estimate the amplitude of higher frequency baseline noise (e.g. due to cardiac artifacts or secretions, see below). Such information can then be used to automatically adjust the threshold for identifying $T_{onset}$.

Regardless of which approach is used to identify $T_{onset}$ (a-d, above, or other approaches), a threshold must be set for the magnitude of change that must be reached for $T_{onset}$ to be declared. Several methods can be used to select such threshold. Some of these include:

i) A fixed threshold is arbitrarily selected. For example, with approach (d), a Signal increase, beyond the latest $t_0(+)$, of 2 $cmH_2O$ may be used under all conditions. Appropriate values may be chosen for other approaches. Although feasible, when a universal threshold is used, the value must be sufficiently high to avoid false auto-triggering under all circumstances. Since noise level varies from patient to patient, and from time to time, such a universal threshold would have to be set to a level that is unnecessarily high under most conditions.

ii) Threshold may be individually selected by the user via external controls. This can be achieved by the user selecting a value that results in minimal auto-triggering. Alternatively, with the help of graphical display of the Signal, the user may adjust the threshold above baseline noise level (e.g. horizontal dashed line, FIG. 5).

iii) Software algorithms can be developed to distinguish noise from efforts and automatically adjust the threshold accordingly.

The preceding account focussed primarily on identification of E→I transitions. However, once $K_v$ and $K_f$ are selected to produce a nearly flat baseline during expiration, the shape of the Signal during inspiration provides a reasonable approximation of the shape of inspiratory muscle output ($P_{mus}$) (for example, see FIG. 6). End of inspiratory effort ($T_{end}$) is normally defined as the point at which inspiratory muscle output rapidly declines from its peak value. To implement this definition, the highest value of Signal Y (or Z) during the inflation phase can be identified, in real time, using any of a number of standard techniques. $T_{end}$ is identified when the Signal decreases below a specified value or a specified fraction of peak value.

At times, the Signal undergoes a transient artifactual reduction soon after ventilator triggering. An extreme example is shown in FIG. 5 (arrow indicating Ventilator Trigger Artifact). It is recognized as an artifact, as opposed to natural end of effort ($T_{end}$), because the Signal resumes rising again. The presence of these artifacts may cause false identification of $T_{end}$. To avoid this, the $T_{end}$ identification circuitry is "blinded" to the Signal for a set period after $T_{trigger}$ (see $T_{end}$ Window Delay, FIG. 5) in the same way the $T_{onset}$ identification circuitry is "blinded" to the Signal soon after ventilator cycling-off. Distinction between artifactual and true $T_{end}$ can be easily made by the consistent occurrence at $T_{trigger}$ and the secondary rise in Signal that characterize false $T_{end}$s. The distinction can be made by the user with the help of a monitor displaying the Signal, or by using software algorithms. The width of the Tend Window delay is adjusted accordingly. Alternatively, the width of the $T_{end}$ Window Delay may be set to insure that the ventilator's inflation phase is not less than an appropriate physiological fraction (e.g. 30%) of the patient's respiratory cycle duration ($T_{TOT}$). For example, if the patient's respiratory rate is 20 (i.e. $T_{TOT}$=60/20 or 3 seconds), a $T_{end}$ Signal may be precluded from cycling off the ventilator until 0.9 second (30% of 3 seconds) had elapsed since $T_{onset}$.

One aspect of the present invention concerns a process to automate the selection of a $K_V$ value that results in a stable Signal baseline during the expiratory phase. The basic approach is to identify periods during the expiratory phase of the ventilator that are free of any evidence of real or artifactual pressure generation by the respiratory muscles. Since, by definition, the remaining periods (effort-free periods) are "passive", Signal values calculated at different points during these effort-free periods should be the same. Thus, by identifying effort-free periods within the ventilator's expiratory phase and sampling pressure, flow and volume at different points within these periods it is possible to calculate the $K_V$ value required to "force" Signal to be the same in between efforts, thereby resulting in a stable Signal baseline. As an example, taking the case where $P_{aw}$, flow and volume were sampled at only two effort-free points (points a and b) during the ventilator's expiratory phase and applying equation 4 at both points one obtains:

Signal $Z_{(a)}$=Volume$_{(a)}$*$K_V$+Flow$_{(a)}$*$K_{F1}$+(Flow$_{(a)}$*abs flow$_{(a)}$*$K_{f2}$)−$P_{aw(a)}$ AND, Signal $Z_{(b)}$=Volume$_{(b)}$*$K_V$+Flow$_{(b)}$*$K_{F1}$+(Flow$_{(b)}$*abs flow$_{(b)}$*$K_{f2}$)−$P_{aw(b)}$ To establish a flat baseline for Signal Z one dictates that Signal $Z_{(a)}$=Signal $Z_{(b)}$. From this, the value of $K_V$ required to obtain a flat baseline between efforts at a given $K_{F1}$ can be derived. Thus:

$K_V$=[($P_{aw(a)}$−$P_{aw(b)}$)−(Flow$_{(a)}$−Flow$_{(b)}$)*$K_{F1}$−((Flow$_{(a)}$*abs flow$_{(a)}$)−(Flow$_{(b)}$*abs flow$_{(b)}$))*$K_{F2}$]/(Volume$_{(a)}$−Volume$_{(b)}$)   Equation 5

It must be emphasized that one need not insist on Signal being identical at the two points of measurement. Under some circumstances, it may be desirable to have Signal baseline sloping upward or downward by specified amounts. To effect this, one dictates that Signal at "a" should be different from Signal at "b" by a specified amount, X, where X may be a constant (e.g. Signal $Z_{(a)}$=Signal $Z_{(b)}$+2) or a function of time difference (dT) between the two points (e.g. Signal $Z_{(a)}$=Signal $Z_{(b)}$+2*dT). Thus, the above approach may be used to produce any desirable slope of Signal baseline, including a flat baseline (zero slope).

It is clear that there are several other possible procedural and mathematical ways by which specified baseline slopes of the composite Signal can be obtained once the effort-free periods have been identified. For example, instead of solving for the required $K_V$ at a given $K_{F1}$, the value of $K_{F1}$ required to obtain a flat baseline between efforts at a given $K_V$ can be derived. Thus:

$K_{F1}$=[($P_{aw(a)}$−$P_{aw(b)}$)−(Volume$_{(a)}$−Volume$_{(b)}$)*$K_V$−((Flow$_{(a)}$*abs flow$_{(a)}$)−(Flow$_{(b)}$*abs flow$_{(b)}$))*$K_{F2}$]/(Flow$_{(a)}$−Flow$_{(b)}$)   Equation 6

In such a case, the $K_V$ value used may be a default constant value (e.g. 25, reflecting the average elastance in ventilated patients, personal observations) or an independently measured elastance value.

Similarly, instead of measuring $P_{aw}$, flow and volume at only two effort-free time points, one may choose to measure these variables at three or more effort-free points and obtain the required value of $K_V$ by regression analysis. One form of regression analysis that is suitable in this case is:

$X=Y \cdot K_V$ where, X values are the numerator values in equation 5 obtained from differences between $P_{aw}$, flow and volume at the different points of sampling and the corresponding values obtained at earlier sampling points, and the Y values are the corresponding volume differences. For example, if samples were obtained at four effort-free points (1 to 4) during the exhalation phase one X,Y set may be obtained from differences between points 1 and 4, another from differences between points 2 and 4, and yet another from differences between points 1 and 3, and so on for a maximum number of X,Y sets of 6. Other types of regression analysis methods can be used to arrive at the best-fit $K_V$ for the effort-free samples.

As indicated earlier, one may choose to use a non-constant $K_V$ to allow for non-linear relation between volume and pressure. To implement such a non-linear behavior, one may use a best-fit non-linear function (e.g. exponential, power ... etc) to fit the X and Y data. Or, one may use other statistical approaches to arrive at a suitable description of the relation between the pressure (numerator product in equation 5) and volume (denominator product in equation 5) data collected during the exhalation. Thus, although the preferred embodiment employs a constant $K_V$, it is to be recognized that the use of non-constant $K_V$ is also feasible and such use is within the scope of the present invention.

Likewise, the same approach can be employed utilizing Equation 3 in place of Equation 4. Thus, the novelty of the present invention is not in how to process the $P_{aw}$, flow and volume data obtained at effort-free points but in the general approach of deriving the required $K_V$ or $K_{F1}$ values by sampling pressure, flow and volume in effort-free periods during exhalation and how to identify these effort-free periods. This will now be discussed in detail.

Figure 7:
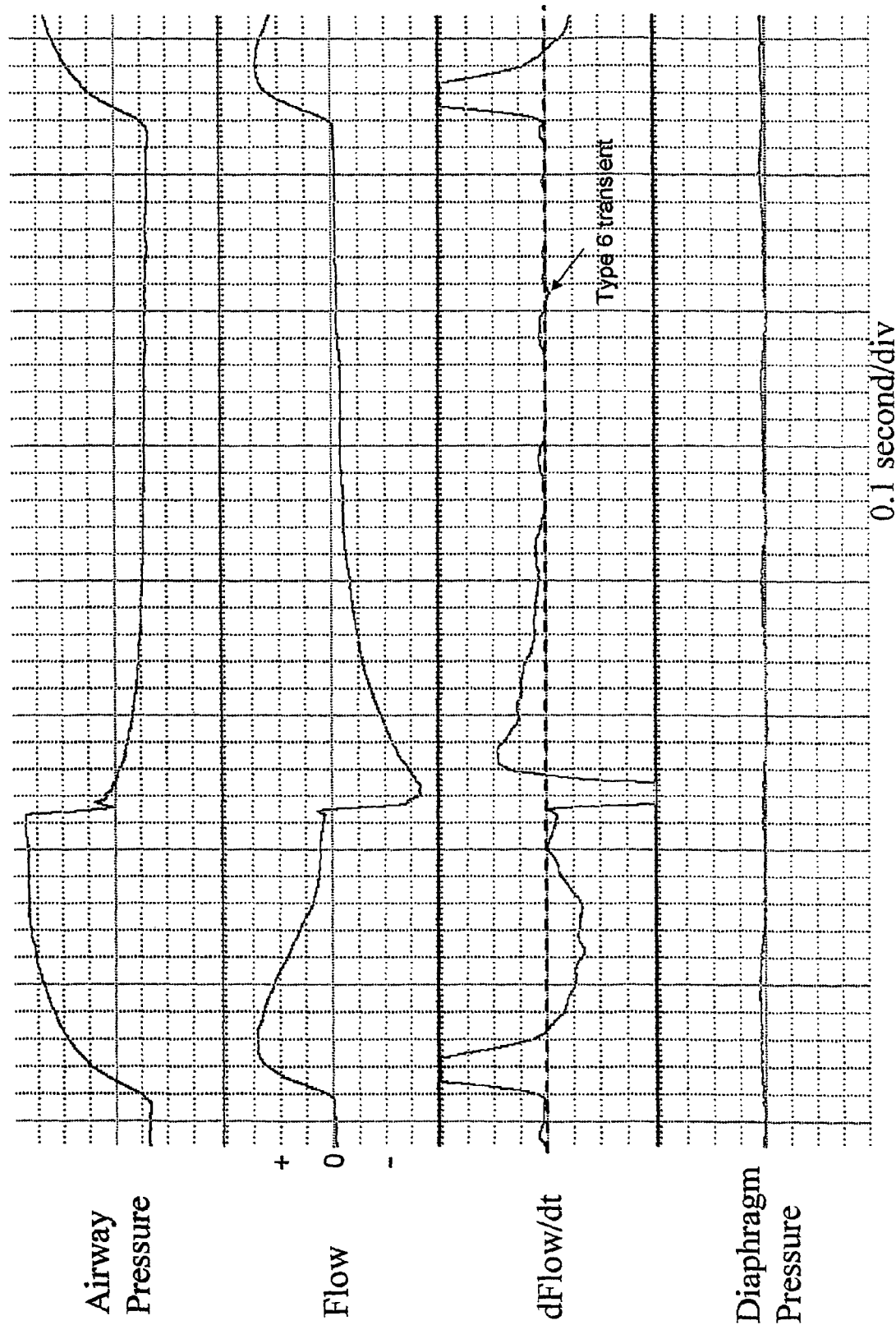
FIG. 7 contains traces of airway pressure, flow, dFlow/dt and diaphragm pressure for passive exhalation respiratory flow.

One aspect of the present invention is a method for identifying effort-free periods that are suitable for sampling $P_{aw}$, flow and volume for the sake of estimating $K_V$. This method is based on the fact that in a totally passive (i.e. effort-free)

exhalation expiratory flow reaches its peak (most negative) value early in the expiratory phase and declines progressively (i.e. becomes less negative) as exhalation continues (FIG. 7). Accordingly, the first derivative of flow (dFlow/dt) is positive throughout the expiratory phase, except for very minor noise artefacts (FIG. 7). The present approach is based on the presumption that occurrence of a significant negative dFlow/dt transient during the ventilator's exhalation phase (i.e. trajectory of expiratory flow changing direction from rising (becoming less negative) to falling (becoming more negative) as exhalation progresses indicates that an event has happened, or is happening, that violates the passive state. Accordingly, sampling of $P_{aw}$, flow and volume should be avoided within an appropriate region in the vicinity of such transients.

Figure 8:
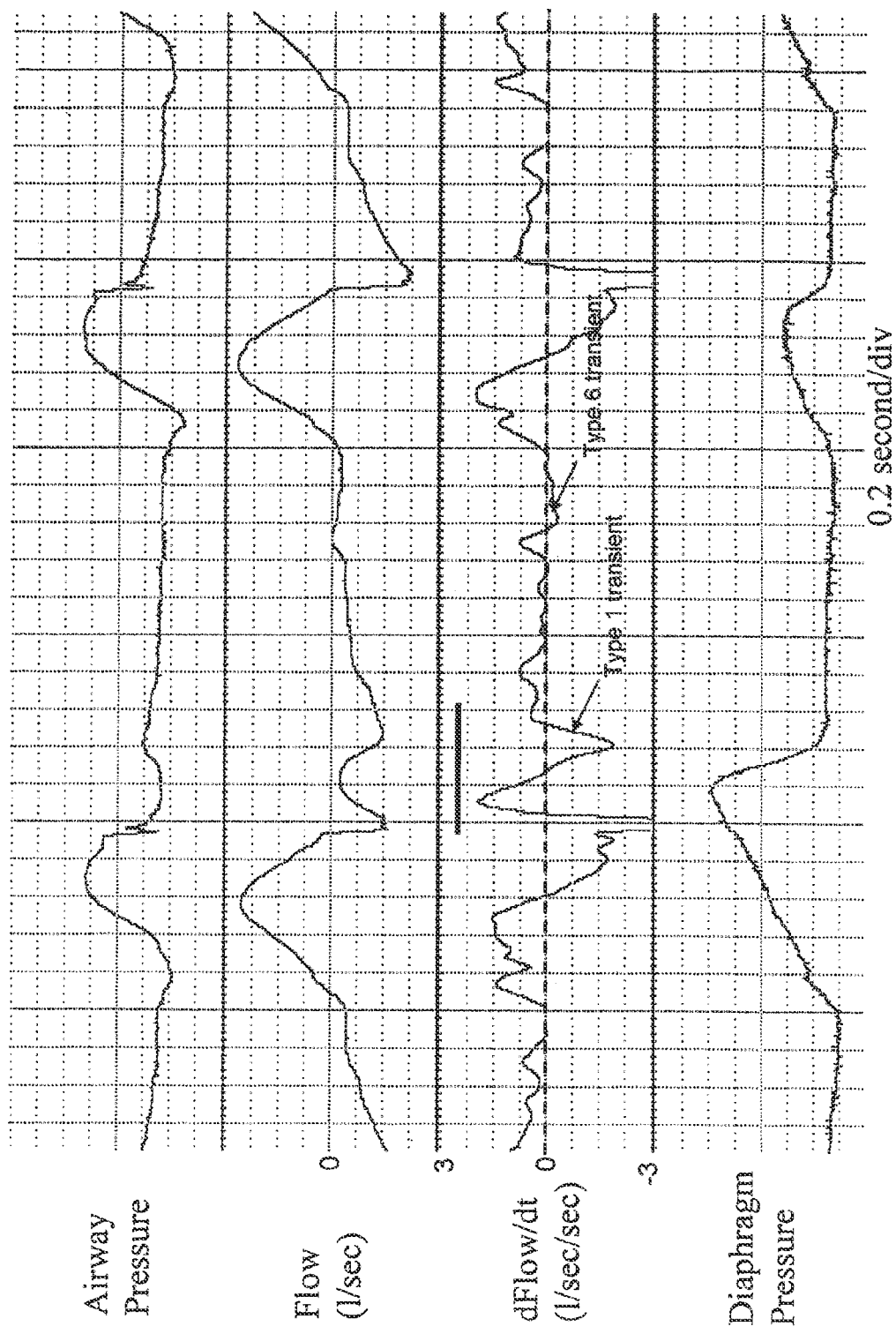
FIGS. 8 to 12 contain traces of airway pressure, flow, dFlow/dt and diaphragm pressure illustrating various type of negative flow transients during the exhalation phase of the ventilator.

There are several types of events that may violate the passive state during the exhalation phase of the ventilator. These are shown in FIGS. 8 to 12. FIG. 8 illustrates the case where the inspiratory effort that triggered a previous ventilator cycle extended beyond the inflation phase into the exhalation phase (type 1 negative flow transient). Here, the ventilator inflation phase terminated before the end of inspiratory effort with the consequence that the decline in inspiratory effort (diaphragm pressure) occurred in the early exhalation phase instead of prior to beginning of exhalation phase (compare with the next breath in FIG. 8). As a result of the withdrawal of a distending force during exhalation, expiratory flow became transiently more, instead of less, negative, resulting in a negative dFlow/dt transient of a substantial amplitude and duration.

Figure 9:
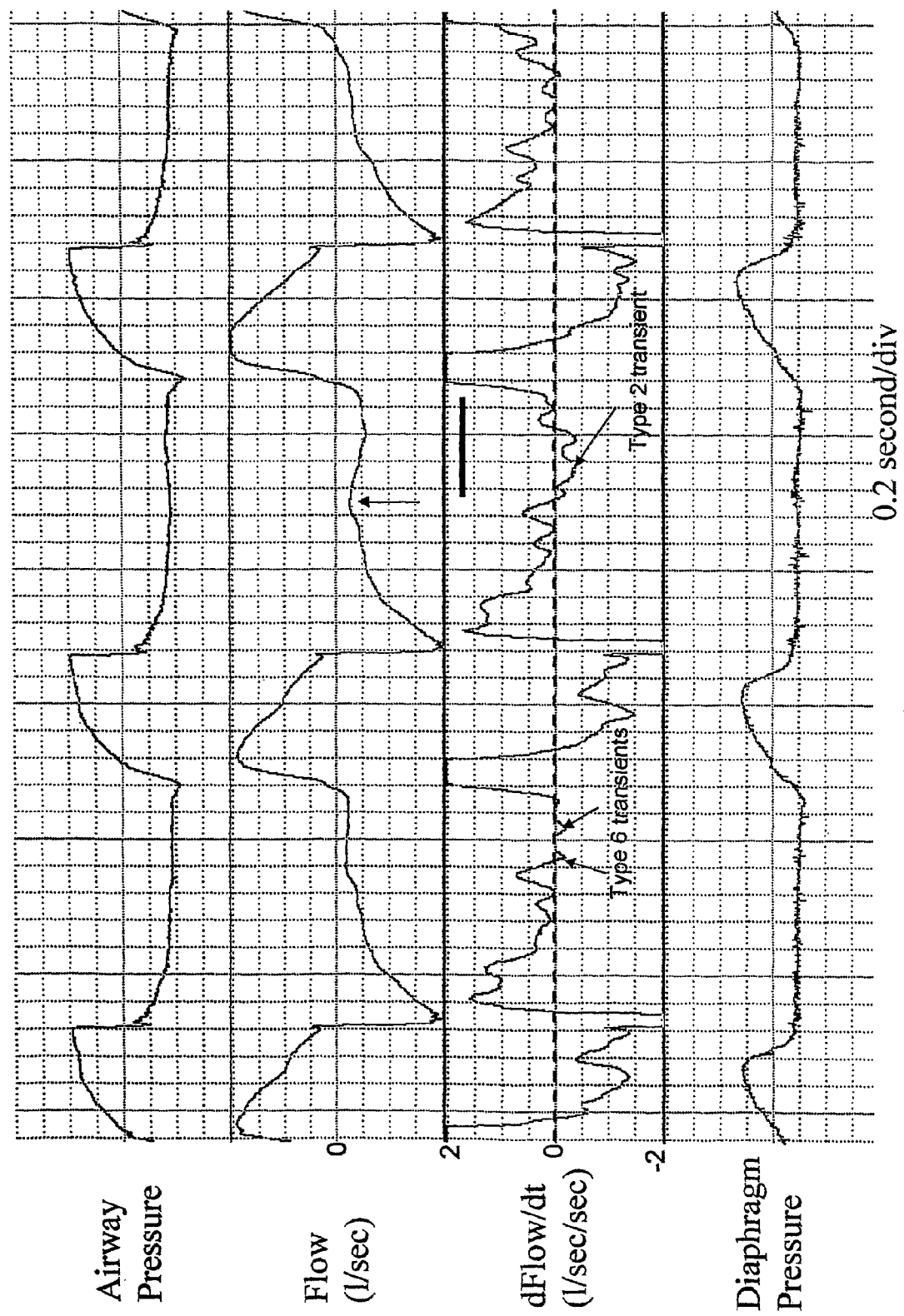

FIG. 9 shows another type of negative flow transient (type 2 transient). Note that expiratory flow increased at the arrow without a preceding inspiratory effort (note that diaphragm pressure was flat prior to onset of the negative flow transient) or a decrease in $P_{aw}$ at the time (in fact $P_{aw}$ increased during the negative dFlow/dt transient, which should have decreased expiratory flow). The only possible explanation for this type of transient is expiratory muscle recruitment.

Figure 10:
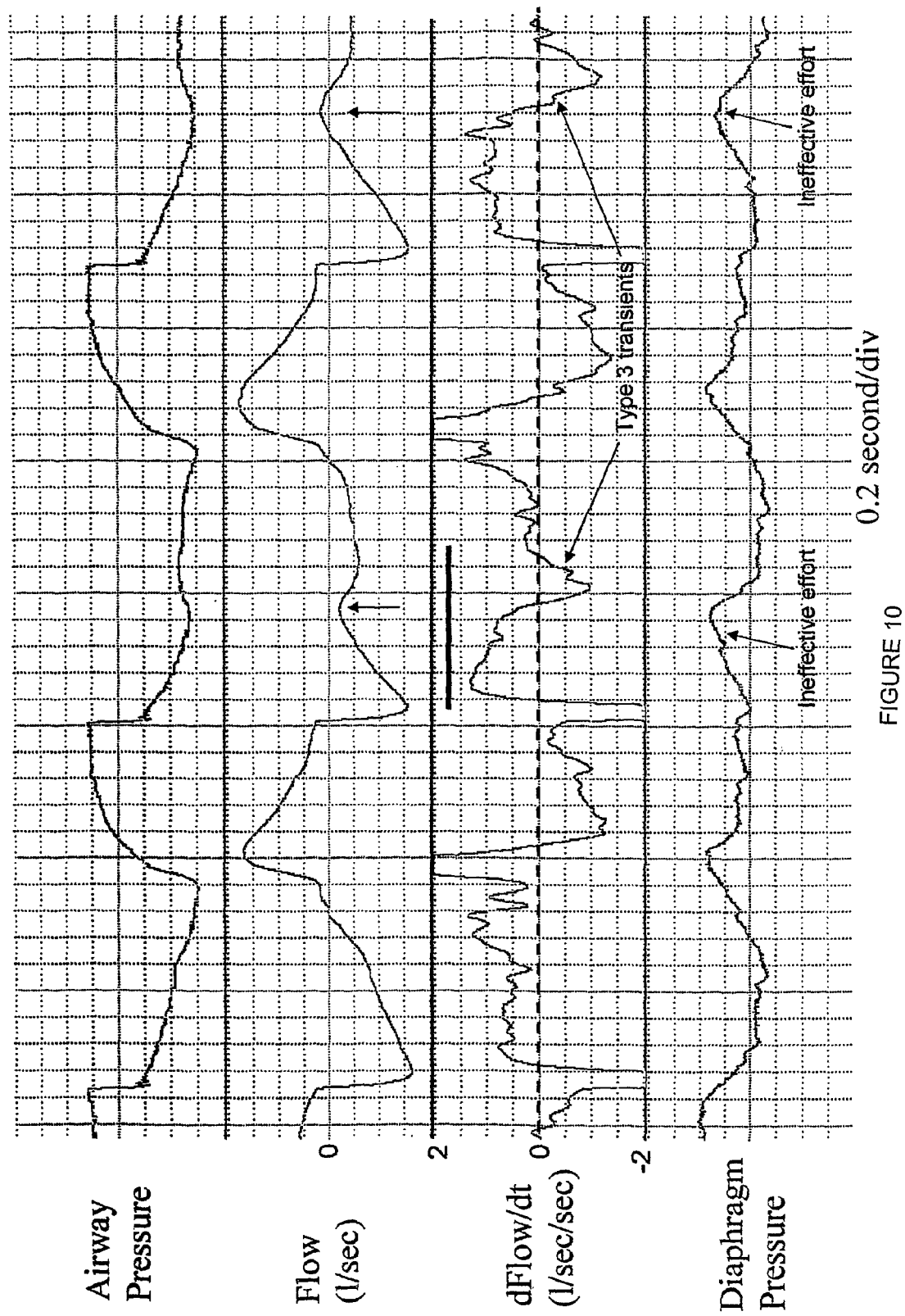

FIG. 10 shows negative flow transients due to ineffective inspiratory efforts (type 3 transient). Here, inspiratory efforts occurred (note the positive deflections in diaphragm pressure) during the ventilator's expiratory phase in the $2^{nd}$ and $3^{rd}$ illustrated breaths. The distending force of the inspiratory effort caused a reduction in expiratory flow but failed to trigger the ventilator (see also FIGS. 1 and 2). As the effort subsided later, the distending pressure decreased, resulting in a secondary increase in expiratory flow.

Figure 11:
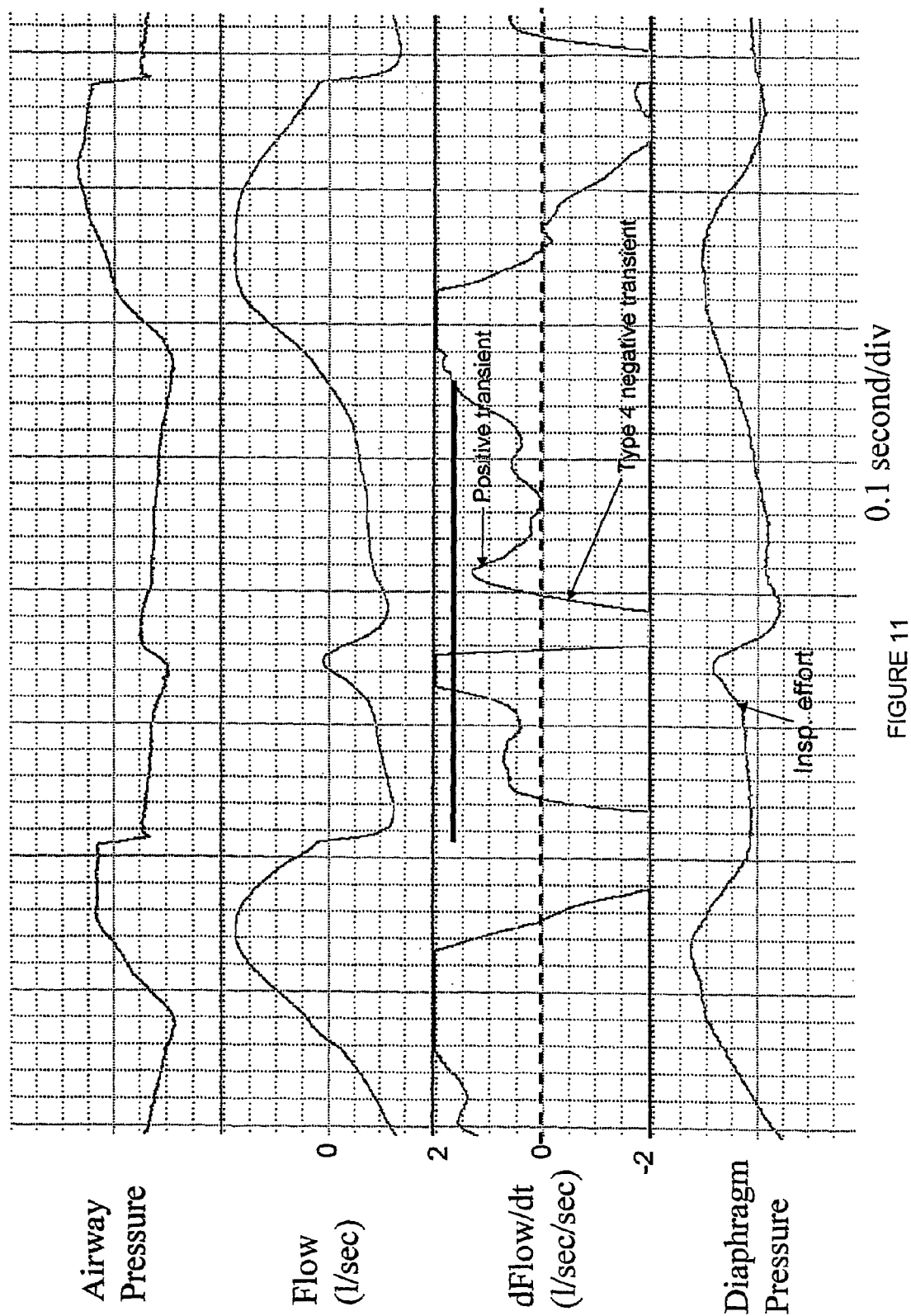

FIG. 11 shows a negative flow transient caused by coughing effort (type 4 flow transients). As in ineffective efforts, the increase in expiratory flow (negative dFlow/dt transient) is preceded by an inspiratory effort (arrow in diaphragm pressure) but, unlike ineffective efforts and other negative transients, dFlow/dt reaches much more negative values (it was −5.2 in the illustrated example) and, characteristically, there is a large positive overshoot in the dFlow/dt signal immediately following the negative transient (cf. FIGS. 8 to 10).

Figure 12:
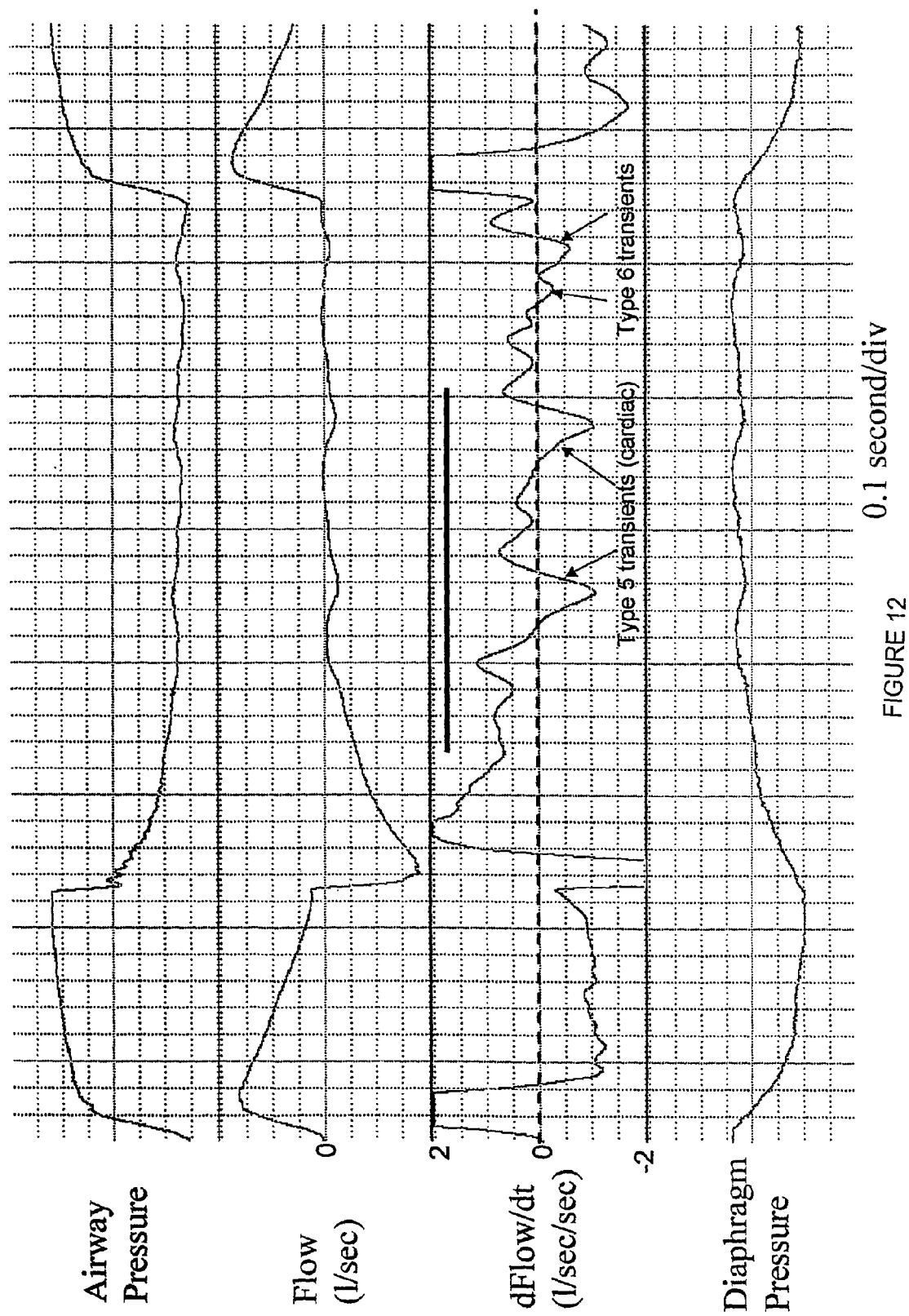

A number of other events that, unlike the previous four categories, are not related to organized respiratory acts can also produce transient increases in expiratory flow (negative dFlow/dt transients) during the ventilator's exhalation phase. These may result from biological or mechanical/electrical noise. The most common in the biological noise variety are cardiac artefacts which can, at times, result in substantial oscillations in flow (e.g. FIG. 12). Because heart rate is substantially higher than respiratory rate, the interval between successive transients of this type is less than what is expected with respiratory efforts (FIG. 12). Other causes of biological noise include erratic twitching in the diaphragm (e.g. hiccups) that can be recognized by their brief duration and occurrence at an unexpected time relative to previous or succeeding inspiratory efforts. In the mechanical noise category are vibrations in the flow signal produced by secretions, by the gas delivery system or by transient oscillations in the exhalation valve assembly. At times the flow signal is also contaminated by electrical noise. When these non-respiratory transients are of modest amplitude they do not appreciably affect estimates of $K_V$ and can, accordingly, be ignored for the sake of this application. However, at times the artefactual change in flow can be sufficiently large as to materially alter $K_V$ estimates. Thus, these artefacts may be conveniently divided into "significant", herein called type 5 transients (e.g. FIG. 12), or "insignificant", herein referred to as type 6 artefacts (e.g. FIGS. 7 to 9 and 12).

Accordingly, in this aspect of the invention, the ventilator exhalation phase is scanned for the presence of instances where expiratory flow transiently increases (negative dFlow/dt transients).

Except in cases where the pressure at the exhalation valve is actively controlled, airway pressure ($P_{aw}$) during the exhalation phase of the ventilator is the mirror image of exhaled flow. This is because when downstream pressure (i.e. at the exhalation valve in this case) is nearly constant, upstream pressure ($P_{aw}$ in this case) will vary directly as a function of exhaled flow. In essence, the exhalation tubing functions as a flow meter. In this case, $P_{aw}$ can be used as a surrogate for flow for the sake of identifying transients that may signify efforts during the exhalation phase. Note, for example, that whenever there is a negative flow transient in FIGS. 8 to 12 there is a corresponding transient in the $P_{aw}$ tracing but the polarity is opposite since an increase in expiratory flow (i.e. more negative flow value) is associated with a more positive $P_{aw}$ value. Thus, while the in the presently preferred embodiment we have utilized changes in flow to identify transients suggesting efforts or undesirable forces during the exhalation phase, $P_{aw}$ can be used instead of flow for this purpose. However, in this case one would be looking for positive (as opposed to negative) $P_{aw}$ transients where trajectory changes direction from negative (declining $P_{aw}$) to positive. Likewise, whereas the classification of type of transient, to follow immediately below, is based on flow information, it could easily be adapted for use with $P_{aw}$ instead. Accordingly, in this aspect of the invention, identification/classification of transients for the sake of identifying effort-free periods may be done using either flow or $P_{aw}$ information.

In another aspect of the invention, identified transients are classified as insignificant, and may be ignored, or significant and, hence, to be avoided in the sampling procedure. This classification process can be simple or complex depending on the circumstances in which this methodology is applied. In its simplest form, minimum dFlow, dFlow/dt and/or duration or other criteria may be specified to distinguish between significant and insignificant transients. At the other extreme, criteria are set for identifying each type of transient separately (types 1 to 6 above). While clearly more cumbersome and demanding, by defining the cause of the transient this latter approach has a number of advantages: a) It would make it possible to obtain useful data (for the sake of estimating $K_V$) from many breaths that contain significant transients. This is because once the cause is established, it becomes possible to set "safe" time regions within the same breath based on known characteristics of such a cause. For example, with a type 2 transient (phasic expiratory muscle recruitment) it would still be "safe" to sample data in the region preceding the transient, whereas with type 3 transient (ineffective effort) it would be safe to sample after the end of the transient but a substantial region before the transient, representing the period of the preceding inspiratory effort (FIG. 10), must be avoided. With the simple approach, which does not identify the specific cause of the transient, one might have to exclude all breaths that contain significant transients on the grounds that one cannot be sure where to sample data relative to the transient. b) By identifying specific causes of the negative transients, it would be possible to provide the user with useful ancillary information, for example presence and number of ineffective efforts (type 3 transients), presence of expiratory muscle recruitment (type 2 transients), inadequate inflation time (type 1 transients) . . . etc.

The preferred embodiment to be described below incorporates criteria for selectively identifying each of the six types of transients. These criteria were developed based on known physiological characteristics of the different causes of such transients and on observations of numerous examples of each kind where the specific cause could be identified with certainty (e.g. where concurrent recordings of esophageal and/or gastric pressures were available). The criteria to be described in the preferred embodiment reflect certain boundaries for transient characteristics, and associated changes in other signals, that were found, through trial and error, to offer a reasonably good separation between the various types of transients. It is to be recognized that these are only guidelines based on experience so far, which can be modified or expanded in the future. For example, it may prove useful or convenient to use a different classification of the transients by combining different types, splitting a given type into subtypes, or introducing new types. It may also be possible to use different quantitative criteria or different associated changes in other signals to effect the separation of different types. It should also be recognized that the criteria specified in the preferred embodiment were derived from signals processed in a specific way. A change in the signal processing methods would necessitate changes in the separation criteria. For example, a minimum reduction in dFlow/dt of 1.0 l/sec/sec for identifying a type 5 transient is based on the use of a smoothing interval of 100 msec in the processing of the dFlow/dt signal. The critical dFlow/dt value would be different if one uses a longer or shorter smoothing interval, and so on. For these reasons, the patent claims relating to this aspect of the invention do not specify the number of transient types to be considered or the specific characteristics that distinguish each. Rather, the claims relate to a general approach comprising the detection of negative flow transients during the exhalation phase of the ventilator and their classification into different types based on specified criteria of said transients and in other monitored or derived signals.

Another aspect of the invention relates to a decision process for selecting time regions during the ventilator's exhalation phase in which to sample $P_{aw}$, flow and volume for the sake of estimating $K_V$ by use of any of the mathematical approaches outlined earlier. Again, this decision process may be simple or complex depending on circumstances of use. In the simplest approach, sampling is avoided entirely in any expiratory phase containing a significant negative transient of any kind. Particularly when significant negative transients are very frequent, for example cardiac artefacts or when ineffective efforts are very frequent, this approach would limit the number of breaths from which useful data can be obtained. In some cases, it may not be possible to find suitable breaths for long periods. A preferred approach is to identify regions to avoid in the vicinity of the negative transients and to sample outside these regions. As indicated earlier, the specific type of the transient will dictate the location of the safe regions. In the preferred embodiment, I have used/specified certain time boundaries around each type of transient that are to be avoided. These are based on the following considerations and on numerous observations of the pattern of respiratory muscle pressure output in the vicinity of these transients:

Type 1 transient (FIG. 8): It is safe to sample in the interval beyond the end of the negative transient subject to exclusions dictated by other transients (note that diaphragm pressure reaches baseline soon after the end of the negative dFlow/dt transient, FIG. 8).

Type 2 transient (FIG. 9): This transient indicates active expiratory pressure generation. Sampling $P_{aw}$, flow and volume in the presence of a changing expiratory pressure would corrupt the $K_V$ value. Because once phasic expiratory pressure generation begins it is usually maintained until the onset of the next inspiratory effort, it is recommended that the entire period beyond the onset of the negative transient (the presumed onset of expiratory pressure) be avoided. The region preceding transient onset may be sampled from, however, subject to exclusions dictated by other transients.

Type 3 transient (FIG. 10): The onset of a type 3 transient indicates the point at which an ineffective inspiratory effort begins declining. Therefore, in order to sample data that are free of inspiratory pressure it is necessary to avoid a period extending from well before the onset of the transient, reflecting the estimated duration of the rising phase of the effort, to well after the onset of the transient to exclude the period of the declining phase of $P_{MUS}$. In my experience with several thousand documented ineffective efforts, the duration of the rising phase varies considerably from 0.3 to 1.0 sec and the declining phase of the effort rarely extends beyond the end of the negative transient (FIG. 10). Because the duration of the rising phase is highly variable, it is preferable to individualize the excluded zone preceding the transient based on the likely onset of the rising phase of the transient in question. Accordingly, in the preferred embodiment, a procedure is described whereby the lowest Signal value preceding transient onset is identified. Decisions as to the extent of the excluded zone are based on Signal level at this point relative to a previously identified minimum (see Preferred Embodiment). Clearly, expanding the region to be avoided would be a more conservative approach that covers instances where the rising and declining phases are longer than anticipated. However, expanding the avoidance region decreases the chance of obtaining useful data in patients who have many ineffective efforts.

Type 4 transients (FIG. 11): Coughing is a substantial event that has consequences that outlast the event itself. For this reason, in the preferred embodiment, breaths that include a cough effort are not used for $K_V$ determination. It may even be advisable to avoid sampling from a number of breaths following a cough effort.

Type 5 transients (FIG. 12): These are usually produced by forces that have a briefer duration than inspiratory efforts (cardiac contractions, hiccups, secretion noise). A narrower avoidance region, extending from 0.5 second before transient onset to 0.1 second after transient end was selected and was found to be satisfactory.

Type 6 transients are of little mechanical consequence and can be ignored.

It is clear that the above ineligibility boundaries placed about each transient type are suggestions based on personal experience and preferences. Others may elect more conservative or more liberal boundaries. For this reason, the patent claims relating to this aspect of the invention do not specify numerical values for the ineligibility boundaries placed about each transient type. Rather, the claims relate to a general approach comprising the detection of negative flow transients during the exhalation phase of the ventilator and the exclusion from sampling of user/builder-specified regions in the vicinity of said negative transients.

The horizontal black bars in FIGS. 7 to 12 show the excluded regions applicable to the examples illustrated, based on the criteria suggested above and used in the preferred embodiment. There are no excluded regions in the example of FIG. 7. These excluded regions define the regions that can be sampled from in each breath (i.e. regions outside the excluded regions). Since the intent of this invention is to derive a $K_V$ value that results in a relatively flat Signal baseline, and since the units of $K_V$ are in pressure/unit volume, the wider the volume range over which samples are obtained the less vulnerable the resulting $K_V$ will be to measurement errors and noise. For this reason, once the eligible regions are identified, it is preferable to obtain samples at the beginning of the first (or only) eligible period and at the end of the last (or only) eligible region. This is the practice employed in the preferred embodiment. At times, because of the specific distribution of ineligible regions, the volume spanned by these two extreme points is quite small. It has been our practice not to sample from breaths where the volume spanned by the two extreme points is <40% of the total exhaled volume. Alternatively, sample obtained within "safe" regions in separate breaths may be used so long as the selected points encompass a sufficient volume range. This approach, however, is vulnerable to drifts in the volume signal.

Whether more samples, other than the two extremes, need to be acquired is a matter of personal choice. I found that adding more samples and using regression analysis (as detailed above) increases computational time without providing a commensurate enhancement in the results. For this reason, the preferred embodiment employs the two-point approach, at the extremes of the eligible regions, and applies Equation 5 to the sampled values. Others, however, may prefer a multi-sample approach.

Figure 13:
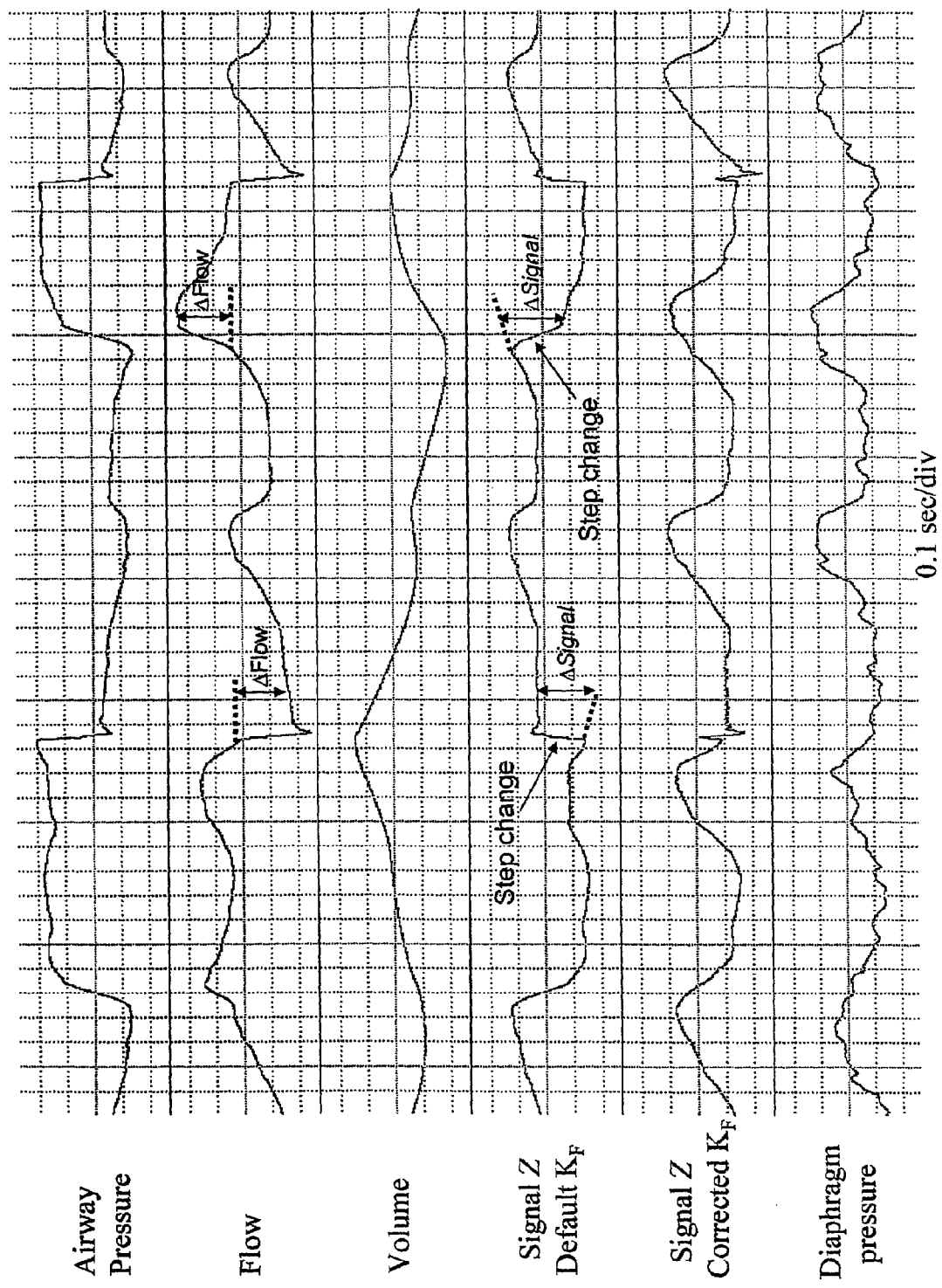
FIG. 13 contains traces of airway pressure, flow, volume, Signal Z for default $K_F$, Signal Z for corrected $K_F$, and diaphragm pressure, illustrating step changes in calculated Signal at ventilator triggering and cycling-off.

Although the use of a fixed default value for $K_{F1}$ (e.g. 10 cmH$_2$O/l/sec, as suggested above) accomplishes the main objective of obtaining a stable baseline Signal during the exhalation phase, at times a fixed (i.e. same for all patients and at all times) default value is associated with step changes in the calculated Signal at ventilator triggering and cycling-off (FIG. 13). These step changes are not natural in that there are no corresponding step changes at these time points in the real pressure output of respiratory muscles (see diaphragm pressure, FIG. 13). Although there are several reasons for the development of artefacts at triggering and cycling-off times, one potential reason is that the $K_{F1}$ used is substantially different from real patient's resistance. Such large differences between $K_{F1}$ and patient's resistance would cause a step change in Signal whenever flow changes rapidly, such as at triggering and cycling-off times. The direction of the step change would depend on the direction of the difference between $K_{F1}$ and patient's resistance (i.e. it may be positive or negative). In another aspect of this invention, a procedure is described to calculate the $K_{F1}$ correction required to minimize the step changes in Signal at triggering and cycling-off (early and late $K_{F1}$ error estimation). This procedure is shown schematically in FIG. 13. Thus, for early $K_{F1}$ error calculation, the trajectory of Signal prior to triggering is extrapolated forward for a brief period beyond triggering (dotted line, FIG. 13). The extrapolated value is then subtracted from actual Signal value at a time where flow is no longer changing rapidly. The calculated difference provides an estimate of the magnitude of step change in Signal ($\Delta$signal, FIG. 13). The difference in flow over the same interval is also calculated ($\Delta$Flow, FIG. 13). The ratio [$\Delta$Signal/$\Delta$Flow] thus provides an estimate of how much $K_{F1}$ needs to be adjusted to eliminate the step change at triggering and restore a physiological appearance to the rising phase of Signal (early $K_{F1}$ error). This error can then be added to (or subtracted from) the $K_{F1}$ value used, to arrive at a new $K_{F1}$ value to be used in future breaths. A similar procedure can be used to determine the adjustment in $K_{F1}$ required to minimize the step change in Signal at cycling-off (FIG. 13). Because patient's resistance is not constant over the entire respiratory cycle, being affected by the flow range and volume at time of measurement (among other things), the error calculated at triggering and cycling-off need not be the same. At times, calculation of either the early or late $K_{F1}$ error or both is not feasible (see Preferred Embodiment, below). In this case whichever value is available can be used to adjust $K_{F1}$. When both procedures are possible in a given breath my preference has been to use the late $K_{F1}$ error to adjust $K_{F1}$. This is because there is usually less uncertainty with the extrapolated values and the change in flow is usually crisper (FIG. 13).

There are clearly numerous ways by which step changes in Signal at triggering and cycling-off can be minimized. In the preferred embodiment, I utilize an approach that relies exclusively on adjustments to $K_{F1}$ to produce the desired effect. It is, however, possible to achieve a similar result through more complex changes to $K_V$ and/or $K_{F1}$ and/or $K_{F2}$. A variety of extrapolation approaches can also be used. In the preferred embodiment, Signal is extrapolated with a time course (slope) that is the average of Signal's trajectory just before triggering (or cycling-off) and its trajectory at the point where dFlow/dt approaches zero. Others may elect to use other, equally valid, extrapolation techniques, for example non-linear forward extrapolation based on shape of signal prior to triggering (or cycling-off). Extrapolation may also be done backward from the post-triggering (or post-cycling-off) point. In the preferred embodiment, Signal is extrapolated forward up to a specified point (based on flow trajectory) beyond triggering (or cycling-off). Others may reasonably choose a different extrapolation interval. Likewise, when both early and late $K_{F1}$ error estimates are available, the late one is used in the preferred embodiment. Using the early error, an average of the two error values, or some weighted average are also feasible approaches in these circumstances. For these reasons, the patent claims relating to this aspect of the invention do not specify the procedure to be used to minimize step changes in Signal at triggering and cycling-off. Rather, the claims relate to an approach in which the $K_{F1}$ value used to generate Signal is selected to minimize step changes in Signal value at the times of triggering and/or cycling-off of the ventilator.

It was of interest to determine the extent to which the $K_{F1}$ value, corrected according to the above procedure, approximates actual patient resistance and, by extension, whether $K_V$, calculated using the corrected $K_{F1}$ value approximates actual patient's elastance. In 21 patients in whom actual resistance and elastance were available, there was a good correlation between corrected $K_{F1}$ and resistance (r=0.78, p<0.0001) and between $K_V$ and elastance (r=0.77, p<0.0001) (Younes M, Brochard L, Grasso S, Kun J, Mancebo J, Ranieri M, Richard J C, Younes H. A METHOD FOR MONITORING AND IMPROVING PATIENT-VENTILATOR INTERACTION. To be submitted). Thus, while my aim was simply to produce a Signal shape having physiological attributes of normal inspiratory efforts (i.e. flat baseline during expiration and a physiologically appearing rising phase with no discontinuities), it appears that when $K_{F1}$ is adjusted to simply eliminate discontinuities in Signal at triggering and cycling-off both $K_{F1}$ and $K_V$ become reasonable approximations of actual resistance and elastance. As such, display of these values to the user may be of use clinically.

It was of interest to determine the extent to which the $K_{F1}$ value, corrected according to the above procedure, approximates actual patient resistance and, by extension, whether $K_V$, calculated using the corrected $K_{F1}$ value approximates actual patient's elastance. In 21 patients in whom actual resistance and elastance were available, there was a good correlation between corrected $K_{F1}$ and resistance (r=0.78, p<0.0001) and between $K_V$ and elastance (r=0.77, p<0.0001) (Younes M, Brochard L, Grasso S, Kun J, Mancebo J, Ranieri M, Richard J C, Younes H. A METHOD FOR MONITORING AND IMPROVING PATIENT-VENTILATOR INTERACTION. To be submitted). Thus, while my aim was simply to produce a Signal shape having physiological attributes of normal inspiratory efforts (i.e. flat baseline during expiration and a physiologically appearing rising phase with no discontinuities), it appears that when $K_{F1}$ is adjusted to simply eliminate discontinuities in Signal at triggering and cycling-off both $K_{F1}$ and $K_V$ become reasonable approximations of actual resistance and elastance. As such, display of these values to the user may be of use clinically.

It is clear that the steps of identifying a suitable $K_V$ by sampling $P_{aw}$, flow and volume during effort-free zones in the exhalation phase may be rendered unnecessary if ones knows, or can reasonably estimate, actual patient elastance through other means. Accordingly, in another aspect of the invention, the $K_v$ value used is a known or estimated value of patient's elastance while the $K_F$ value used for generating Signal is according to the methods described above for minimizing step changes in Signal at the time of ventilator triggering and/or cycling-off.

The information provided by the present invention in conjunction with the earlier Younes invention, can be utilized in a number of ways: First, the time of $T_{onset}$ derived from the composite Signal can be used to trigger ventilator cycles by providing an appropriate command to the ventilator's triggering mechanism. Second, the end of the ventilator inflation phase (cycling-off) can be made to coincide with the end of patient effort identified from the generated Signal ($T_{END}$) through appropriate connections to the cycling-off mechanism of the ventilation. Third, cycling off may occur at the identified $T_{end}$, conditional on this not violating a specified minimum $T_1/T_{TOT}$ ratio.

Whether or not it is used to synchronize the ventilator with patient effort, the information provided by the Signal can be displayed to the user to assist him/her in adjusting ventilator settings to, indirectly, improve patient ventilator interaction. In this connection, the information may be printed out on command or be displayed on a monitor. The Signal itself can be displayed in real time along with other useful waveforms, such as flow and airway pressure. In addition, numerical values concerning patient ventilator interaction can be displayed. Some recommended values include:
 a) Trigger delay (difference between ventilator trigger time and $T_{onset}$).
 b) Cycling-off error (difference between ventilator cycling-off time and end of inspiratory effort identified from Signal ($T_{END}$)).
 c) True respiratory rate of patient (number of inspiratory efforts per minute).
 d) Average duration between inspiratory efforts ($T_{TOT}$).
 e) Number of ineffective efforts, per minute or as a fraction of respiratory rate. This is calculated as the difference between true rate of the patient and ventilator rate.
 f) Number of central apneas (no inspiratory efforts for a specified period, for example 10 seconds) per hour, and/or % of time spent in central apnea.

The numerical values may be accompanied by displayed suggestions on how to adjust ventilator settings to reduce the undesirable aspects of current interaction.

DESCRIPTION OF PREFERRED EMBODIMENT

Figure 14:
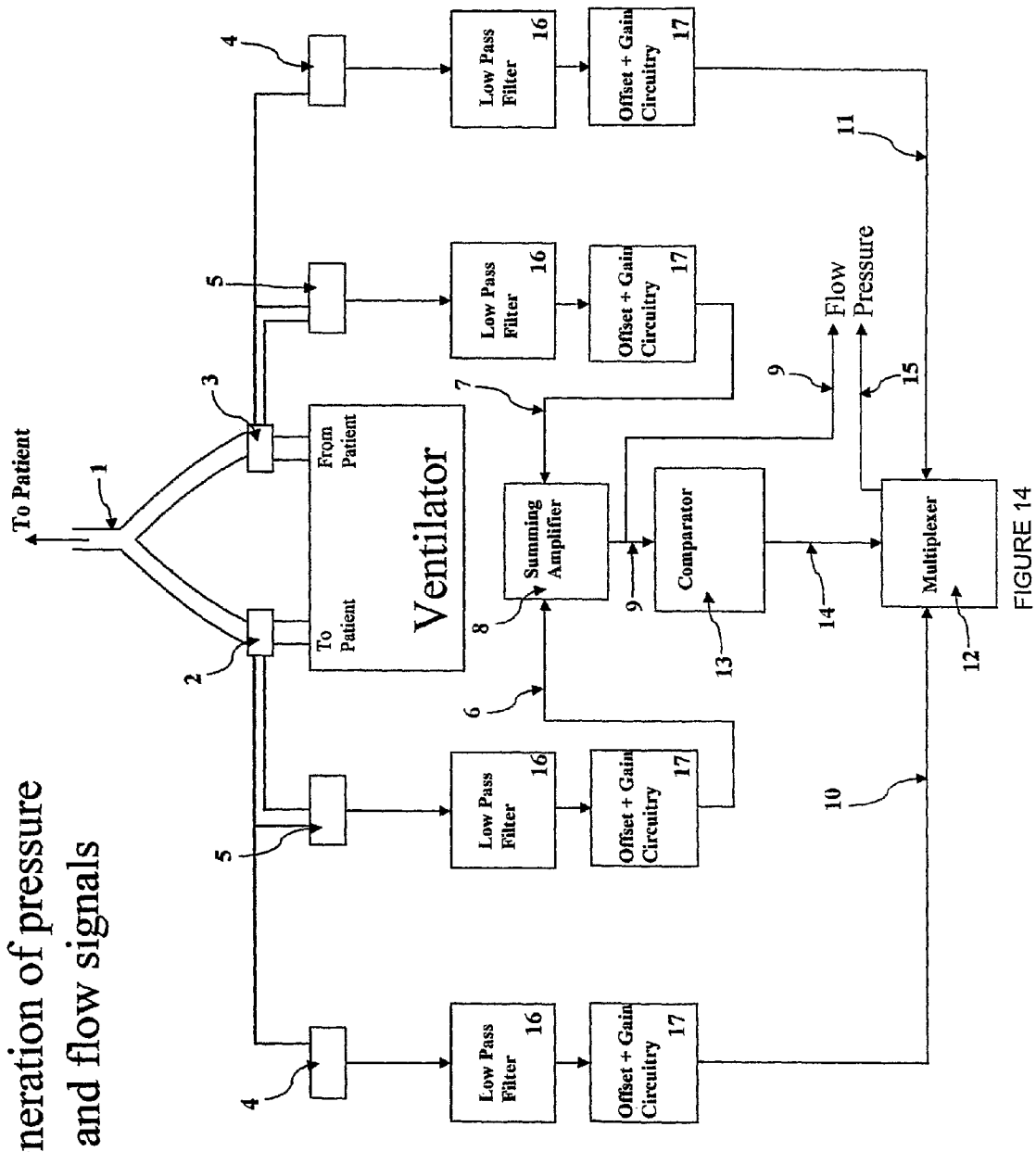
FIG. 14 is a schematic representation of the generation of pressure and flow signals.

The procedures of the present invention as described in details above may be implemented in a device which may be constructed as a freestanding device to be attached externally to a ventilator, or may be incorporated within the ventilator. In either case, the operation of the device requires inputs related to pressure and airflow in the ventilator circuit. FIG. 14 shows a design and components suitable for obtaining these inputs. Although it is possible to obtain these inputs by attaching a flow meter and pressure port to the common tube connecting ventilator to patient 1, it is preferable to monitor flow and pressure separately in the inspiratory and expiratory lines and to combine the signals. This is to avoid clogging of the flow meter and to minimize the number of tubing connections extending from near the patient's head to the device. Accordingly, as shown in FIG. 14, a flow meter and pressure port are inserted in the inspiratory line 2 and another set is inserted in the expiratory line 3. Each set is connected to appropriate pressure 4 and flow 5 transducers, which generate electrical outputs proportional to pressure and flow, respectively. For analog processing, the output from each pressure 4 and flow 5 transducer is conditioned with suitable low pass filters (e.g. 10 Hz) and offset and gain circuitry. Suitable calibrations for the pressure and flow inputs are 10 cmH$_2$O/volt and 1.0 l/sec/volt, respectively. The processed inspiratory 6 and expiratory 7 flow inputs are summed using a summing amplifier 8 to produce a composite flow input 9 to be used by the device. The inspiratory 10 and expiratory 11 pressure inputs are connected to a multiplexer 12. A comparator 13 receives the composite flow input 9 and provides a signal 14 to the multiplexer 12 indicating the polarity of flow 9. The multiplexer generates a pressure output 15 composed of the inspiratory pressure value 10 when flow is expiratory and the expiratory pressure value 11 when flow is inspiratory. In this fashion, the pressure 15 measured at any instant is a close approximation of pressure in the tubing near the patient 1 since at all times a static air column exists between the active transducer and the common ventilator tubing 1 near the patient.

Pressure and flow values are routinely generated in modern ventilators using an approach similar to that of FIG. 14. If the device of this invention is incorporated in the ventilator, the pressure and flow values generated independently by the ventilator can be used instead.

Figure 15:
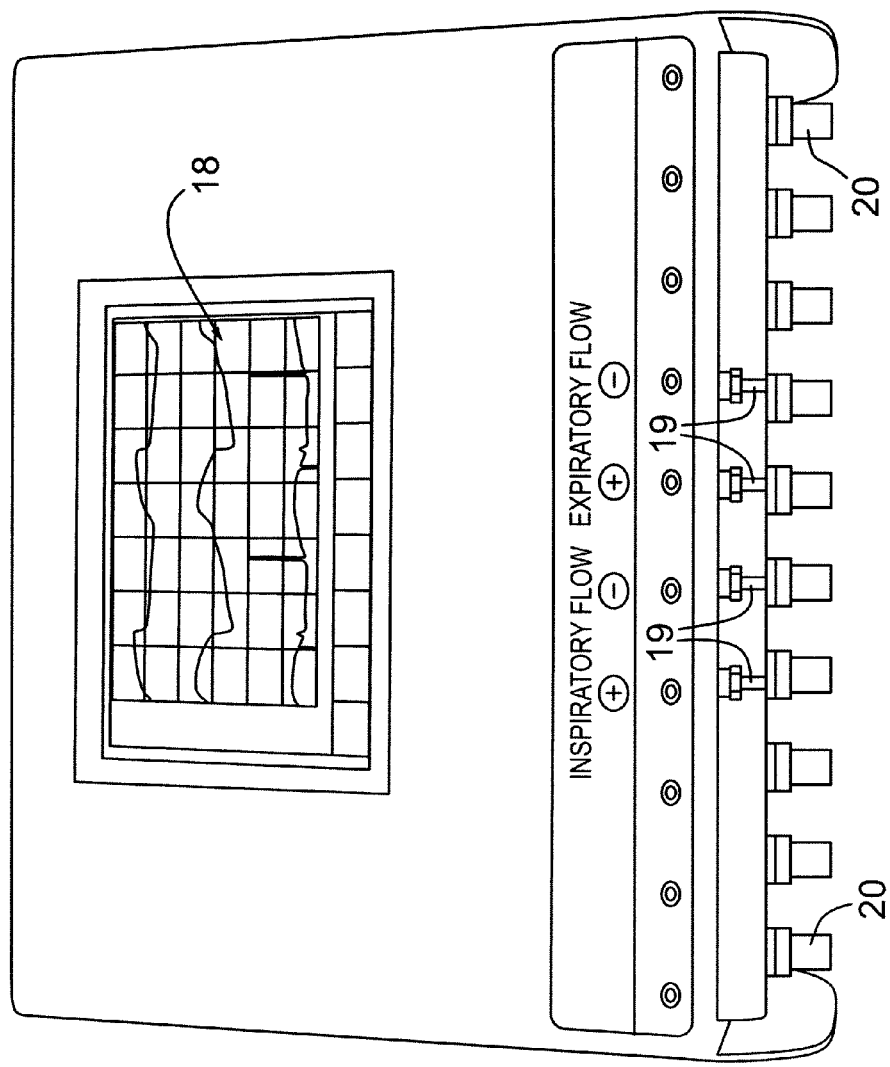
FIG. 15 is a photograph of a free-standing prototype that operates according to one preferred embodiment of the invention.

FIG. 15 is a photograph of a freestanding prototype that operates according to one preferred embodiment. There is a monitor 18 that serves several purposes: a) To display real-time waveforms and other numerical and graphic data generated from analysis of the effort Signal and the associated $P_{aw}$, flow and volume signals. The waveforms or data to be displayed are selected by touch-screen buttons displayed on the graphical user interface (GUI). b) To input information used in some of the functions, such as the mode of ventilation, whether an endo-tracheal tube is in place and, if so, its size (from which the value of $K_{F2}$ for use in Equations 4 to 6 is derived), the form in which $P_{aw}$ and flow will be inputted (analog, transducer or digital) . . . etc. c) to calibrate the pressure and flow signals when the transducer input mode is used. d) To select variables to be outputted for use by external devices.

On the bottom surface there are two rows of connectors. The front row consists of 4, ⅛ inch diameter barbed male tubing connectors 19 for connection to the expiratory and inspiratory flow meters in ventilator tubing 5 in the event transducer input form is selected. The back row consists of a series of electrical BNC connectors 20. Two of these are input connectors to input $P_{aw}$ and flow data in the event analog input is selected. The others are output connectors for use to display various outputs on external monitors or store said outputs on external recording systems. Examples of outputs that can be selected (via the touch-screen feature) for external use include $P_{aw}$, $dP_{aw}/dt$, Flow, dFlow/dt, Signal, dSignal/dt and Volume.

Figure 16:
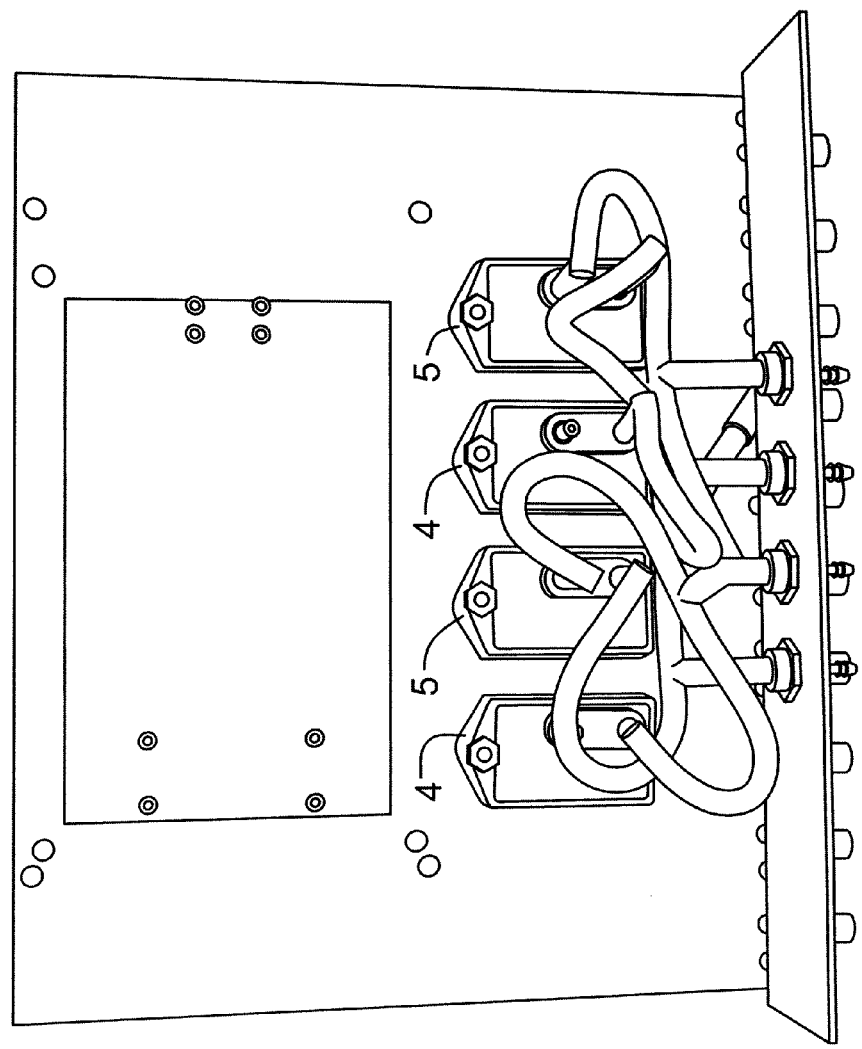
FIG. 16 is a photograph of one side of the transducer board of the prototype of FIG. 15 that generates pressure and flow inputs in the transducer data acquisition mode.

FIG. 16 is a photograph of one side of the board that generates pressure and flow inputs in the transducer data acquisition mode. Two flow transducers (Honeywell, 163PC01D36) and two pressure transducers (Honeywell, 143PC01) are shown one pair for the inspiratory line and one pair for the expiratory line. Tubing is arranged according to the diagram of FIG. 14.

Figure 17:
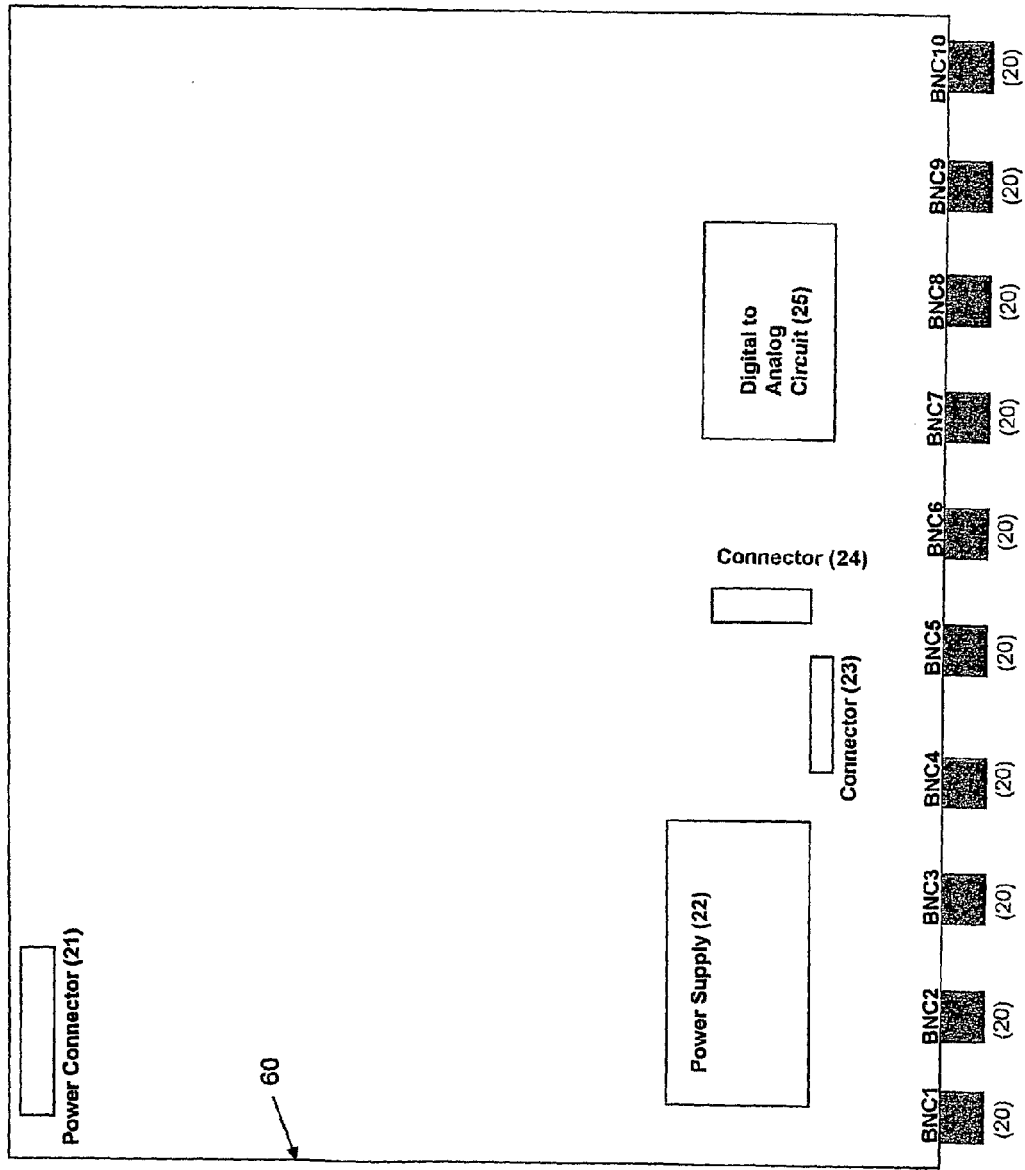
FIG. 17 is a block diagram of the other side of the transducer board of the prototype of FIG. 15.

FIG. 17 is a block diagram of the other side of the transducer board 60. Power enters the board via a standard 3 pin male Molex connector 21. This connector receives its power from an external 12 volt DC power source plugged into the back of the device. Power is transmitted through the board into the power supply 22. This supply converts the +12 volts to +3.3 volts via a LM2674M-ADJ adjustable voltage converter, to ±15 volts via a TPS61040DVB adjustable voltage boost converter and to +10 volts via a MIC5205BM5 fixed voltage regulator. The +10 volts supply is used to power the pressure 4 and flow 5 transducers. The ±15 volts is used to power the digital to analog circuit 25 and the +3.3 volts is transmitted to connector 24 for use on the microprocessor (CPU) board 61. A standard 6 pin male Molex Connector 23 is used to transmit digital signals from the microprocessor board 61 to the monitor 18. A board mount, 40 pin low profile female socket connector 24 is used to connect the microprocessor board 61 to the transducer board 60. The connector 24 transmits analog voltages from BNC connectors 20 to the microprocessor board 61 as well as digital signals controlling the digital to analog circuit 25 and digital signals to the monitor 18. The digital to analog circuit 25 converts digital signals from the microprocessor board into analog values for output on the BNC connectors 20. The digital to analog circuit 25 consists of 74VHCT14 Schmitt trigger inverters, DAC7714U, 12 bit serial digital to analog converters, an OP07D low noise operational amplifier, a LM4040BIM3-5.0 precision −5 volt reference diode and a LM4040BIM3 5.0 precision 5 volt reference diode. There are also numerous resistors, capacitors, diodes and inductors used throughout circuits 22 and 25. These are merely necessary to allow the circuits to function correctly as per the manufacturer's specifications and will not be separately itemized.

Figure 18:
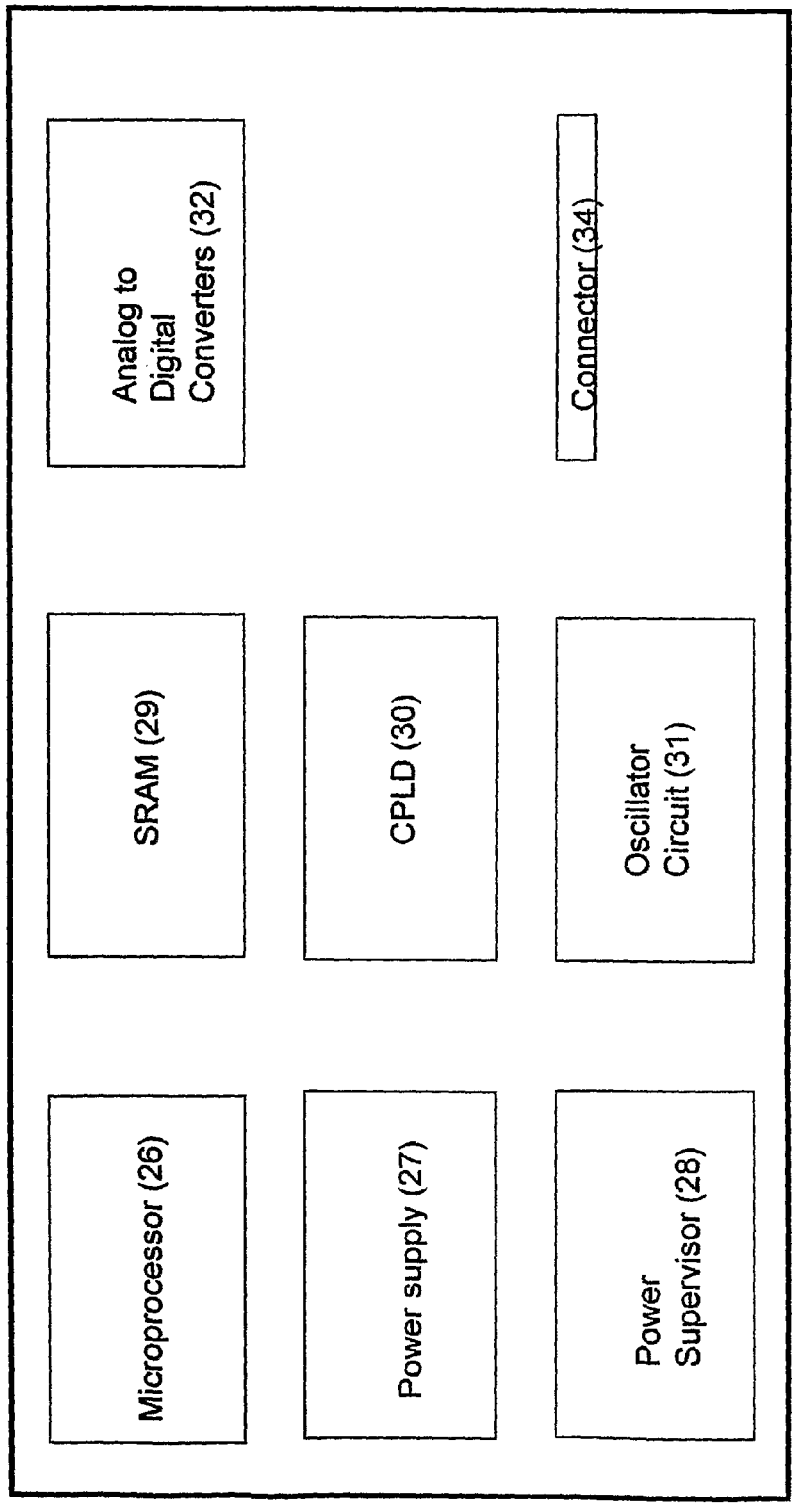
FIG. 18 is a block diagram of the microprocessor board of the prototype of FIG. 15 that performs the various functions.

FIG. 18 is a block diagram of the microprocessor board 61 that performs the various functions. The microprocessor 26 consists of a LPC2138, Phillips ARM7 processor. It has internal programmable non-volatile memory which stores the functions described in FIGS. 19 and 22. Its internal volatile memory is insufficient to execute all of the functions described in FIGS. 19 and 22 and, therefore, it is interfaced to AS7C34096, 2×512 KB external SRAM 29 via XC9536XL-10CS48C chip scale package CPLD 30. The CPLD 30 acts strictly as an address decoder for the SRAM 29. The microprocessor 26 is timed via oscillator circuit 31 consisting of a HC49SD 3.684 MHz oscillator and a SG-615P 6.144 MHz oscillator. The microprocessor 26 has its voltage supervised by power supervisor 28 consisting of a MCP809-315 standard voltage supervisor. The power supervisor 28 will reset the microprocessor 26 if the voltage supply drops below a set threshold. The power supply 27 consists of a MIC5205BM5, +1.8 volt regulator supplying additional power to the microprocessor 26 and a PS61040DVB, +5 volt regulator supplying power to the analog to digital converters 32. The analog to digital converters 32 consist of ADS1256DB, 24 Bit Serial A/D converters and are interfaced to the microprocessor 26 via the CPLD 30 which decodes the chip selection. The analog to digital converters 32 connect to the transducer board analog signals via connector 34. The connector 34 is a board mount, male 40 pin low profile socket connector. It connects to the transducer board and provides a signal path for various digital and analog signals as described above. There are also numerous resistors, capacitors, diodes and inductors used throughout circuits 26 to 33 inclusive. These are merely necessary to allow the circuits to function correctly as per the manufacturers specifications and will not be separately itemized.

Figure 19:
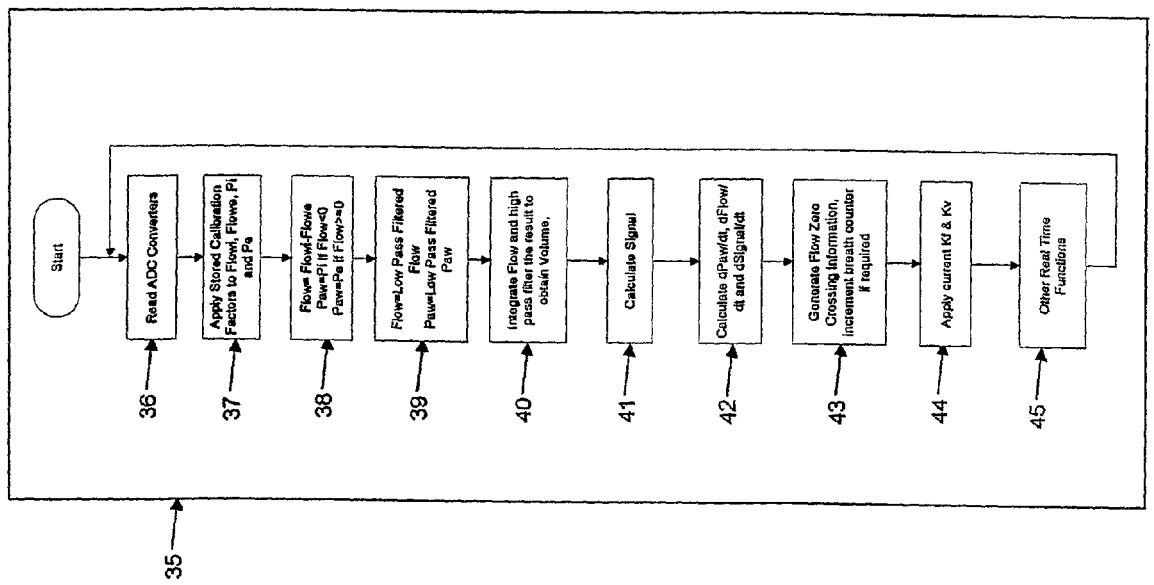
FIG. 19 is a block diagram of various real-time functions executed by the microprocessor on the microprocessor board of FIG. 18.

Real-Time Functions, 35, FIG. 19:

FIG. 19 is a block diagram of the various real-time functions executed by the microprocessor 26. Only those functions that are relevant to the claims of this application will be discussed in detail. These functions are repeated at 5 msec intervals.

1) Reading the analog to digital converters 36. Self explanatory.
2) Apply stored calibration factors to inspiratory flow, expiratory flow, inspiratory pressure, expiratory pressure 37. Self explanatory.
3) Sum inspiratory and expiratory flows to generate a common flow value and select appropriate pressure signal depending on polarity of flow 38.
4) Filter the pressure and flow signals 39: This filter is a numerical implementation of a 2nd order low pass Butterworth configuration with an 8.5 Hz cutoff frequency.

Functions 2 to 4 (37 to 39) are operative only in the transducer input mode and essentially substitute for the corresponding functions in the analog embodiment (8 to 17, FIG. 14). It is clear that these functions may be performed by analog circuitry, such as that described in relation to FIG. 14. It is also clear that processed pressure and flow inputs can be derived from independent measurement systems, such as those included in most commercial ventilators. For these reasons, the prototype developed here includes an option to input the pressure and flow signals in analog form. In this case, these pre-processed inputs are digitized and are then processed beginning at step 5, below, without undergoing steps 2 to 4 above.

5) Integrate the composite flow to generate a volume signal 40. Here, the composite flow value 39 is integrated with no reset. Because of inevitable offsets in the composite flow signal, the integrated signal is high-pass filtered to maintain the baseline of the volume signal close to zero. This filter is a numerical implementation of a 1st order high pass Gaussian configuration with an 0.005 Hz cutoff frequency.
6) Generation of the composite Signal 41. This is done using Equation 4:

Signal=Volume*$K_V$+Flow*$K_{F1}$+(Flow*absolute flow*$K_{F2}$)−$P_{aw}$

Where: Volume is current volume value;

$K_{F2}$ is a constant related to the size of the endotracheal tube, when presence and size of said tube was indicated at start-up. It is obtained using a look-up table. The table is derived from the $K_2$ values for different size tubes published by Wright et al (Wright, P. E., J. J. Marini, and G. R. Bernard. 1989. In vitro versus in vivo comparison of endotracheal tube airflow resistance. *Am. Rev. Respir. Dis.* 140:10-16). Thus: the values used are 15.0, 9.5, 7.0, 5.5, 4.0, 3.0 for tube sizes 6, 7, 7.5, 8.0, 8.5, and 9.0 respectively; For non-invasive applications the user may input "no tube", in which case $K_{F2}$ is assigned a value of zero. Alternatively, if the user wishes to incorporate a non-linear component to account for resistive properties of upper airway passages he/she may input a tube size with a $K_2$ that is comparable to that estimated for upper airway passages.

$K_{F1}$ is a flow coefficient (in $cmH_2O$/l/sec) stored in memory. This value may be a constant. In this case, a value of 10 is recommended as it represents the average value for patient resistance (i.e. after subtracting ET tube resistance) in ventilated patients (from. Younes M, Kun J, Masiowski B, Webster K, and Roberts D. 2001. A Method for Noninvasive Determination of Inspiratory Resistance during Proportional Assist Ventilation. *Am. J Respir. Crit. Care Med.* 163: 829-839). Alternatively, $K_{F1}$ may be a directly measured resistance value that is independently measured and inputted into memory by the user. Furthermore, there are currently methods for automatic determination of resistance in spontaneously breathing patients on ventilators (e.g. Younes et al, idem). If such a method is operative in conjunction with the current invention, the results can be used to frequently update the $K_{F1}$ value in memory. In the current preferred embodiment, an initial default value of 10 is used. This value is subsequently updated at intervals based on the results of an algorithm that attempts to minimize step changes in calculated Signal at ventilator triggering and cycling-off (see $K_{F1}$ error function in Non Real-Time Functions discussed below).

$K_V$ is a volume coefficient stored in memory. Initially, a default value of 25 is placed in memory. This value is then updated after every breath based on the results of the $K_V$ estimation function in elapsed breaths (see Non-Real-Time Functions discussed below).

7) Generation of time derivatives of $P_{aw}$, flow and Signal 42: These (i.e. $dP_{aw}/dt$; $dFlow/dt$; $dSignal/dt$) are generated in real-time but are required in the Non-Real-Time functions (see below). A smoothing interval of 100 msec (20 samples) is used in the current preferred embodiment. As well, a 50 msec moving average of Signal is generated (MA Signal)

8) Generate zero flow crossing information 43: This function identifies when a valid inspiratory phase has started (transition from expiration to inspiration ($T_{EI}$)) and when a valid expiratory phase has started ($T_{IE}$). These times are then stored and used subsequently to determine the timing of retrospective analysis (see Non Real-Time Functions discussed below). $T_{EI}$ (flow channel, FIG. 23) is the point at which flow crosses zero on the way to an inspiratory phase. It is marked at the first point where flow exceeds 0.07 l/second and remains continuously above this level for 0.3 second. Alternatively, $T_{EI}$ is identified if flow exceeds 0.07 l/second for only 0.2 sec but $P_{aw}$ had increased over this interval by at least 5 $cmH_2O$. $T_{IE}$ (flow channel, FIG. 23): is the point at which flow crosses zero on the way to an expiratory phase. It is marked at the first point where flow decreases below −0.07 l/second and remains below this level, continuously or intermittently, for a total of 0.25 sec of a 0.30 second interval.

9) Apply current $K_{F1}$ and $K_V$ 44: As will be seen in Non Real-Time Functions below, the values of $K_{F1}$ and $K_V$ in memory are updated every time valid measurements can be made from an elapsed breath. However, it is not desirable to apply the new values to Signal calculation as soon as the value in memory is updated. In the event the new value is quite different from the old, applying the new value will result in a step change in calculated Signal that may lead to errors (e.g. such a step change may be interpreted as an ineffective effort or a $T_{ONSET}$). For this reason, updating the values of $K_{F1}$ and $K_V$ to be used in real-time calculation of Signal is done at a specific time of the respiratory cycle where such step changes cannot lead to errors. This occurs 300 ms after flow exceeds 0.3 L/s. The "Apply current $K_{F1}$ and $K_V$ function" 44 tracks the phases of the respiratory cycle in real-time and updates the values to be used for Signal calculation at the appropriate time.

10) Other Real-Time Functions 45: These are primarily concerned with directing the appropriate information to the microprocessor that operates the monitor 18 and with real-time detection of the onsets ($T_{ONSET}$) and ends ($T_{END}$) of inspiratory efforts from the generated Signal for use in real-time triggering and cycling-off of a ventilator. The methods for identifying $T_{ONSET}$ and $T_{END}$ in real-time have been described in detail in the aforementioned U.S. patent application Ser. No. 10/517,384 and EP application 03 739906; Method and Device for monitoring and Improving Patient-Ventilator Interaction, which are incorporated here by reference. The basic principles involved in these determinations have also been described under Detailed Description of the Invention, above.

Figure 20:
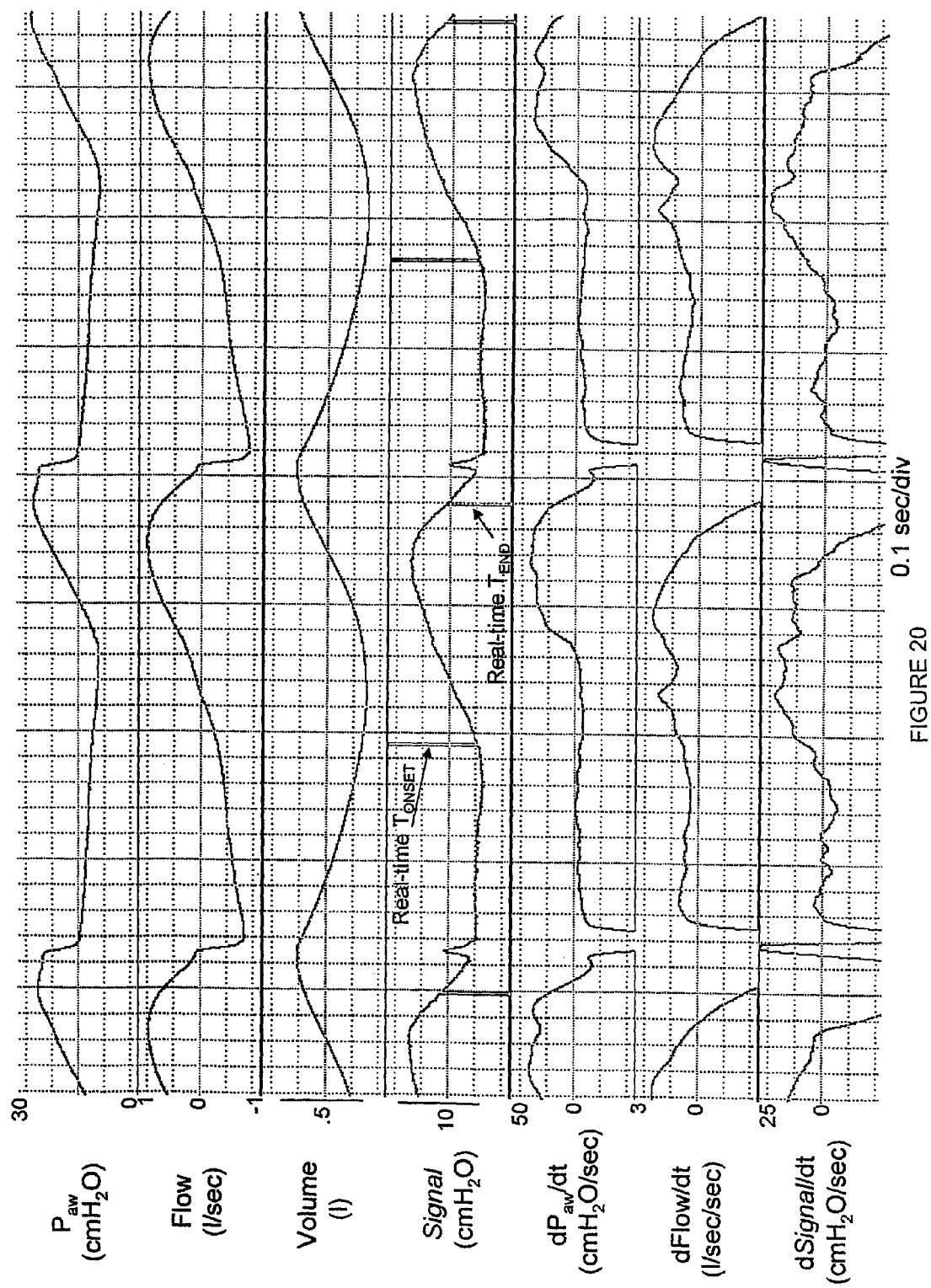
FIG. 20 contains traces of data produced in real-time using the prototype of FIG. 15.
Figure 21:
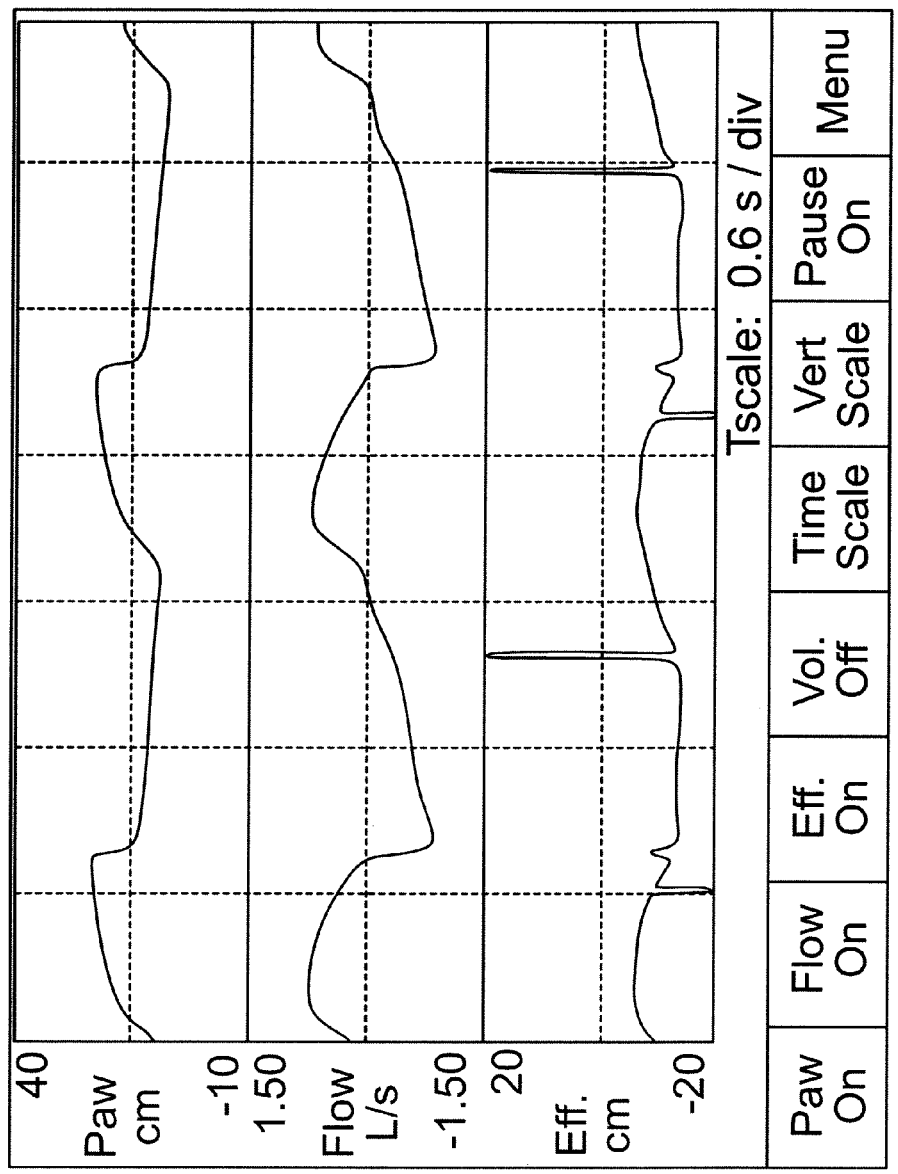
FIG. 21 is a photograph of data.

An example of data produced in real-time is shown in FIG. 20. These were outputted during real-time processing through the electrical output connectors 20 and recorded using a Windaq data acquisition system (DATAQ Instruments, Inc., Akron Ohio). Similar data are displayed on the monitor but, because of its small area, only 3 channels can be displayed at anytime (as shown in FIG. 21). In both Figures, the generated Signal is clearly seen (it is called Eff (i.e. effort) on the monitor). The $T_{ONSET}$ and $T_{END}$ markers are also displayed in real-time (in the Signal channel in FIG. 20, Eff channel in FIG. 21). If directed to the control system of a ventilator, these markers of onset and end of effort may be used to actively control ventilator's triggering and cycling-off.

Figure 22:
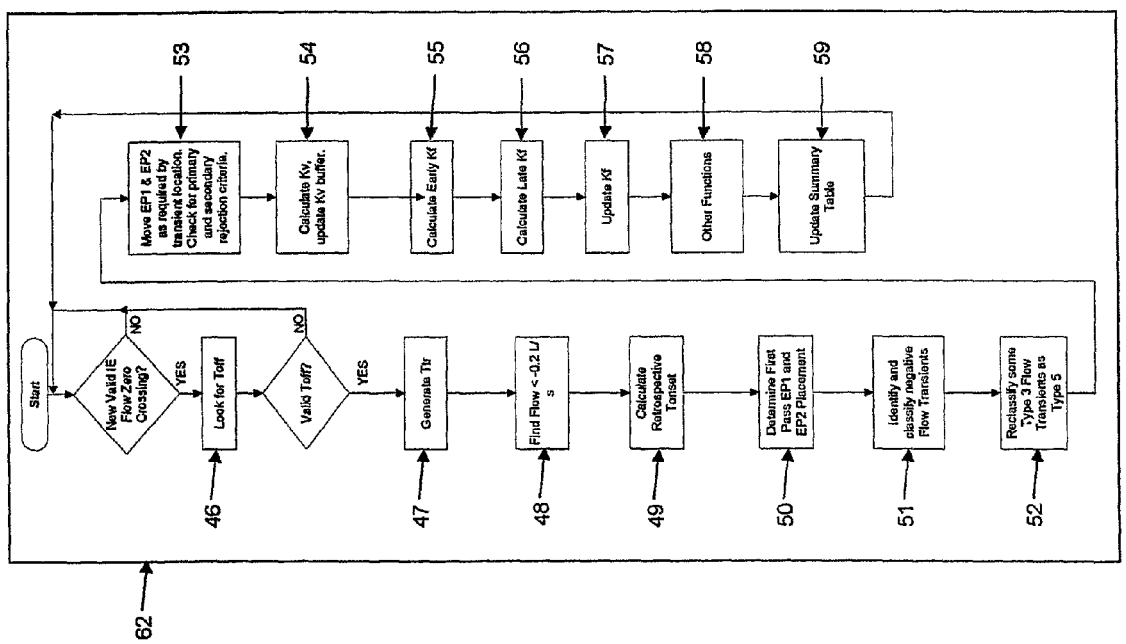
FIG. 22 is a block diagram of various non real-time functions executed by the microprocessor on the microprocessor board of FIG. 18.
Figure 23:
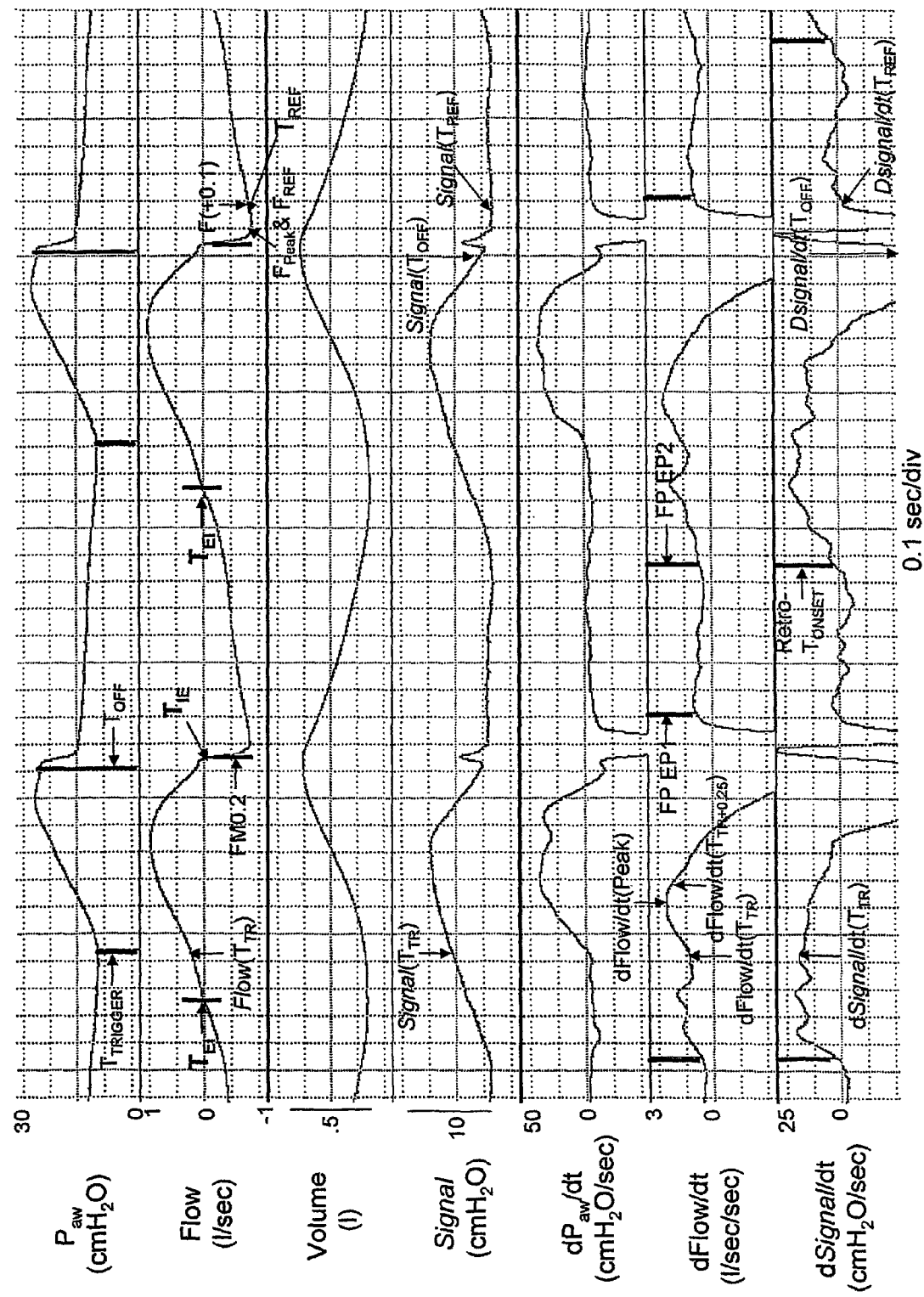
FIGS. 23 and 24 contain traces of variables used to execute non real-time functions.
Figure 24:
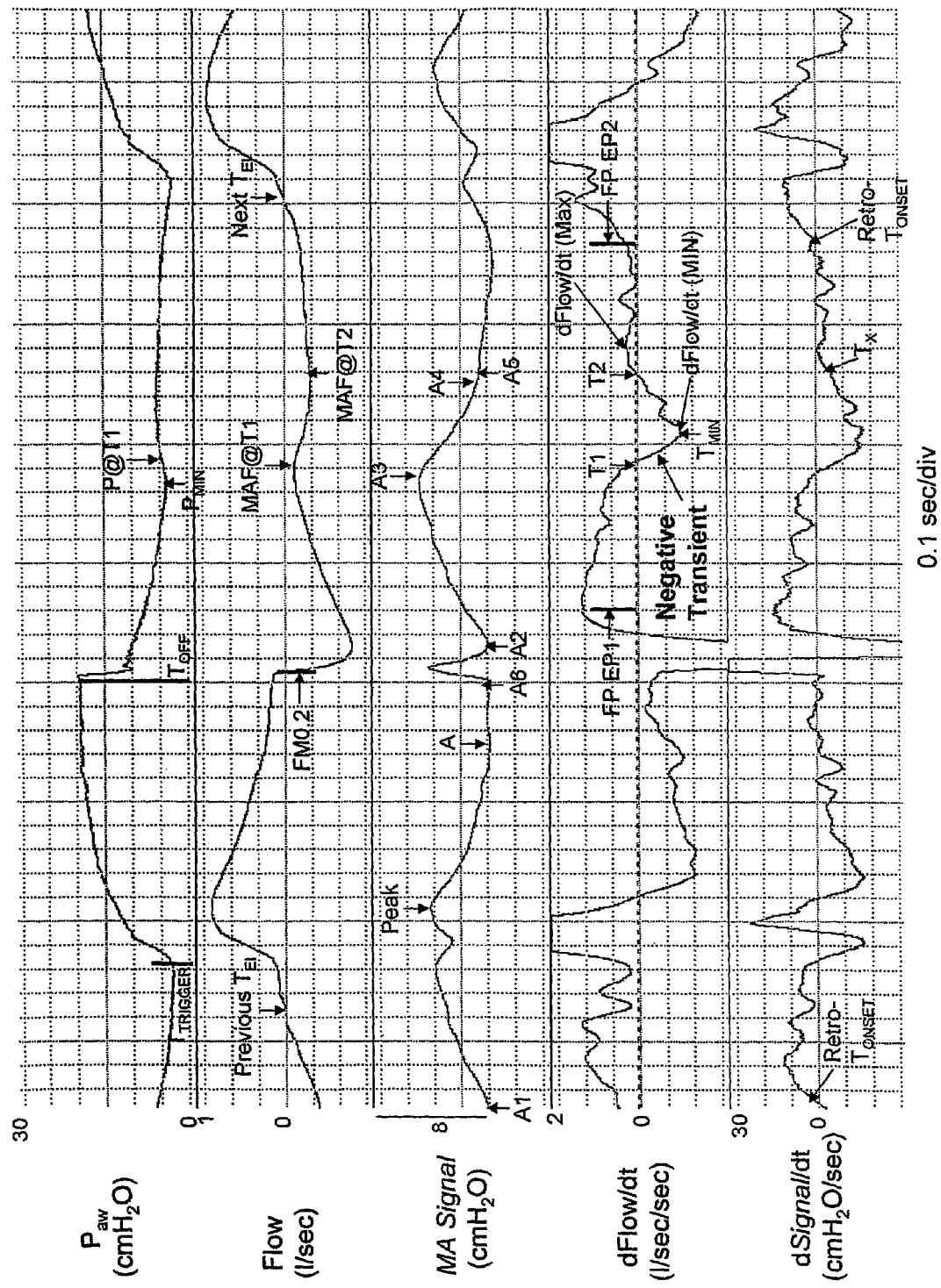

Non Real-Time Functions 62, FIG. 22:

There are a large number of functions performed on elapsed breaths. Only those relevant to the current claims will be described in detail. FIGS. 23 and 24 show the various variables used in executing the non real-time functions. As well, these Figures show the primary measurements made from these variables and the terms used in the following description.

The non real-time functions are triggered by the appearance of a valid $T_{IE}$ identified by the appropriate real-time function 43. Once a valid $T_{IE}$ is detected the next step is to determine whether there was a ventilator breath associated with the immediately preceding inspiratory phase (some inspiratory phases are not assisted). This is done in two steps: First, look for evidence of a cycling-off event ($T_{OFF}$). If a valid $T_{OFF}$ is found, the next step is to determine when the ventilator was triggered ($T_{TRIGGER}$). This is done by scanning back from $T_{OFF}$ until a point is reached where certain $T_{TRIGGER}$ criteria are met.

1) Identification of $T_{OFF}$ 46: ($P_{aw}$ tracing, FIG. 23). Where the system of the present invention is embedded in a ventilator, $T_{OFF}$ can be derived directly from the ventilator's control system. In a freestanding system, such as the current prototype, a special algorithm is necessary. In the preferred embodiment, $T_{OFF}$ is identified as follows:

Determine minimum $dP_{aw}/dt$ in interval [$T_{IE}$+0.25 sec] to ([$T_{IE}$−0.50 sec] or [preceding $T_{EI}$−0.20 sec] whichever is later). Time of minimum $dP_{aw}/dt$ is $T_{MIN}$. If minimum $dP_{aw}/dt$ is >−10, there is no $T_{OFF}$ (i.e. the inspiratory phase was unsupported by ventilator).

Determine duration (dT) of negative $dP_{aw}/dt$ transient containing minimum $dP_{aw}/dt$.

Calculate $dP_{aw}$ Product from $dT*$minimum $dP_{aw}/dt$.

Determine maximum drop in $P_{aw}$ (i.e. $dP_{aw}$) during said negative $dP_{aw}/dt$ transient from $[P_{aw}$ at transient onset $-0.05$ sec$]$–lowest $P_{aw}$ during the transient.

If minimum $dP_{aw}/dt<-30$, $dP_{aw}$ Product$<-3$, AND $dP_{aw}>2.0$, place $T_{OFF}$ at $T_{MIN}-0.10$ sec. Otherwise, Determine dFlow/dt at $T_{MIN}$;

Determine $dP_{aw}$(max) from $[P_{aw}$ at $T_{MIN}-0.1$ sec$]-[P_{aw}$ at $T_{EI}]$.

If dFlow/dt at $T_{MIN}$ is $<-1.5$ AND $dP_{aw}$(max)$>2.0$, place $T_{OFF}$ at $T_{MIN}-0.10$ sec. Otherwise, there is no $T_{OFF}$.

2) Identification of $T_{TRIGGER}$ 47:

If no $T_{OFF}$, there is no $T_{TRIGGER}$. If a $T_{OFF}$ exists, scan forward from [preceding $T_{EI}-0.1$ sec] to $T_{OFF}$. $T_{TRIGGER}$ is the earliest of:

First point at which $dP_{aw}/dt$ first exceeds 15 (point X) if: a) $dP_{aw}/dt$ remains $>15$ for 0.1 sec, b) dFlow/dt at X$>0$, AND flow at X$>0.1$.

First point where $[P_{aw}-P_{aw}$ at $T_{EI}]>1.0$ AND $dP_{aw}/dt>0$

First point (X) where $dP_{aw}/dt>0$ provided: a) $dP_{aw}/dt$ remains $>0$ for 0.1 sec AND $([P_{aw}$ at X+100 ms$]-[P_{aw}$ at X$])$ is $>1.0$.

First point (X) where Flow$>0.3$ provided: a) Flow remains $>0.3$ for 50 ms and $dP_{aw}/dt$ at (X)$>0$.

The remaining functions are executed each time a ventilator breath is identified from the above two functions.

3) Find FM0.2 (flow channel, FIG. 23) 48: Point, beyond $T_{IE}$, at which expiratory flow declines below $-0.2$ l/sec.

4) Calculate Retrospective $T_{ONSET}$ ($dP_{SIGNAL}/dt$ channel, FIG. 23) 49: This is the onset of the inspiratory effort immediately preceding $T_{TRIGGER}$. It is determined by scanning back from $T_{TRIGGER}$ to find the highest dSignal/dt in the interval $T_{TRIGGER}$ to $[T_{TRIGGER}-0.5$ second$]$. Then, starting from this highest dSignal/dt value it scans back until dSignal/dt decreases below 15% of the highest dSignal/dt. The positive dSignal/dt transient preceding $T_{TRIGGER}$ must meet minimum criteria for it to be considered an effort (duration$>60$ msec OR an increase in Signal$>1.0$ cmH$_2$O during the transient AND dSignal/dt exceeds 5 cmH$_2$O/sec for at least ¼ of transient duration). If no transient meeting these minimum criteria is found preceding $T_{TRIGGER}$, there is no Retrospective $T_{ONSET}$.

5) Placement of Elastance Points (EP points; dFlow/dt channel, FIG. 23): These are the points at which values of $P_{aw}$, flow and volume are to be sampled for the sake of estimating $K_V$. EP1 point is the high volume point, corresponding to point "a" in equation 5 and EP2 point is the low volume point, corresponding to point "b" in equation 5. This procedure is executed in 4 steps (50 to 53, FIG. 22):

A) Initial (First pass) placement of EP points (50): First pass EP1 (FP EP1) is placed at the later of $[T_{OFF}+0.2$ sec$]$ OR $[FM0.2+0.1$ sec$]$. First pass EP2 (FP EP2) is placed at Retrospective $T_{ONSET}$ (Retro for short) OR, if no Retro, at $T_{EI}$.

B) Identification and classification of Negative flow transients (51): 50 msec moving average of Signal (MA Signal) is scanned between first pass EP1 and Retro [or, if no Retro, next $T_{EI}$] for presence of negative transients in dFlow/dt that end within the search interval. Each transient found is classified into one of 6 types depending on a number of measurements. FIG. 24 shows the measurements that form the basis for classification. As can be seen, a negative dFlow/dt transient is present between first pass EP1 (FP EP1) and the next Retro. The various measurements and determinations shown in the Figure are as follows:

T1: Time of onset of transient

T2: Time of end of transient $T_{MIN}$: Time of minimum dFlow/dt within the transient.

$T_X$: First point where dSignal/dt increases above $-5$ while scanning forward from $[T2-100$ msec$]$.

Previous $T_{EI}$: $T_{EI}$ preceding the previous ventilator breath.

Next $T_{EI}$: $T_{EI}$ preceding the following ventilator breath.

FP EP1: First pass EP1 (see above).

FP EP2: First pass EP2 (see above).

P@T1: $P_{aw}$ at T1.

$P_{MIN}$: Lowest $P_{aw}$ between P@T1 and [T1$-1.0$ sec] OR FM0.2 whichever is later.

MAF@T1: 50 msec moving average of flow at T1.

MAF@T2: 50 msec moving average of flow at T2.

dFlow/dt(MIN): Lowest dFlow/dt reached within the transient.

dFlow/dt(MAX): Highest dFlow/dt reached in interval T2 to ([T2+150 msec] or [Retro$-100$ msec], whichever is earlier).

Peak: Highest 50 msec moving average (MA) of Signal in interval $T_{TRIGGER}$ to $T_{OFF}$ of preceding ventilator inflation phase.

A: Lowest MA Signal between Peak and $T_{OFF}$.

A1: MA Signal at Retro of previous inspiration OR (if no Retro) $T_{TRIGGER}-100$ msec.

A2: Lowest MA Signal between T1 and [previous FM0.2+ 100 msec].

A3: MA Signal at [T1$-25$ msec].

A4: MA Signal at [T2$-25$ msec].

A5: MA Signal at $T_X$.

A6: MA Signal at $T_{OFF}$.

Figure 25:
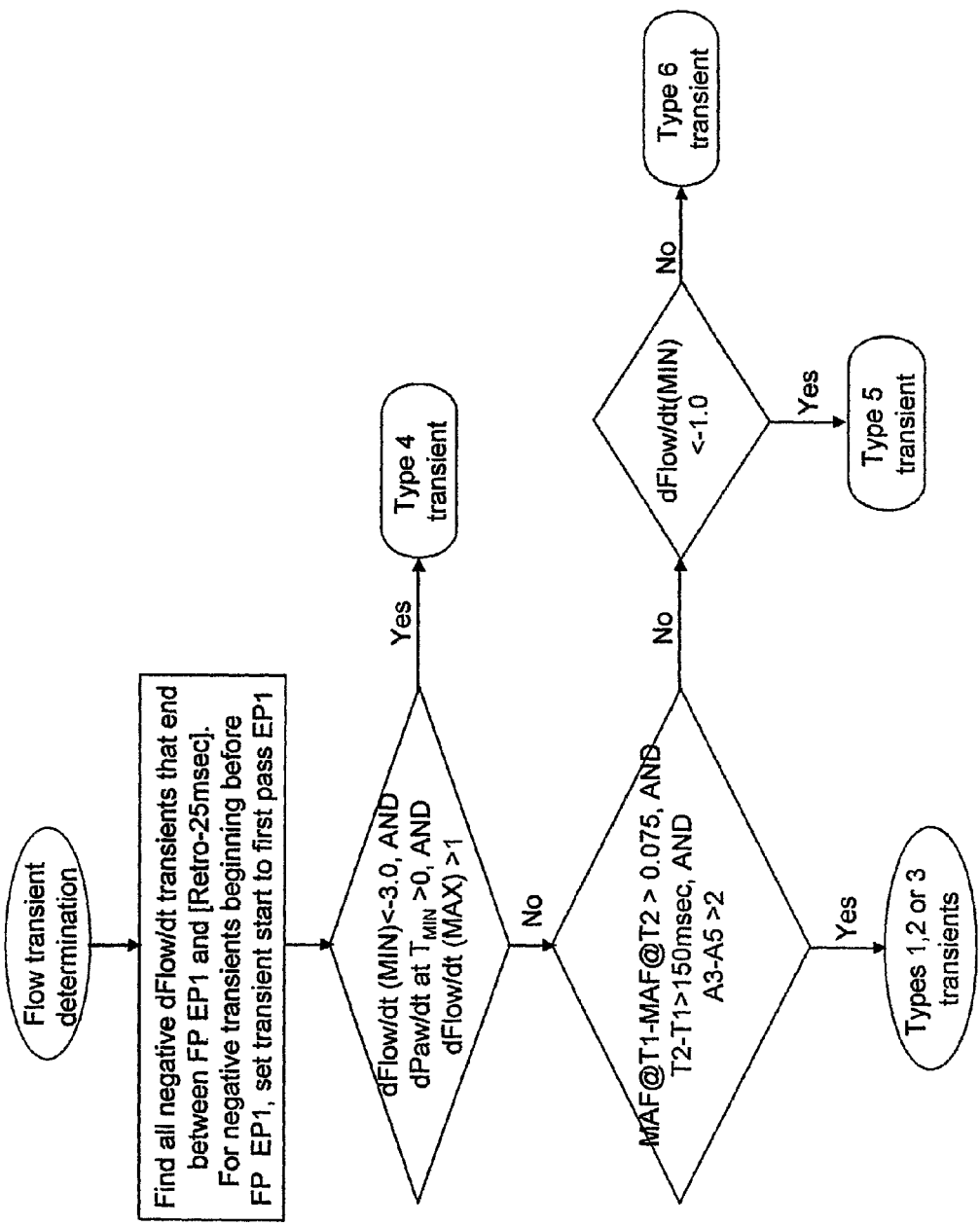
FIGS. 25 and 26 are flow charts that illustrate the classification process for the transients.
Figure 26:
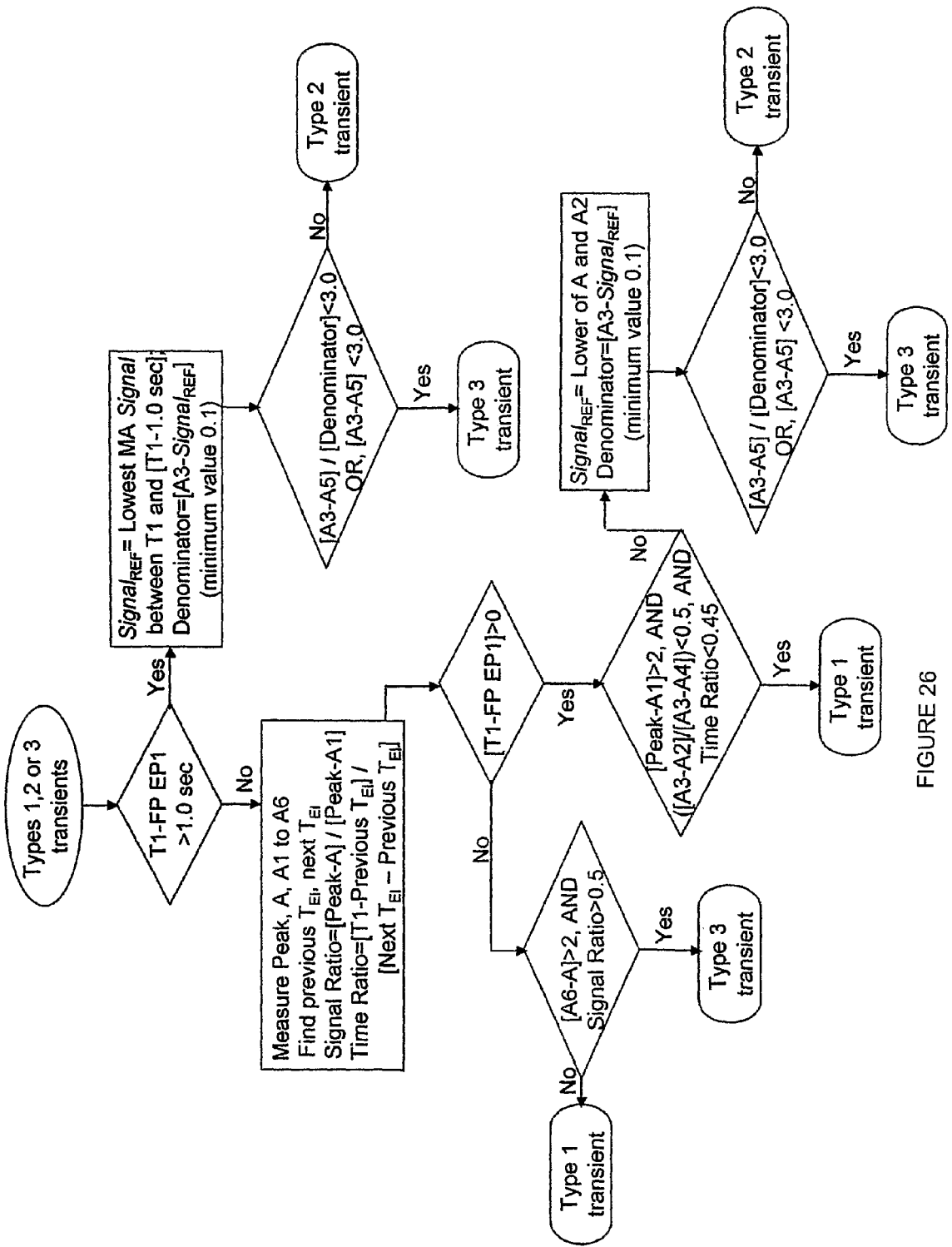

FIGS. 25 and 26 are flow charts that describe the classification process.

C) Reclassify some type 3 transients into type 5 52: If a type 3 transient is found within the search interval it is subjected to further investigation. Thus, if another type 3 or type 5 transient begins within ±0.9 second of T1 of the type 3 transient in question, it is reclassified into a type 5 transient. This is because a type 3 transient is supposed to reflect a regular inspiratory effort that failed to trigger the ventilator (FIG. 10). Because respiratory rate virtually never exceeds 65/minute, the presence of another similar transient, or a type 5 transient, within 0.9 second suggests that, rather than representing respiratory efforts, both transients reflect forces that repeat at a higher frequency, such as cardiac oscillations or secretions. The latter are normally classified as type 5 transients. Similarly, a type 3 transient is reclassified to type 5 if its T1 is within 0.45 second of a preceding $T_{END}$.

D) Final placement of EP points 53: The placement of EP points is aborted, and by extension, the breath is excluded from $K_V$ calculation, if any of the following conditions are encountered:

a. Duration of preceding breath (i.e. current $T_{TRIGGER}-$ previous $T_{TRIGGER})<1$ second as this reflects an unstable breathing pattern.

b. Current breath expired volume $<0.7*$ current breath inspired volume as this reflects unstable breathing pattern or significant leaks.

c. $T_{IE}<T_{OFF}$ of current breath as this reflects marked recruitment of expiratory muscles at the beginning of the exhalation phase.

d. Type 3 or type 5 flow transient beginning within 0.4 second of Retro. These types of flow transients reflect the occurrence of an important force during the exhalation phase. When they occur close to the onset of an effort (Retro in this case), they cannot be proper respiratory efforts and are, hence, are of unknown origin. Because of their uncertain nature, safe time boundaries cannot be established and the breath is discarded.

e. Presence of a type 4 flow transient at any time in the exhalation phase.

In all other breaths first pass EP points are adjusted as follows:

a. If there is a type 2 flow transient, move FP EP2 point back to the onset (T1) of the type 2 transient.

b. First pass EP1 remains as is if there are no flow transients or the transients are of types 2 or 6.

c. For type 1 transients, FP EP1 is moved forward to end of transient.

d. For type 3 transients check [A2–A] (see FIG. 24). If [A2–A]<2, EP1 stays as is. If >2, move EP1 to end of transient+100 msec.

e. If one or more type 5 transients are found in the interval FP EP1 to FP EP1+500 msec, move EP1 to end of the last type 5 transient within this interval. Then look for other type 5 flow transients in the interval new EP1 to final EP2. If none found, keep EP1 in new place. If one or more type 5 found, move EP1 again to end of last (between the second pass EP1 and final EP2) type 5 transient+0.2 sec.

f. If, after above adjustments, [EP2−EP1]>4.0 seconds move EP2 back to [EP1+4 seconds]. Recheck for presence of types 3 and 5 flow transient in the new location as per above steps, treating the newly placed EP2 as an EP1 and moving it accordingly.

g. Finally, check difference in volume between final EP1 and final EP2 points. If <40% of total exhaled volume, the breath is discarded and no $K_V$ calculation is performed.

6) Calculation of $K_V$ 54: 50 msec moving average of $P_{aw}$, flow and volume at final EP 1 and EP2 are calculated and stored in memory. Equation 5 is applied where EP1 data are inserted as the "a" points and EP2 data are inserted as the "b" points. $K_{F2}$ is a constant obtained from the look-up table corresponding to the endotracheal tube size inputted at start-up. $K_{F1}$ is taken from the current value in memory based on the results of the $K_{F1}$ error function (see next). $K_V$ for the current breath is added to the $K_V$ buffer that contains values from the last 10 valid breaths. The first value in the buffer is discarded and a new 10-breath average is obtained. This value is then used in real-time calculation of Signal.

7) Calculation of $K_{F1}$ error (see FIG. 13) 55,56: This is the function that minimizes step changes in calculated Signal at the times of ventilator triggering and cycling-off. Although calculations may be done at triggering only or at cycling-off only, in the preferred embodiment calculations are done both at the time of triggering (Early $K_{F1}$ error calculation 55) and at cycling-off (late $K_{F1}$ error calculation 56). This is followed by a process of selection between the two values:

A) Early $K_{F1}$ error calculation 55: The principle of the approach used in the preferred embodiment is to extrapolate the Signal trajectory across the period of rapid change in flow (at triggering) along a slope that is intermediate between Signal slope just before triggering and its slope once the phase of fast flow change is over. The use of an intermediate slope takes into account the fact that the rate of rise of inspiratory effort is not constant but may increase or decrease as effort progresses. By measuring Signal trajectory before and after the period of the step change in flow, and averaging them, one obtains a potentially more accurate estimate of the real rate of rise of Signal had there been no abrupt change in flow. The difference between actual Signal level at a point where flow is no longer changing rapidly (herein call $T_{REF}$) and level projected at the same point had there been no abrupt change in flow provides an estimate of the magnitude of artefactual change in Signal resulting from the abrupt change in flow (ΔSignal, FIG. 13).

Measurements:

These measurements are made from data of recently elapsed breaths as follows (see FIG. 23 for explanation of discrete terms):

dFlow/dt ($T_{TR}$): dFlow/dt at $T_{TRIGGER}$ is measured as follows:

1. If no Retro OR if [$T_{TRIGGER}$−Retro]<0.025, dFlow/dt ($T_{TR}$)=0.1 l/sec/sec;

2. If [$T_{TRIGGER}$−Retro]>0.1 sec, dFlow/dt ($T_{TR}$)=actual dFlow/dt at $T_{TRIGGER}$; minimum value of 0.1.

3. If 0.025<[$T_{TRIGGER}$−Retro]<0.1 sec: dFlow/dt ($T_{TR}$)= ([average flow between $T_{TR}$ and $T_{TR}$−0.025 sec]−[average flow between Retro and Retro−0.025 sec])/[$T_{TR}$−Retro]

dFlow/dt (Peak): Highest dFlow/dt in interval $T_{TR}$ to $T_{TR}$+0.25 sec.

dFlow/dt ($T_{TR}$+0.25 sec): dFlow/dt 0.25 sec after $T_{TR}$.

$T_{REF}$: Time at which dFlow/dt has decreased to a low level after triggering. It is determined as follows: Scan back from [$T_{TR}$+0.25 sec] until dFlow/dt is just >dFlow/dt ($T_{TR}$) OR >0.5, whichever is earlier. This is first pass $T_{REF}$. If interval between first pass $T_{REF}$ and time of dFlow/dt (Peak) is <0.1 sec, move $T_{REF}$ to time of dFlow/dt (Peak)+0.1 sec. This is final $T_{REF}$. If dFlow/dt ($T_{TR}$+0.25 sec)>dFlow/dt ($T_{TR}$) do not calculate early $K_{F1}$ error (see below).

Significant negative dSignal/dt transient: There are two possible reasons for Signal level to undergo a step decline soon after triggering. First, the inspiratory effort may actually terminate. This is a physiological response and not a technical artefact. Second, there is an error in $K_{F1}$. It is, therefore, important to determine whether a step reduction in Signal at triggering is physiological or technical. A physiological reduction (actual effort termination) results in a sustained reduction in Signal whereas with a technical artefact Signal should resume rising beyond the period of rapid increase in flow. The following criteria strongly suggest that a step reduction in Signal is physiological:

Negative dSignal/dt transient that begins between [$T_{TR}$−0.1 sec] and $T_{REF}$, AND Duration of negative dSignal/dt transient>0.15 sec, AND Denominator>2.0, where Denominator is [Signal level at transient onset−Signal level at Retro (OR $T_{TR}$ if no Retro)], AND ([Signal level at transient onset−Signal level at transient end]/Denominator)>0.6.

dSignal/dt ($T_{TR}$): dSignal/dt at $T_{TRIGGER}$ is measured as follows:

1. If no Retro, dSignal/dt ($T_{TR}$)=0 cmH$_2$O/sec;

2. If [$T_{TRIGGER}$−Retro]>0.1 sec, dSignal/dt ($T_{TR}$)=actual dSignal/dt at $T_{TRIGGER}$;

3. If [$T_{TRIGGER}$−Retro]<0.1 sec: dSignal/dt ($T_{TR}$)=([average Signal between $T_{TR}$ and $T_{TR}$−0.025 sec]−[average Signal between Retro and Retro−0.025 sec])/[$T_{TR}$−Retro].

dT: This is [$T_{REF}$−$T_{TR}$−0.1].

Signal ($T_{TR}$): Average Signal between $T_{TR}$ and [$T_{TR}$−0.025 sec].

Signal ($T_{REF}$): Average Signal between [$T_{REF}$−0.125 sec] and [$T_{REF}$−0.075 sec].

Flow ($T_{REF}$): Average flow between [$T_{REF}$−0.125 sec] and [$T_{REF}$−0.075 sec].

Flow ($T_{TR}$): Average flow between $T_{TR}$ and [$T_{TR}$−0.025 sec].

Calculation of early $K_{F1}$ error:

a) Do not calculate error (i.e. invalid breath):

If [dFlow/dt (Peak)/dFlow/dt ($T_{TR}$)]<2. A value that is <2 indicates that there was not enough increase in flow acceleration related to triggering.

If dFlow/dt ($T_{TR}$+0.25 sec)>dFlow/dt ($T_{TR}$) OR >0.5. In such cases flow acceleration had not decreased enough by [$T_{TR}$+0.25 sec]. This would necessitate extrapolation for longer periods, which is not advisable.

If a Significant negative dSignal/dt transient was found. This would indicate a physiological termination of effort during the period of analysis so that results do not reflect a $K_{F1}$ error.

b) If none of the above exclusion criteria is found, calculate $K_{F1}$ error from:

$K_{F1}$ error=(Signal ($T_{TR}$)+(0.5*dT*(dSignal/dt ($T_{TR}$)+dSignal/dt at $T_{REF}$))−Signal ($T_{REF}$))/(Flow ($T_{REF}$)−Flow ($T_{TR}$))

Calculation of corrected $K_{F1}$:

Corrected $K_{F1}$=$K_{F1}$ error+$K_{F1}$ used to generate Signal in the elapsed breath being examined. If Corrected $K_{F1}$>25, it is reduced to 25. If Corrected $K_{F1}$<2, it is increased to 2.

B) Late $K_{F1}$ error calculation 56: The same general approach is used here. The trajectory of Signal prior to ventilator cycling-off is extrapolated across the interval where flow changes rapidly, using a slope that is intermediate between the slope before cycling-off and the slope after the phase of rapid flow change is over. The difference between the extrapolated and actual Signal values at the end of the phase of rapid flow decline is a measure of the step change in Signal (dSignal, FIG. 13) related to rapid flow change.

Measurements:

These measurements are made from data of recently elapsed breaths as follows (see FIG. 23 for explanation of discrete terms):

$F_{PEAK}$: Highest (most negative) expiratory flow in interval $T_{OFF}$ to [$T_{OFF}$+1.0 sec] OR Retro whichever is earlier.

$F_{REF}$: Highest (most negative) expiratory flow in interval $T_{OFF}$ to [$T_{OFF}$+0.2 sec].

F (+0.1): Average flow in interval [$F_{PEAK}$+0.075 sec] to [$F_{PEAK}$+0.125 sec].

$T_{REF}$: $T_{REF}$ is $T_{OFF}$+0.15 sec OR time of $F_{REF}$, whichever is later.

F ($T_{REF}$): Average flow between [$T_{REF}$+0.025 sec] and [$T_{REF}$−0.025 sec].

dT: Interval between $T_{REF}$ and $T_{OFF}$.

Signal ($T_{OFF}$): Average Signal amplitude between [$T_{OFF}$−0.025 sec] and [$T_{OFF}$+0.025 sec].

Signal ($T_{REF}$): Average Signal amplitude between [$T_{REF}$−0.025 sec] and [$T_{REF}$+0.025 sec].

dSignal/dt ($T_{OFF}$): dSignal/dt at $T_{OFF}$.

dSignal/dt ($T_{REF}$): dSignal/dt at [$T_{REF}$+0.1 sec].

Calculation of Late $K_{F1}$ error:

a. Do not calculate error (i.e. invalid breath):

If $F_{REF}/F_{peak}$<0.8, OR

F (+0.1)/$F_{peak}$<0.65.

b. If none of the above exclusion criteria is met, calculate late $K_{F1}$ error as follows:

Late $K_{F1}$ error=[Signal ($T_{OFF}$)+(0.5*dT*(dSignal/dt ($T_{OFF}$)+dSignal/dt($T_{REF}$)))−Signal ($T_{REF}$)]/[flow at $T_{OFF}$−F ($T_{REF}$)].

Calculation of corrected $K_{F1}$:

Corrected $K_{F1}$=$K_{F1}$ used to generate Signal−Late $K_{F1}$ error.

If Corrected $K_{F1}$>25, it is reduced to 25. If Corrected $K_{F1}$<2, it is increased to 2.

C) Updating the current $K_{F1}$ value 57:

Selection between Early and Late $K_{F1}$ correction: If a breath produces both a valid early and late $K_{F1}$ error calculation, the late one is selected because it is less subject to assumptions about extrapolation trajectory. If the breath produces only one valid $K_{F1}$ error calculation, that value is used. If both calculations are not valid, the $K_{F1}$ value in the buffer is not updated. Corrected $K_{F1}$ is entered in the $K_{F1}$ buffer. The buffer contains values from the last 10 valid breaths. The average of these 10 values is used to generate Signal in next breath. The buffer begins with a default value of 10.

Figure 2:
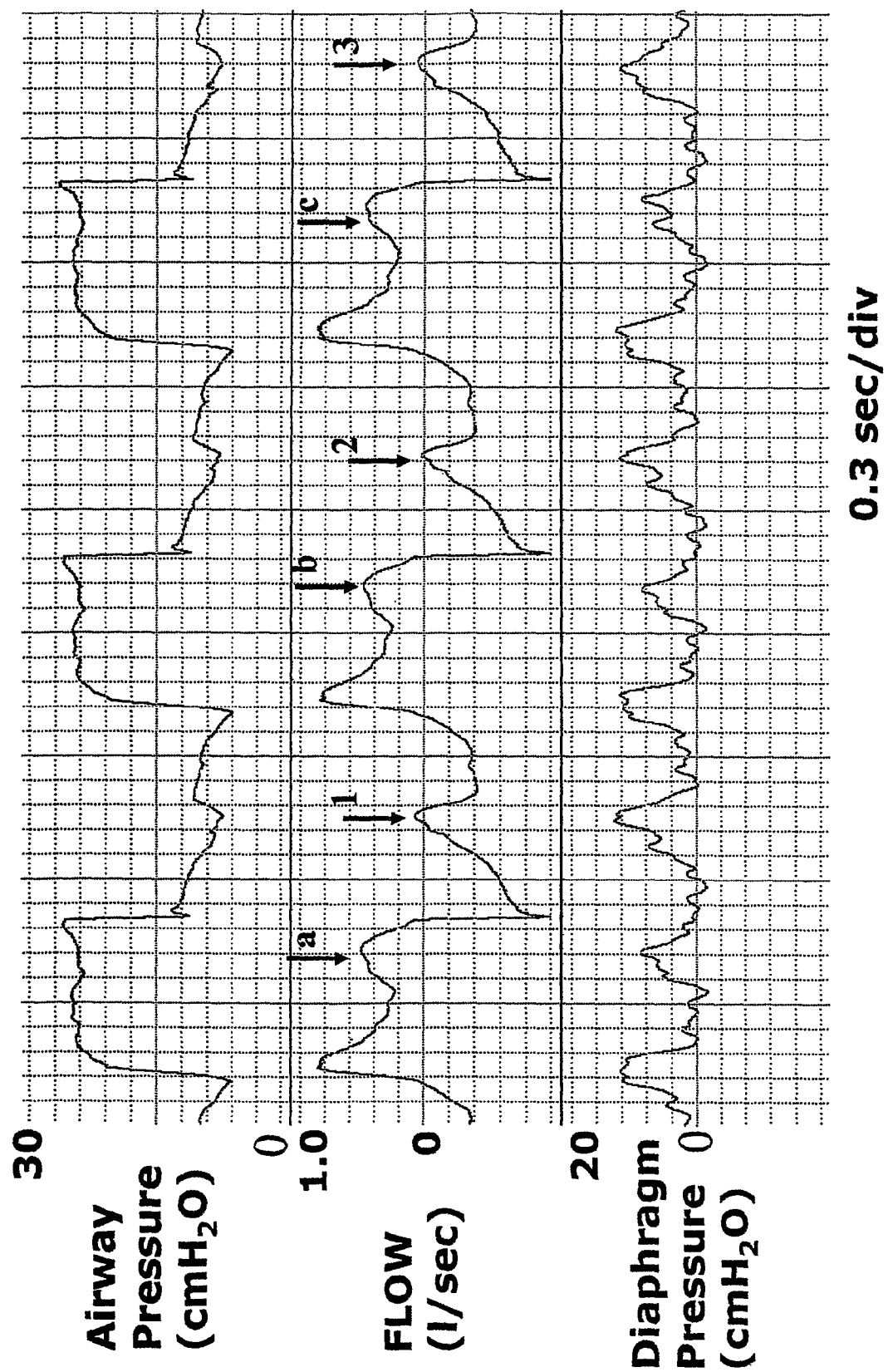
FIG. 2 contains further traces of airway pressure, flow and diaphragm pressure for ventilator cycles.

7) Other Functions 58: The current preferred embodiment executes several additional functions on the Signal and other variables generated in elapsed breaths, including:

Identifying inspiratory efforts that occur during the inflation phase of the ventilator (e.g. arrows marked "b" in FIG. 2).

Calculating trigger delay (difference between $T_{TRIGGER}$ and Retro $T_{ONSET}$).

Identifying, in retrospect, the beginning of the declining phase of Signal (Retro $T_{END}$).

Calculating cycling-off delay (difference between $T_{OFF}$ and Retro $T_{END}$).

Calculating ventilator respiratory cycle duration (Ventilator $T_{TOT}$) from the difference between successive $T_{TRIGGER}$s.

Calculating ventilator rate from number of $T_{TRIGGER}$s in past minute.

Calculating tidal volume.

Calculating true patient respiratory rate (Patient RR) from number of efforts, in the past minute, that triggered the ventilator+number of ineffective efforts during the exhalation phase+number of extra efforts during the inhalation phase.

Calculating the period to be excluded from $T_{ONSET}$ identification in real-time processing ($T_{ONSET}$ Window Delay; see Background) based on patient RR.

Calculating the period to be excluded from $T_{END}$ identification in real-time processing ($T_{END}$ Window Delay; see Background).

Determining the threshold increase in Signal required for real-time identification of $T_{ONSET}$.

Most of these functions have been described in detail in the aforementioned U.S. patent application Ser. No. 10/517,384 and EP application 03 739906; Method and Device for monitoring and Improving Patient-Ventilator Interaction, which are incorporated here by reference. Others are of no specific relevance to the current claims and, accordingly, will not be described.

8) Update Summary Table 59: A table is created at "start-up" that is updated with each ventilator breath ($T_{TRIGGER}$). The table is intended to provide the user with a summary of the state of patient-ventilator interaction. Based on this information the user may make appropriate adjustments to ventilator settings to improve the interaction, if needed. Alternatively, or in addition, some of the outputs can be channelled to the ventilator's cycling mechanism to effect such optimization automatically. The table generated by the current preferred embodiment includes data specifically generated by the methods of the current invention (i.e. Signal reflecting patient efforts) as well as other information of interest to clinicians, obtained without the benefit of Signal, and which are commonly displayed in many prior art devices. Items that specifically rely on the methods of the current invention are highlighted:

Average Tidal volume in past minute

Ventilator rate in past minute

Minute ventilation in past minute $P_{aw}$ at $T_{EI}$ (referred to as PEEP)

Assist delivered by ventilator ([Maximum $P_{aw}$ between $T_{TRIGGER}$ and $T_{OFF}$]−PEEP)

Number of ineffective efforts in exhalation in past minute

Number of extra efforts during the ventilator's inflation phase in past minute

Patient respiratory rate

Average trigger delay in past minute

Average cycling-off delay in past minute

Current $K_{F1}$

Current $K_V$

Appropriate comments: A list of comments is stored in memory.

When certain values in the summary table reach specified levels, an appropriate comment is selected from the list and is displayed on the monitor. These comments include statements about extent and the likely mechanisms of non-synchrony and suggestions as to ventilator adjustments that might improve non-synchrony.

Options on the graphical user interface enable the user to display the latest values (last 1.0 minute) in the table on the screen, to display trends of selected variables over specified time intervals, or to display comments.

SUMMARY OF DISCLOSURE

In summary of this disclosure, the present invention provides a method and apparatus for generating a signal that mirrors changes in the level of effort exerted by respiratory muscles of patients on mechanical ventilatory support. Modifications are possible within the scope of the invention.

What I claim is:

1. A method for generating a signal that mirrors changes in the level of effort exerted by respiratory muscles of patients on mechanical ventilatory support (Signal), comprising:

monitoring airway pressure ($P_{aw}$), rate of gas flow (F), and volume of gas flow (V) of the patient;

inputting $P_{aw}$, F and V data collected to a computer with said computer performing the following processes on the collected data;

calculating a composite pressure signal that mirrors changes in the level of effort exerted by respiratory muscles of patients on mechanical ventilatory support (Signal) from the relationship:

Signal=current $V*K_v$+current $F*K_F$−current $P_{aw}$, wherein, $K_F$ is a coefficient that converts flow into equivalent resistive pressure units and $K_v$ is a coefficient that converts volume into equivalent elastic pressure units; said calculation begins using assumed (arbitrary) values for $K_F$ and $K_v$ while subsequently, as more data is analysed, utilizing Patient-Specific values;

calculating a Patient-Specific $K_F$ from elapsed data by determining the value that minimizes step changes in calculated Signal at the time of ventilator triggering and/or cycling-off;

calculating a Patient-Specific $K_v$ from elapsed data by steps comprising:

scanning of stored F or Paw information, and/or the time derivative thereof, during the exhalation phase of elapsed breaths and identifying instances where the trajectory of either F or $P_{aw}$ transiently reverses direction during said exhalation phase, thereby detecting transients;

selecting two or more points within the exhalation phase that are at preselected distances away from identified transients;

calculating the value of $K_v$ required to force the values of Signal calculated at said selected points in elapsed breaths to be substantially equal when said selected value of $K_F$ is used as the flow coefficient;

wherein said generated Signal is either displayed on a screen to serve the purpose of monitoring patient efforts and/or is used to control the output of the ventilator.

2. The method of claim 1 wherein $F*K_F$ is the sum of two components, one component being a predetermined function representing the pressure drop along the endo-tracheal tube and another component, $K_{F1}$, that is calculated from elapsed data and selected to minimize step changes in calculated Signal at the times of ventilator triggering and/or cycling-off.

3. The method of claim 1 wherein said transients are classified into a number of types by reference to specified criteria.

4. The method of claim 3 wherein said preselected distances are set according to identified transient type.

5. The method of claim 2 wherein $K_F$ or $K_{F1}$ required to minimize step changes in Signal is calculated both at the time of ventilator triggering and time of cycling-off and wherein, if differences exist between the two determinations, one or the other is chosen based on pre-specified criteria.

6. The method of claim 5 wherein if differences exist between the two determinations, a simple or weighted average value is obtained for use in calculating Signal.

7. The method of claim 1 wherein the generated Signal is further processed to identify the onset of Signal's rising phase ($T_{ONSET}$) and/or onset of Signal's declining phase ($T_{END}$).

8. The method of claim 7 wherein identification of $T_{ONSET}$ is precluded for a specified period in the ventilator's exhalation phase ($T_{ONSET}$ Window Delay) and/or identification of $T_{END}$ is precluded for a specified period in the ventilator's inflation phase ($T_{END}$ Window Delay).

9. The method of claim 8 wherein a minimum value for $T_{ONSET}$ Window Delay is specified.

10. The method of claim 9 wherein said minimum value for $T_{ONSET}$ Window Delay is a function of patient's respiratory rate.

11. The method of claim 8 wherein a minimum value for $T_{END}$ Window Delay is specified.

12. The method of claim 10 wherein said minimum value for $T_{END}$ Window Delay is a function of patient's respiratory rate.

13. The method of claim 7 wherein said generated $T_{ONSET}$s and/or $T_{END}$s are used to effect triggering and/or cycling-off of ventilator cycles.

14. The method of claim 7 wherein generated Signal is further processed to obtain information about patient-ventilator interaction and wherein said information is communicated to a user through display on a monitor or by other forms of communication.

15. The method of claim 14 wherein said information includes at least one of display of the Signal itself, $T_{onset}$ and $T_{end}$ markers, trigger delay, cycling-off delay, patient's respiratory rate, number or rate of ineffective efforts.

16. The method of claim 1 wherein said calculated value of $K_F$ and/or $K_V$ is/are communicated to a user through display on a monitor or by other forms of communication.

17. The method of claim 16 wherein said communicated information is accompanied by narrative/commentary providing interpretation of the findings and/or suggestions for ventilator adjustment that might improve patient-ventilator interaction.

18. A device for generating a signal that mirrors changes in the level of effort exerted by respiratory muscles of patients on mechanical ventilatory support (Signal), comprising:

sensors and associated circuitry for obtaining information regarding airway pressure ($P_{aw}$), rate of gas flow (F), and volume of gas flow (V) of such a patient; and a computer that executes the following functions:

storing collected $P_{aw}$, F and V data in computer memory;

calculating a composite pressure signal that mirrors changes in the level of effort exerted by respiratory muscles of patients on mechanical ventilatory support (Signal) from the relationship:

Signal=current $V*K_v$+current $F*K_F$−current $Paw$, wherein, $K_F$ is a coefficient that converts flow into equivalent resistive pressure units and $K_v$ is a coefficient that converts volume into equivalent elastic pressure units; said calculation begins using assumed (arbitrary) values for $K_F$ and $K_v$ while subsequently, as more data is analysed, utilizing Patient-Specific values;

calculating a Patient-Specific $K_F$ from elapsed data by determining the value that minimizes step changes in calculated Signal at the time of ventilator triggering and/or cycling-off;

calculating a Patient-Specific $K_v$ from elapsed breath data by steps comprising the following functions:

scanning of stored F or $P_{aw}$ information, and/or the time derivative thereof, during the exhalation phase of elapsed breaths and identifying instances where the trajectory of either F or $P_{aw}$ transiently reverses direction during said exhalation phase thereby detecting transients;

selecting two or more points within the exhalation phase that are at preselected distances away from identified transients, and calculation functions to determine the value of $K_v$ required to force the values of Signal calculated at said selected points in elapsed breaths to be substantially equal when said selected value of $K_F$ is used as the flow coefficient, wherein said generated Signal is either displayed on a screen to serve the purpose of monitoring patient efforts and/or is used to control the output of the ventilator.

19. The device of claim 18 wherein $F*K_F$ is the sum of two components, one component being a predetermined function representing the pressure drop along the endo-tracheal tube and another component $K_{F1}$, that is calculated from elapsed data and selected to minimize step changes in calculated Signal at the times of ventilator triggering and/or cycling-off.

20. The device of claim 18 wherein said transients are classified into a number of types by reference to specified criteria.

21. The device of claim 20 wherein said preselected distances are set according to identified transient type.

22. The device of claim 19 wherein $K_F$ or $K_{F1}$, required to minimize step changes in Signal is calculated both at the time of ventilator triggering and time of cycling-off and wherein, if differences exist between the two determinations, one or the other is chosen based on pre-specified criteria.

23. The device of claim 22 wherein, if differences exist between the two determinations, a simple or weighted average value is obtained for use in calculating Signal.

24. The device of claim 18 wherein the computer executes the additional features of further processing the generated Signal to identify the onset of Signal's rising phase ($T_{ONSET}$) and/or onset of Signal's declining phase ($T_{END}$).

25. The device of claim 24 wherein the computer executes the additional features of precluding identification of $T_{ONSET}$ for a specified period in the ventilator's exhalation phase ($T_{ONSET}$ Window Delay) and/or precluding identification of $T_{END}$ for a specified period in the ventilator's inflation phase ($T_{END}$ Window Delay).

26. The device of claim 25 wherein a minimum value for $T_{ONSET}$ Window Delay is specified.

27. The device of claim 26 wherein said minimum value for $T_{ONSET}$ Window Delay is a function of patient's respiratory rate.

28. The device of claim 26 wherein a minimum value for $T_{END}$ Window Delay is specified.

29. The device of claim 27 wherein said minimum value for $T_{END}$ Window Delay is a function of patient's respiratory rate.

30. The device of claim 24 wherein said computer executes the additional features of using generated $T_{ONSET}$ s and/or $T_{END}$s to effect triggering and/or cycling-off of ventilator cycles.

31. The device of claim 24 wherein the computer executes the additional features of further processing generated Signal to obtain information about patient-ventilator interaction and wherein said information is communicated to a user through display on a monitor or by other forms of communication.

32. The device of claim 31 wherein said information includes at least one of display of the Signal itself, $T_{onset}$ and $T_{end}$ markers, trigger delay, cycling-off delay, patient's respiratory rate, number or rate of ineffective efforts.

33. The device of claim 18 wherein the computer executes the additional features of communicating said calculated value of $K_F$ and/or $K_V$ to a user through display on a monitor or by other forms of communication.

34. The device of claim 33 wherein said communicated information is accompanied by narrative/commentary providing interpretation of the findings and/or suggestions for ventilator adjustment that might improve patient-ventilator interaction.

* * * * *